United States Patent
Schoor et al.

(10) Patent No.: US 10,442,844 B2
(45) Date of Patent: Oct. 15, 2019

(54) PEPTIDES AND COMBINATION OF PEPTIDES AND SCAFFOLDS THEREOF FOR USE IN IMMUNOTHERAPY AGAINST COLORECTAL CARCINOMA (CRC) AND OTHER CANCERS

(71) Applicant: IMMATICS BIOTECHNOLOGIES GMBH, Tübingen (DE)

(72) Inventors: Oliver Schoor, Tübingen (DE); Andrea Mahr, Tübingen (DE); Toni Weinschenk, Aichwald (DE); Anita Wiebe, Rübgarten (DE); Jens Fritsche, Dusslingen (DE); Harpreet Singh, Houston, TX (US)

(73) Assignee: IMMATICS BIOTECHNOLOGIES GMBH, Tuebingen (DE)

(*) Notice: Subject to any disclaimer, the term of this patent is extended or adjusted under 35 U.S.C. 154(b) by 0 days.

(21) Appl. No.: 15/979,089

(22) Filed: May 14, 2018

(65) Prior Publication Data
US 2018/0244741 A1    Aug. 30, 2018

Related U.S. Application Data

(63) Continuation of application No. 15/145,990, filed on May 4, 2016.

(60) Provisional application No. 62/157,684, filed on May 6, 2015.

(30) Foreign Application Priority Data

May 6, 2015 (GB) .................................. 1507719.1

(51) Int. Cl.
| | | |
|---|---|---|
| C07K 14/47 | (2006.01) | |
| A61K 39/00 | (2006.01) | |
| C07K 14/74 | (2006.01) | |
| C07K 16/28 | (2006.01) | |
| C12N 5/0783 | (2010.01) | |
| C12N 15/113 | (2010.01) | |
| C07K 14/725 | (2006.01) | |
| C07K 16/30 | (2006.01) | |
| A61P 35/00 | (2006.01) | |

(52) U.S. Cl.
CPC ...... *C07K 14/4748* (2013.01); *A61K 39/0011* (2013.01); *A61K 39/001154* (2018.08); *A61P 35/00* (2018.01); *C07K 14/7051* (2013.01); *C07K 14/70539* (2013.01); *C07K 16/2833* (2013.01); *C07K 16/3046* (2013.01); *C07K 16/3076* (2013.01); *C12N 5/0636* (2013.01); *C12N 15/1138* (2013.01); *A61K 2039/5154* (2013.01); *A61K 2039/5158* (2013.01); *C07K 2317/34* (2013.01); *C12N 2310/16* (2013.01); *C12N 2501/50* (2013.01)

(58) Field of Classification Search
CPC ....................................................... C07K 7/06
See application file for complete search history.

(56) References Cited

U.S. PATENT DOCUMENTS 6,630,297 B2    10/2003  Ollmann et al.

FOREIGN PATENT DOCUMENTS

| CN | 101168566 A | 4/2008 |
|---|---|---|
| WO | 2009/015842 A2 | 2/2009 |
| WO | 2015/018805 A1 | 2/2015 |

OTHER PUBLICATIONS

Montagna et al (Cytotherapy, 2012, vol. 14, pp. 80-90) (Year: 2012).*
Yee et al (Journal of Immunology, 1999, vol. 162, pp. 2227-2234) (Year: 1999).*
Great Britain Search Report dated Feb. 24, 2016 in counterpart Great Britain Application No. GB1507719.7.
Jung et al., "Clinical Validation of Colorectal Cancer Biomarkers Identified from Bioinformatics Analysis of Public Expression Data" Clinical Cancer Research. vol. 17, No. 4: 700-710.
CAS RN 480778-97-0. "C9orf140 protein (human clone Image: 3502019 gene C9orfl40)" STN Chemical Abstract Registry. GenBank (Jan. 23, 2003) p. 1.
Weng et al., "Role of C9orfl140 in the promotion of colorectal cancer progression and mechanisms of its upregulation via activation of STAT5, B-catenin and EZH2" Carcinogenesis. (2014) vol. 35, No. 6: 1389-1398.
International Search Report for PCT/EP2016/060007, dated Sep. 19, 2016.
Weinschenk et al., "Integrated functional genomics approach for the design of patient-individual antitumor vaccines." Cancer Research, American Association for Cancer Research, US. vol. 62, No. 20, Oct. 15, 2002, pp. 5818-5827. XP002266492, 21-29. ISSN: 0008-5472.
DATABASE Uni Prot [Online] 1-4,7, Dec. 1, 2001, XP002759848. Retrieved from EBI accession No. Uni Prot: Q96GJ3. Database accession No. Q96GJ3.

* cited by examiner

*Primary Examiner* — Karen A. Canella
(74) *Attorney, Agent, or Firm* — McBee Moore Woodward & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T-cells ex vivo and transfer into patients. Peptides bound to molecules of the major histocompatibility complex (MHC), or peptides as such, can also be targets of antibodies, soluble T-cell receptors, and other binding molecules.

18 Claims, 20 Drawing Sheets
(1 of 20 Drawing Sheet(s) Filed in Color)
Specification includes a Sequence Listing.

Peptide: ALIKQLFEA (A*02) SEQ ID NO: 1

Peptide: KQFEGTVEI (A*02) – SEQ ID NO: 138

Peptide: KLAVALLAA (A*02) – SEQ ID NO: 210

Peptide: LLYGKYVSV (A*02) – SEQ ID NO: 31

Peptide detected on
3 pancreatic cell lines, 3 skin cell lines, 1 leucocytic cell line, 0 normal tissues, 28 cancer tissues (2 brain cancers, 1 breast cancer, 1 colon cancer, 1 esophageal cancer, 2 kidney cancers, 1 leukemia, 5 liver cancers, 7 lung cancers, 5 ovarian cancers, 1 prostate cancer, 2 rectal cancers) (from left to right)

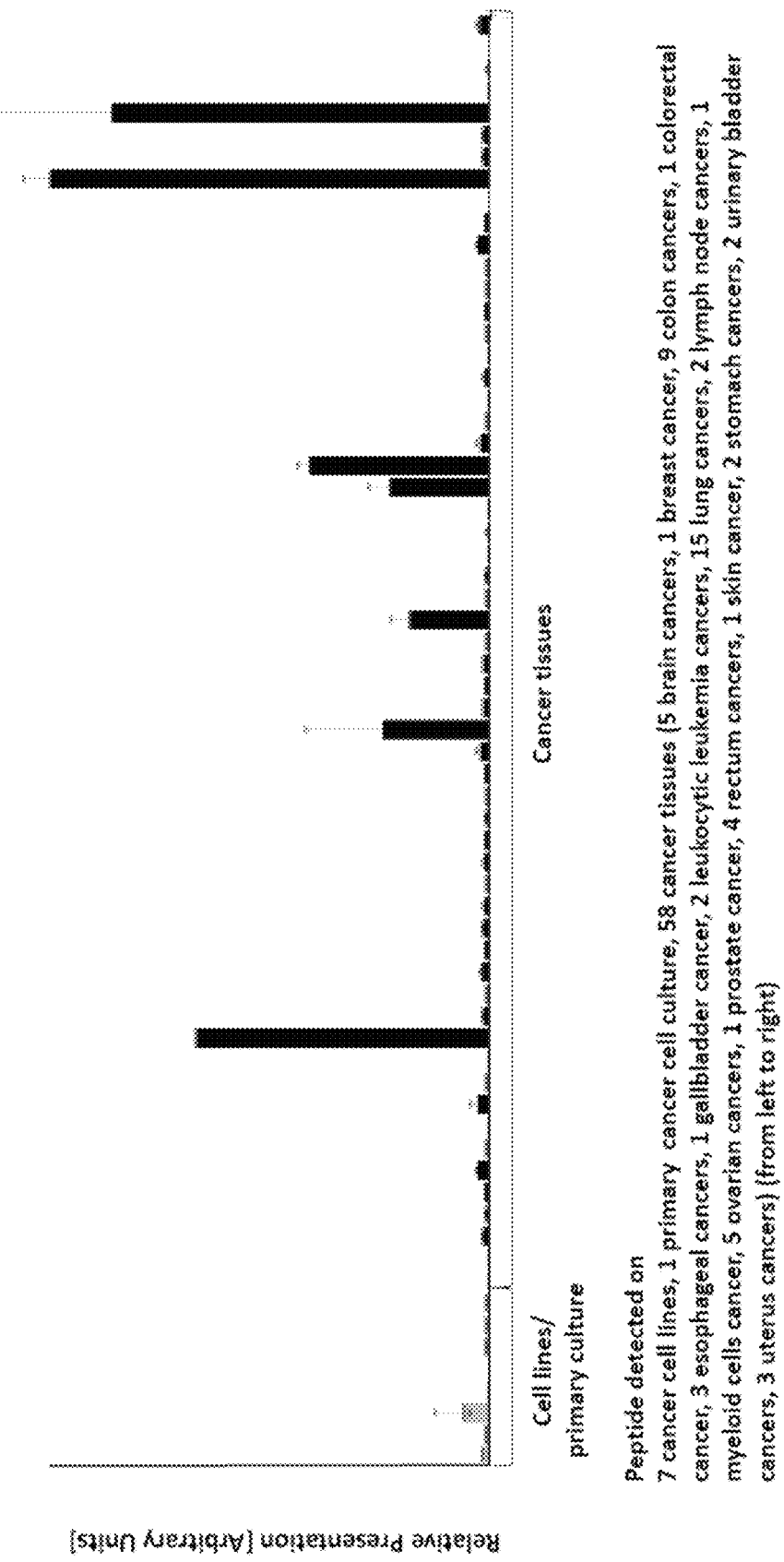

Peptide: FLAELPGSLSL (A*02)
SEQ ID NO: 6

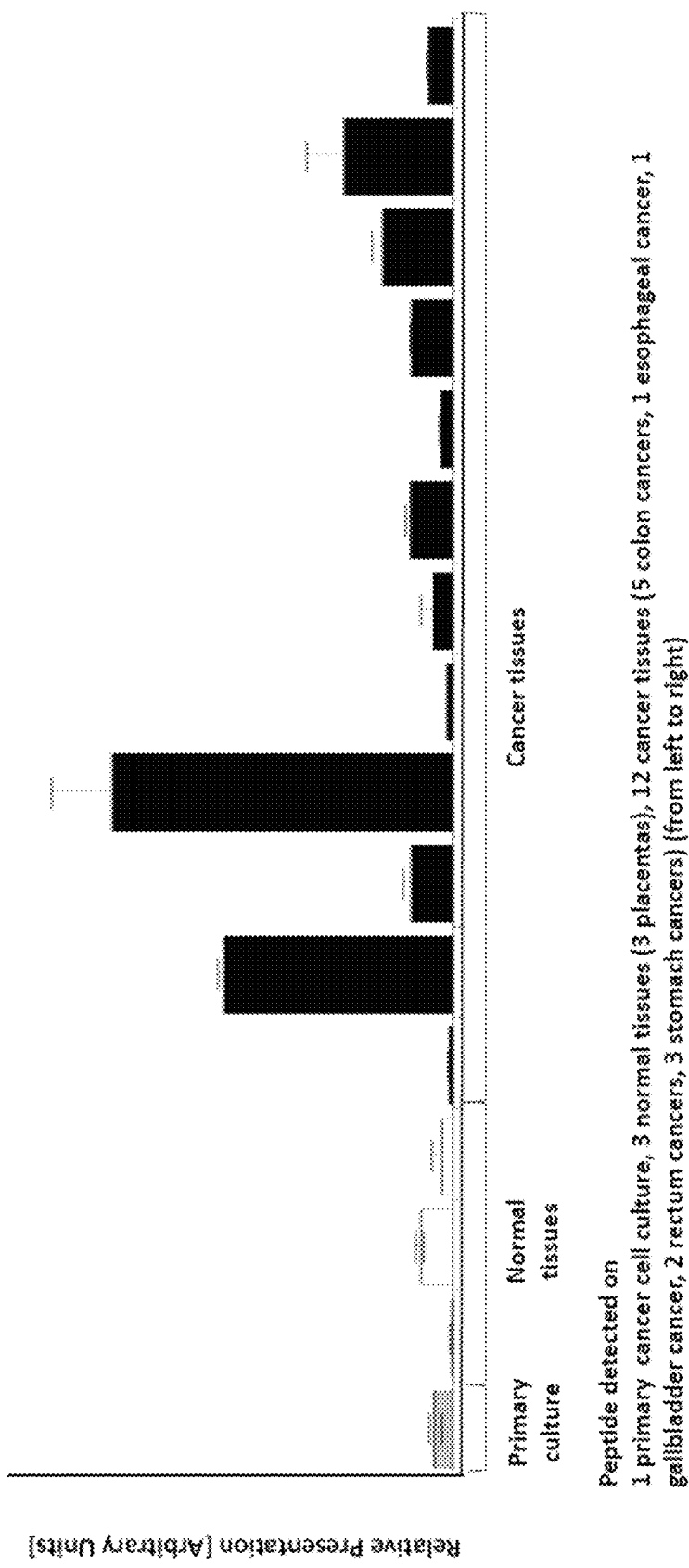

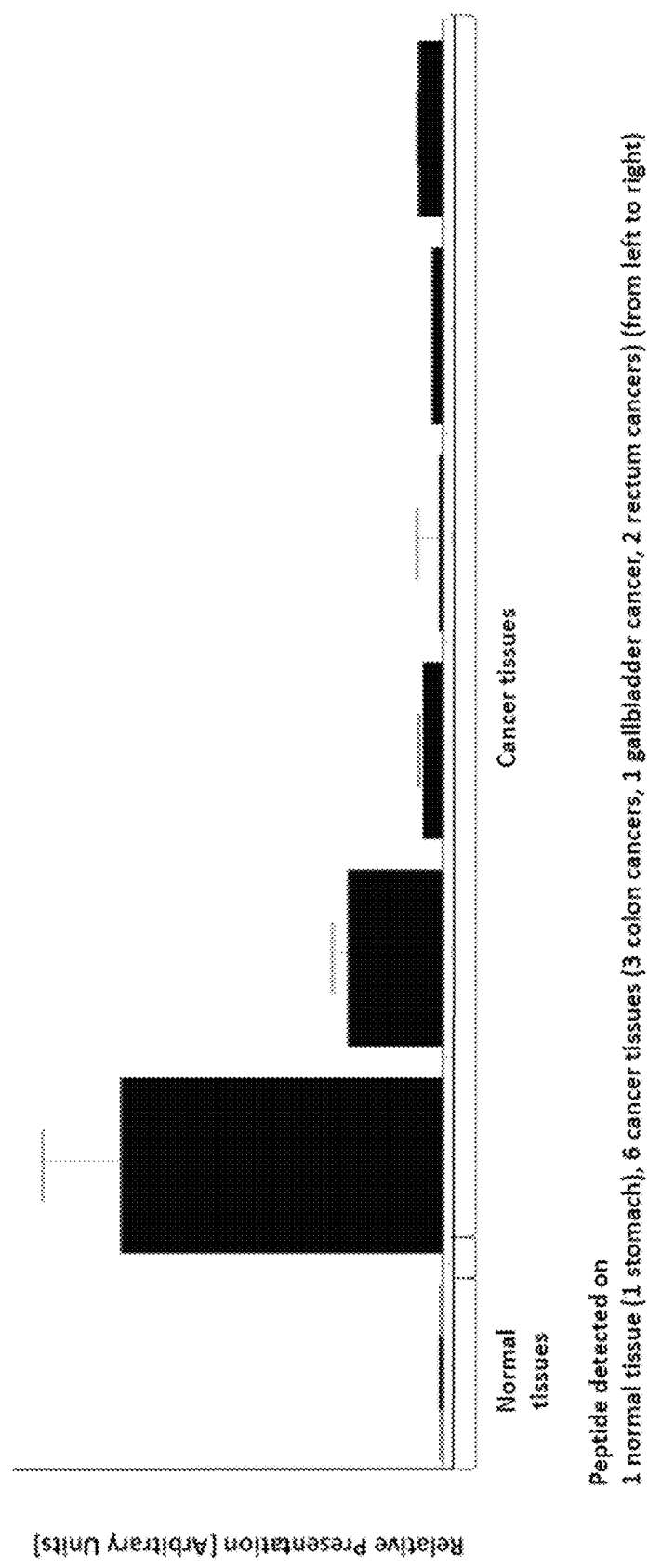

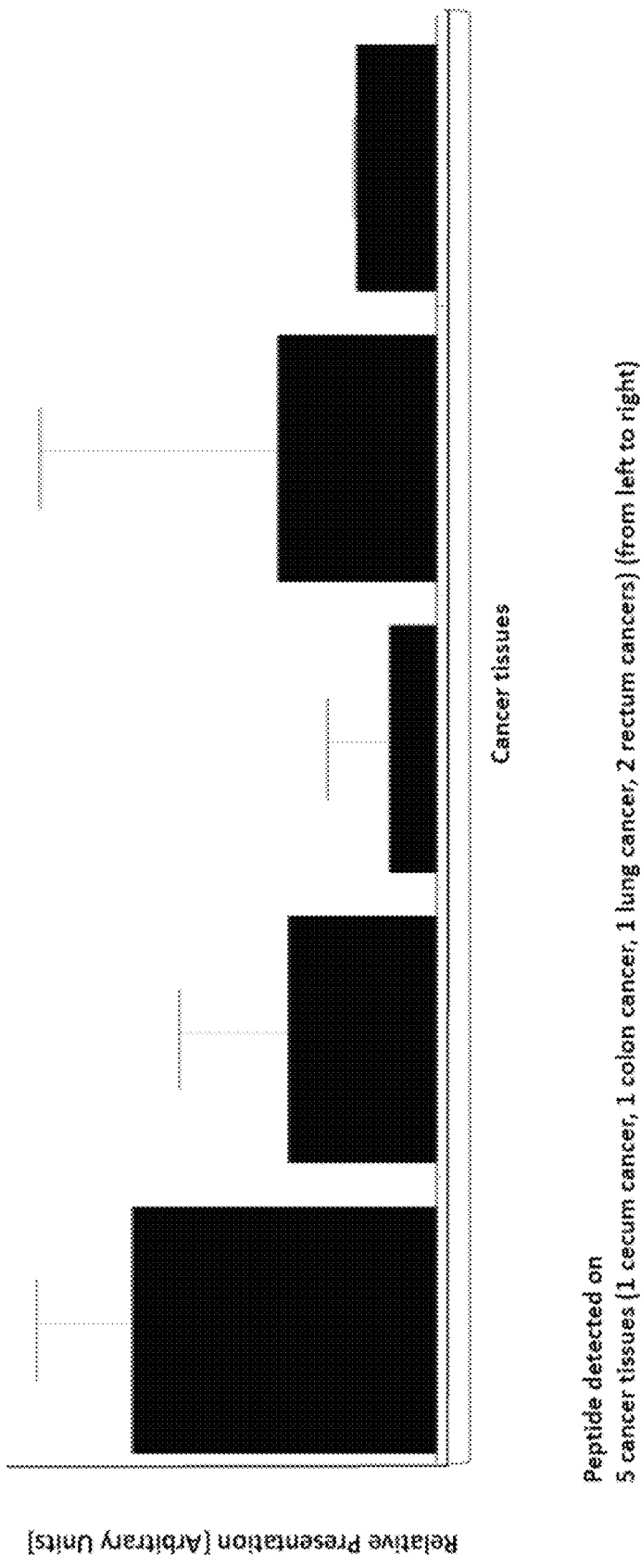

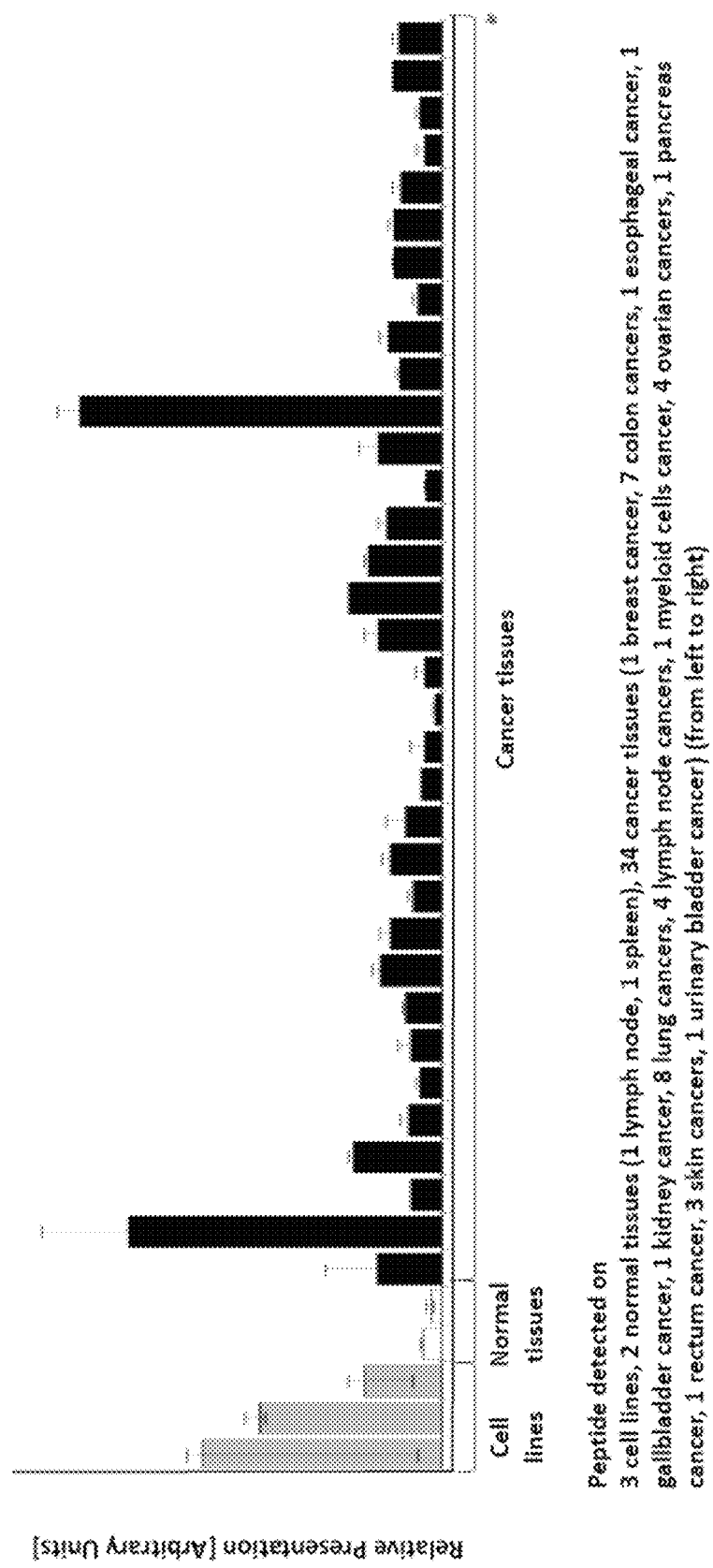

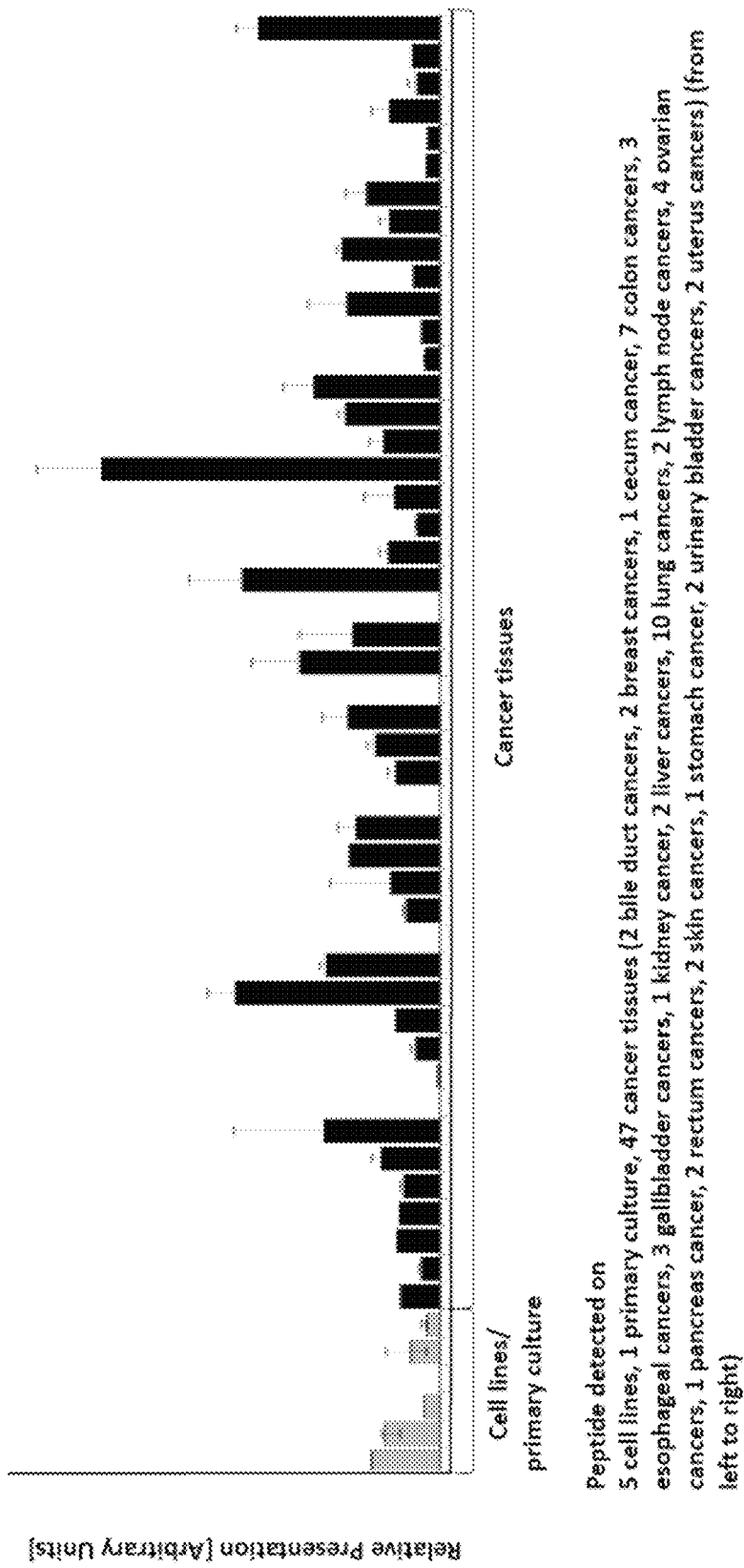

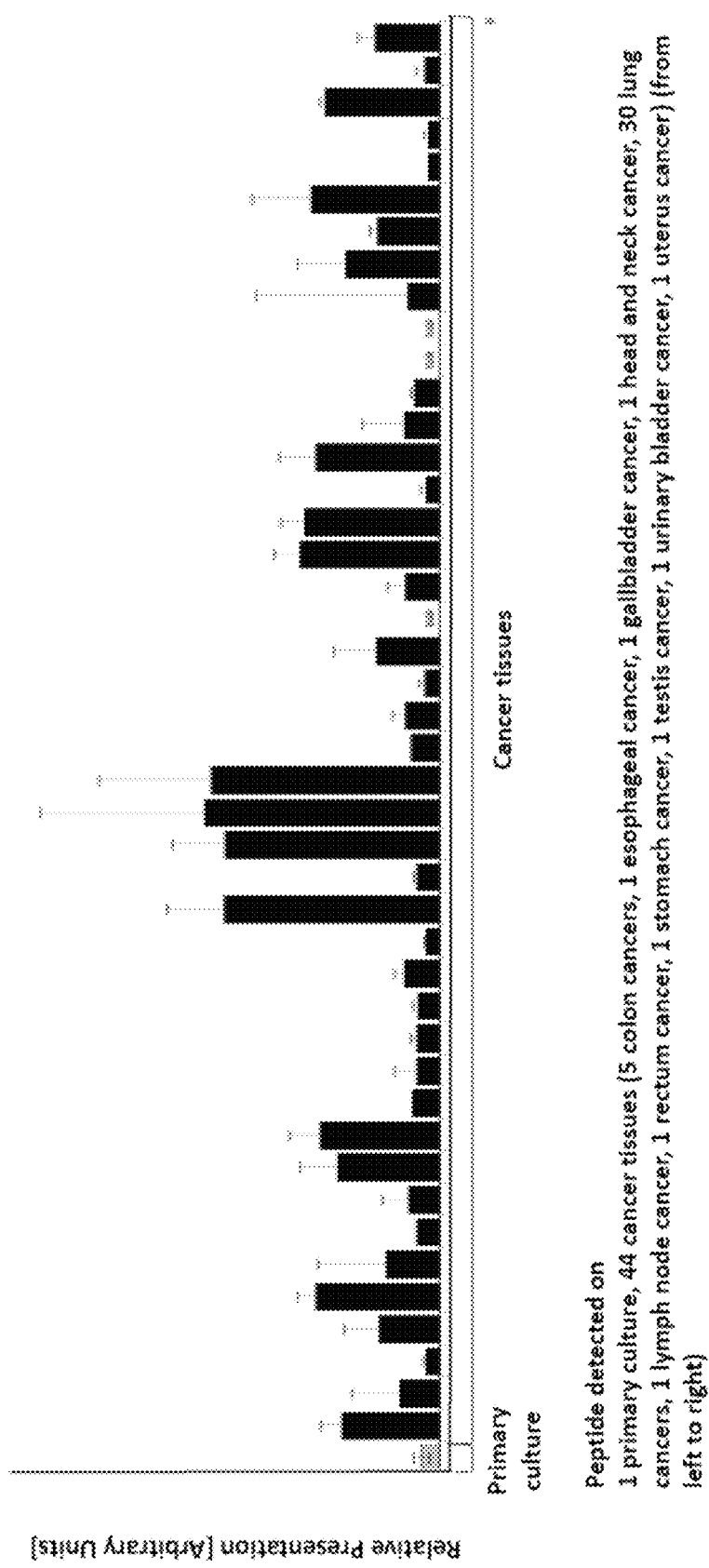

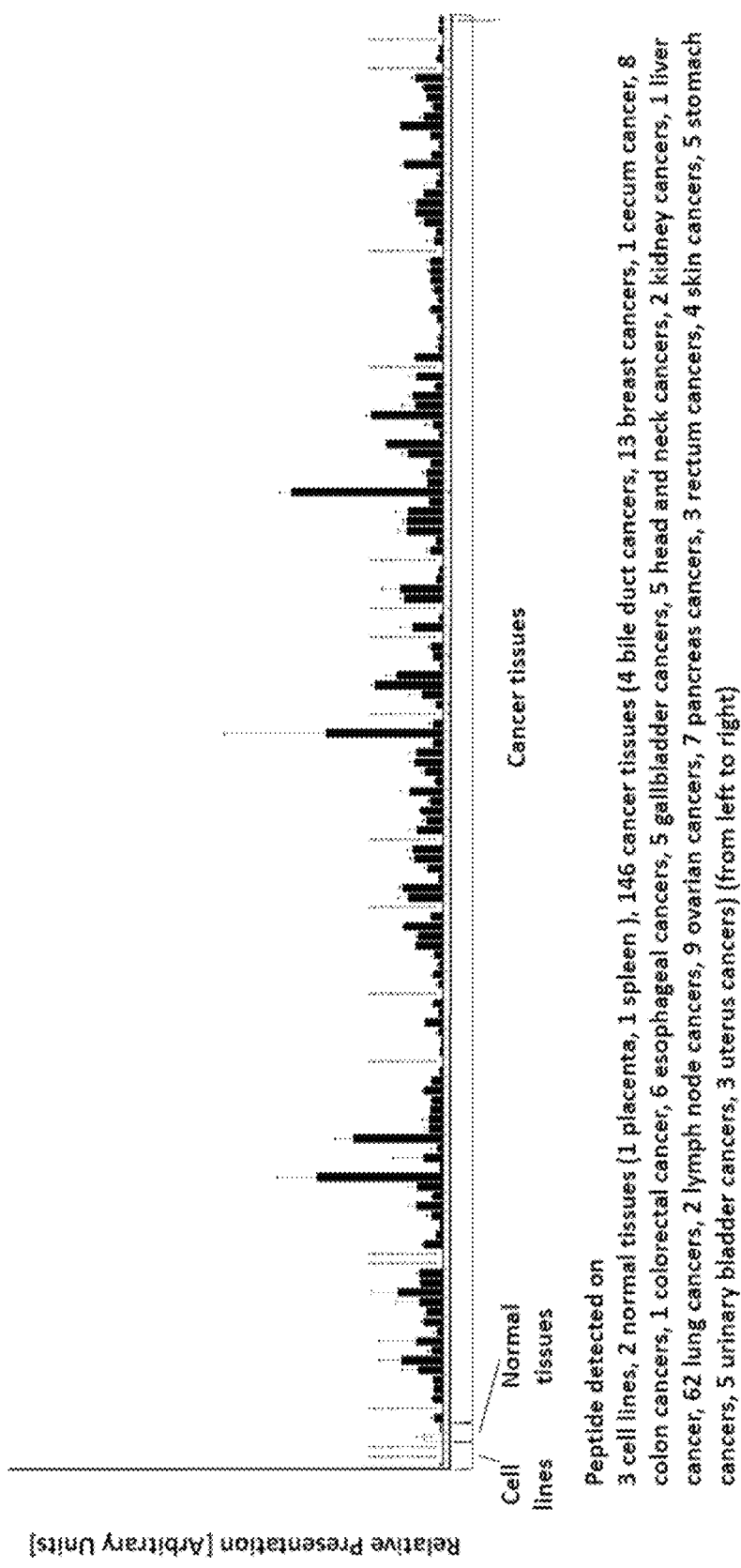

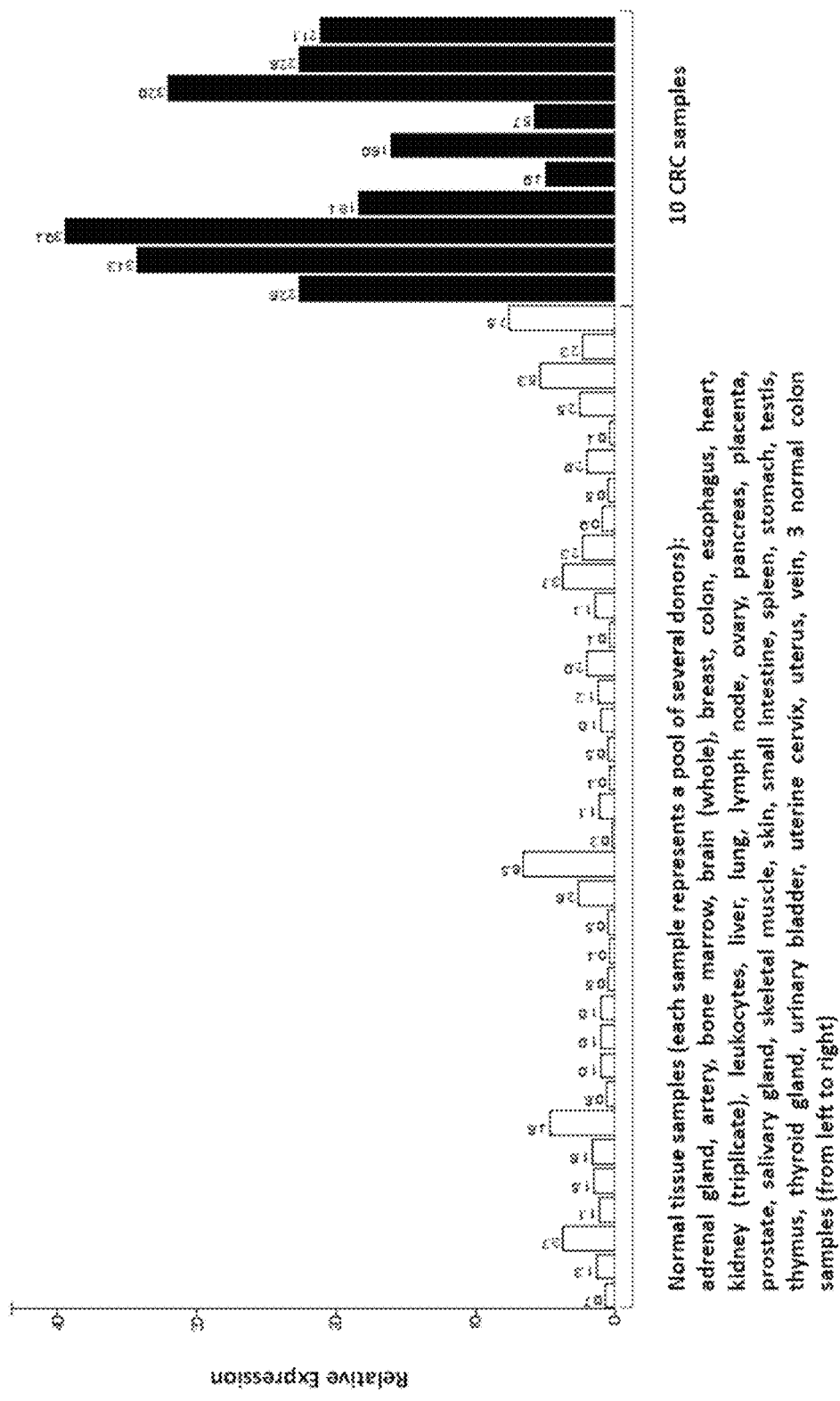

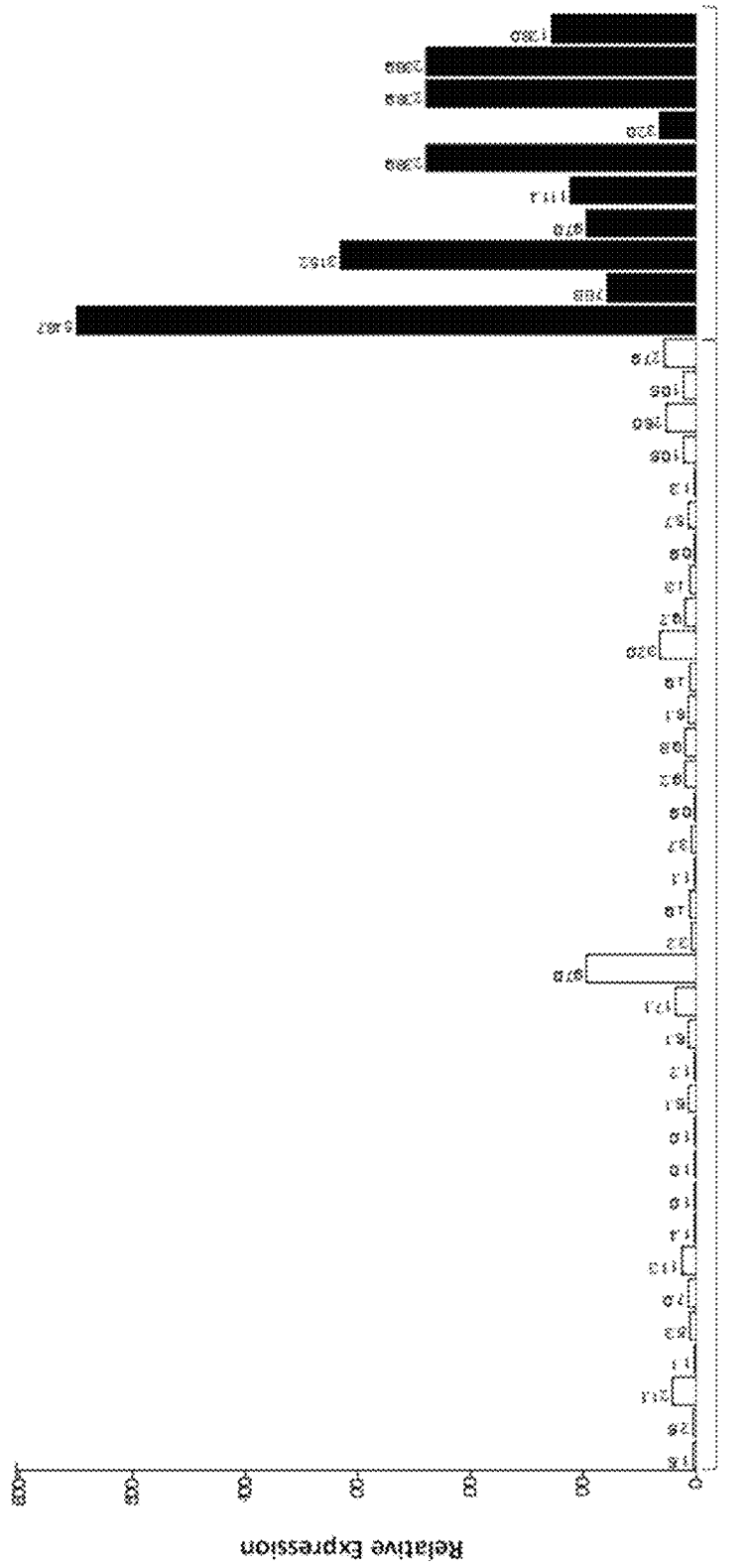

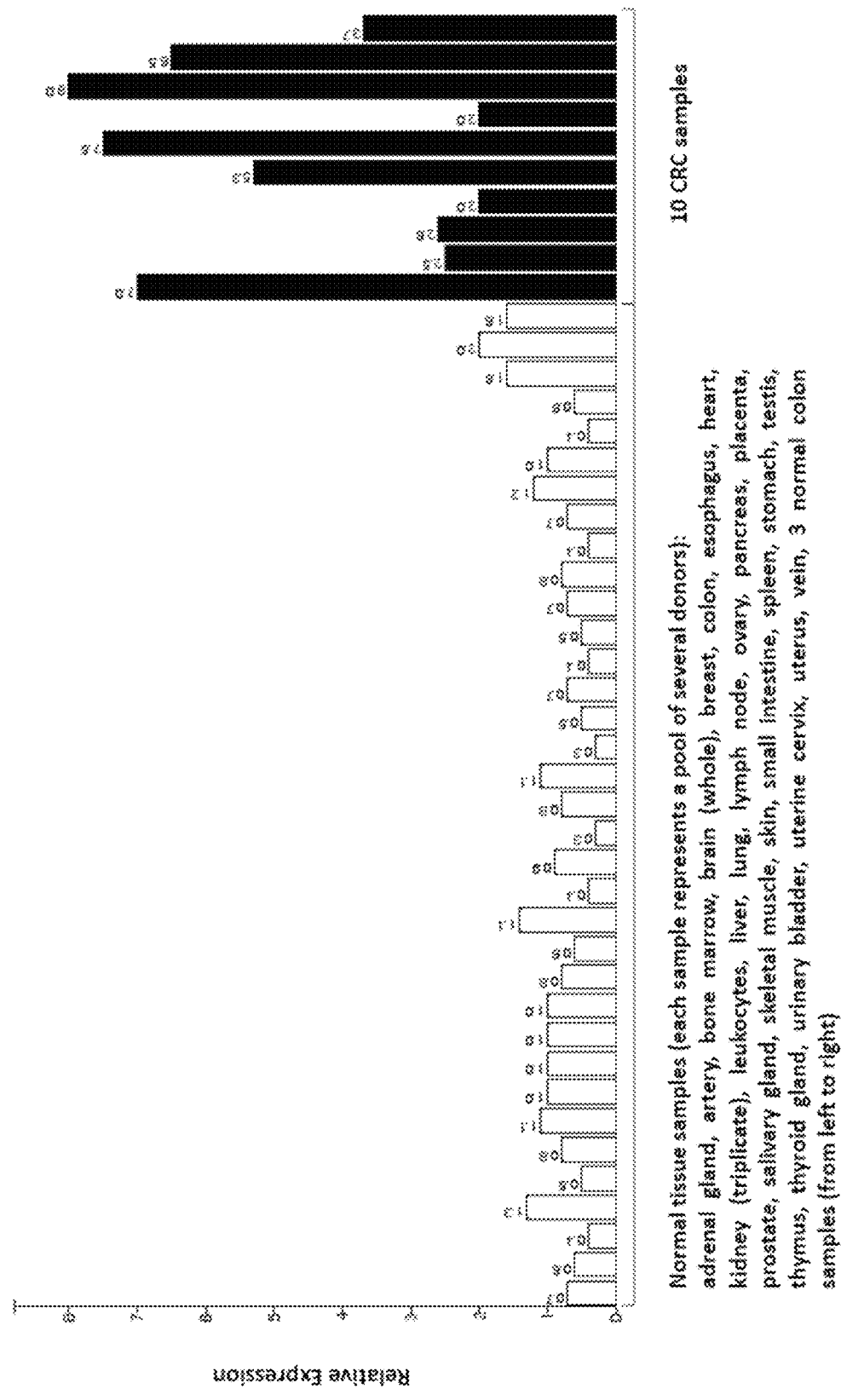

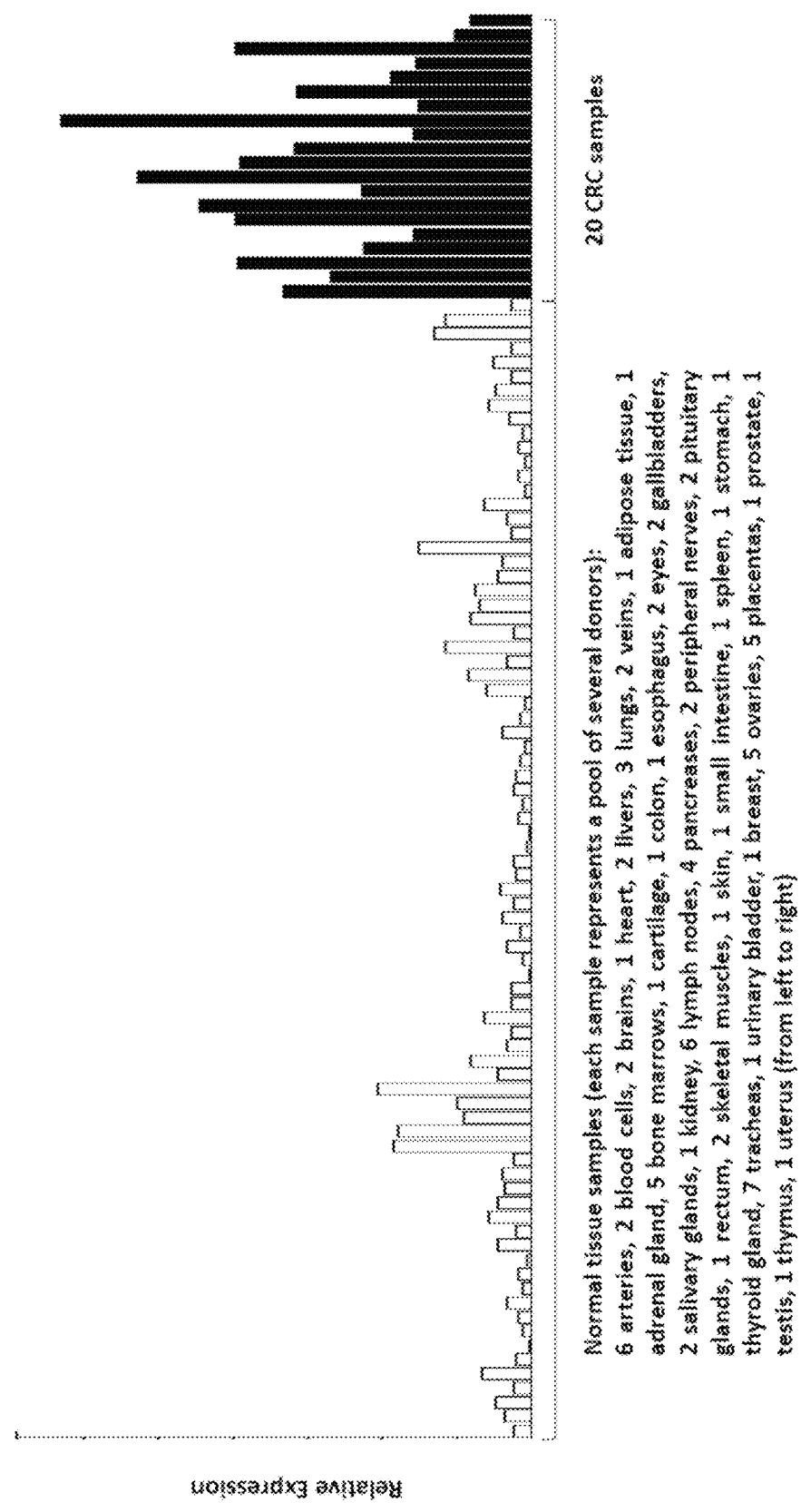

PEPTIDES AND COMBINATION OF PEPTIDES AND SCAFFOLDS THEREOF FOR USE IN IMMUNOTHERAPY AGAINST COLORECTAL CARCINOMA (CRC) AND OTHER CANCERS

CROSS-REFERENCE TO RELATED APPLICATIONS

This application is continuation of U.S. patent application Ser. No. 15/145,990, filed 4 May 2016, which claims priority to U.S. Provisional Application No. 62/157,684, filed 6 May 2015, and British Patent Application No. 1507719.1, filed 6 May 2015. The disclosure of each of the priority applications is incorporated in its entirety herein by reference.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-046005_ST25.txt" created on 10 May 2018, and 42,044 bytes in size) is submitted concurrently with the instant application, and the entire contents of the Sequence Listing are incorporated herein by reference.

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T-cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

BACKGROUND OF THE INVENTION

Colorectal cancer (CRC) is the third most common cancer in men and the second most common cancer in women. Globally, CRC accounts for about 10% of all newly diagnosed cancer cases. In 2012, 1.36 million new CRC cases were diagnosed with 746,000 cases in men and 614,000 cases in women, resulting in a male:female ratio of 1.2:1 (World Cancer Report, 2014). CRC is a disease of the elderly. The mean age at the time of diagnosis is 68 years (SEER Stat facts, 2014).

Incidence rates vary geographically about ten-fold with similarities in men and women. The highest incidence rates in both sexes occur in Australia/New Zealand (age-standardized rate (ASR)=45 per 100,000 men and ASR=32 per 100,000 women). Incidence rates in Europe show small regional variation and ASR=38 per 100,000 men and ASR=25 per 100,000 women. The lowest incidence rates in the world occur in Western Africa with 4.5 per 100,000 men and 3.8 per 100,000 women (World Cancer Report, 2014).

The overall 5-year survival rate from CRC is about 65%. However, survival rates depend on stage at the time point of diagnosis. The 5-year survival for localized CRC is 89.8%, for regional and distant CRC 70.5% and 12.9%, respectively. CRC is the fourth highest cause of cancer death (694,000 deaths; 8.5%) (SEER Stat facts, 2014; World Cancer Report, 2014).

CRC is usually staged using the TNM system, which incorporates information about the size of the primary tumor (T), the involvement of lymph nodes (N) and the occurrence of distant metastases (M). The UICC (Union Internationale Contre le Cancer) staging is based on the TNM system and includes statistical data for prognosis prediction (Stintzing, 2014).

Risk factors for developing CRC include lifestyle factors, hereditary disposition and inflammatory conditions. Excessive alcohol use, cigarette smoking and obesity are associated with an elevated risk to develop CRC. Hereditary risk factors are familial occurrence of CRC, familial adenomatous polyposis (FAP), attenuated FAP (AFAP)/attenuated adenomatous polyposis coli (AAPC), hereditary non-polyposis colorectal carcinoma (HNPCC) and hamartomatous polyposis syndromes. Inflammatory conditions associated with an increased CRC risk include inflammatory bowel diseases (IBD) such as ulcerative colitis and Crohn's disease (Baena and Salinas, 2015; Stintzing, 2014; Vasen et al., 2015).

Histologically, more than 90% of all CRC are adenocarcinomas. Rare CRC types include neuroendocrine, squamous cell, adenosquamous, spindle cell and undifferentiated carcinomas (Fleming et al., 2012). The majority of colorectal adenocarcinomas derive from adenoma or dysplasia precursor lesions. Depending on the type of the lesions/carcinomas, different molecular mechanisms contribute to tumorigenesis. The chromosomal instability (CIN) pathway ("suppressor" pathway) is characterized by mutations in the APC, KRAS or p53 genes. Additional mutations are found in the LKB1/STK11, SMAD4, BMPR1A or MYH genes. The microsatellite instability (MSI) pathway ("mutator" pathway) comprises mutations in the DNA mismatch repair (MMR) genes MLH1, MSH2, MSH6 and PMS2, MMR gene hypermethylation or BRAF mutations. Epigenetic instability, including DNA methylation, histone alteration and chromatin remodeling, is characteristic for CIMP (CpG island mathylator phenotype) tumors (Fleming et al., 2012).

Depending on the CRC stage, different standard therapies are available for colon and rectal cancer. Standard procedures include surgery, radiation therapy, chemotherapy and targeted therapy for CRC (Berman et al., 2015a; Berman et al., 2015b).

Removal of the tumor is essential for the treatment of CRC. Anatomic conditions differ for rectal carcinomas from other CRC as the rectum is located in the pelvis and the tumor can be difficult to access. Well-differentiated small rectal tumors (stage T1) require excision, but no further treatment with chemotherapy. Patients with rectal tumors of higher T stages receive neoadjuvant radio-chemotherapy with a fluoropyrimidine prior to total mesorectal excision (TME) and adjuvant chemotherapy. For chemotherapeutic treatment the drugs capecitabine or 5-fluorouracil (5-FU) are used. For combinational chemotherapy a cocktail containing 5-FU, leucovorin and oxaliplatin (FOLFOX) is recommended (Stintzing, 2014; Berman et al., 2015b).

Treatment of colon carcinomas involves radical hemicolectomy and lymph node resection. Early stages (UICC stage I) do not require additional treatment. Patients with tumors of UICC stage II receive 5-FU or capecitabine. Treatment for patients with UICC stage III includes the drug combinations FOLFOX and XELOX (capecitabine plus oxaliplatin) (Berman et al., 2015a; Stintzing, 2014).

Metastatic, unresectable CRC are treated with chemotherapeutical cocktails such as FOLFIRI (5-FU, leucovorin, irinotecan), FOLFOX, FOLFOXIRI (5-FU, irinotecan, oxaliplatin), FOLFOX/capecitabine, FOLFOX/oxaliplatin, FOLFIRI/capecitabine and irinotecan or UFT (5-FU, tegafur-uracil) (Stintzing, 2014).

In addition to chemotherapeutic drugs, several monoclonal antibodies targeting the epidermal growth factor receptor (EGFR, cetuximab, panitumumab) or the vascular endothelial growth factor-A (VEGF-A, bevacizumab) are administered to patients with high stage disease. For second-line and later treatment the inhibitor for VEGF aflibercept, the tyrosine kinase inhibitor regorafenib and the thymidylate-synthetase inhibitor TAS-102 and the dUTPase inhibitor TAS-114 can be used (Stintzing, 2014; Wilson et al., 2014).

Latest clinical trials analyze active immunotherapy as a treatment option against CRC. Those strategies include the vaccination with peptides from tumor-associated antigens (TAAs), whole tumor cells, dendritic cell (DC) vaccines and viral vectors (Koido et al., 2013).

Peptide vaccines have so far been directed against carcinoembryonic antigen (CEA), mucin 1, EGFR, squamous cell carcinoma antigen recognized by T-cells 3 (SART3), beta-human chorionic gonadotropin (beta-hCG), Wilms' Tumor antigen 1 (WT1), Survivin-2B, MAGE3, p53, ring finger protein 43 and translocase of the outer mitochondrial membrane 34 (TOMM34), or mutated KRAS. In several phase I and II clinical trials patients showed antigen-specific CTL responses or antibody production. In contrast to immunological responses, many patients did not benefit from peptide vaccines on the clinical level (Koido et al., 2013; Miyagi et al., 2001; Moulton et al., 2002; Okuno et al., 2011).

Dendritic cell vaccines comprise DCs pulsed with either TAA-derived peptides, tumor cell lysates, apoptotic tumor cells, or tumor RNA or DC-tumor cell fusion products. While many patients in phase I/II trials showed specific immunological responses, only the minority had a clinical benefit (Koido et al., 2013).

Whole tumor cell vaccines consist of autologous tumor cells modified to secrete GM-CSF, modified by irradiation or virus-infected, irradiated cells. Most patients showed no clinical benefit in several phase II/Ill trials (Koido et al., 2013).

Vaccinia virus or replication-defective avian poxvirus encoding CEA as well as B7.1, ICAM-1 and LFA-3 have been used as vehicles in viral vector vaccines in phase I clinical trials. A different study used nonreplicating canarypox virus encoding CEA and B7.1. Besides the induction of CEA-specific T-cell responses 40% of patients showed objective clinical responses (Horig et al., 2000; Kaufman et al., 2008).

Considering the severe side-effects and expense associated with treating cancer, there is a need to identify factors that can be used in the treatment of cancer in general and CRC in particular. There is also a need to identify factors representing biomarkers for cancer in general and CRC in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:

a) Cancer-testis antigens: The first TAAs ever identified that can be recognized by T-cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T-cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T-cells bearing the appropriate T-cell receptor (TCR), whereas complexes of peptide and MHC class II molecules are recognized by CD4-positive-helper-T-cells bearing the appropriate TCR. It is well known that the TCR, the peptide and the MHC are thereby present in a stoichiometric amount of 1:1:1.

CD4-positive helper T-cells play an important role in inducing and sustaining effective responses by CD8-positive cytotoxic T-cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T-cell- (CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated (longer) peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T-cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T-cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T-cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T-cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-1-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T-cells bearing specific T-cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T-cell having a corresponding TCR and the absence of immunological tolerance for this particular epitope.

Therefore, TAAs are a starting point for the development of a T-cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T-cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T-cell can be found. Such a functional T-cell is defined as a T-cell, which upon stimulation with a specific antigen can be clonally expanded and is able to execute effector functions ("effector T-cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect of the present invention, the present invention relates to a peptide comprising an amino acid sequence selected from the group consisting of SEQ ID NO: 1 to SEQ ID NO: 191 or a variant sequence thereof which is at least 77%, preferably at least 88%, homologous (preferably at least 77% or at least 88% identical) to SEQ ID NO: 1 to SEQ ID NO: 191, wherein said variant binds to MHC and/or induces T-cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 191 or a variant thereof, which is at least 77%, preferably at least 88%, homologous (preferably at least 77% or at least 88% identical) to SEQ ID NO: 1 to SEQ ID NO: 191, wherein said peptide or variant thereof has an overall length of between 8 and 100, preferably between 8 and 30, and most preferred of between 8 and 14 amino acids.

The following tables show the peptides according to the present invention, their respective SEQ ID NOs, and the prospective source (underlying) genes for these peptides. All peptides in Table 1 and Table 2 bind to HLA-A*02. The peptides in Table 2 have been disclosed before in large listings as results of high-throughput screenings with high error rates or calculated using algorithms, but have not been associated with cancer at all before. The peptides in Table 3 are additional peptides that may be useful in combination with the other peptides of the invention. The peptides in Table 4A and B are furthermore useful in the diagnosis and/or treatment of various other malignancies that involve an over-expression or over-presentation of the respective underlying polypeptide.

TABLE 1

Peptides according to the present invention

| SEQ ID No. | Sequence | GeneID(s) | Official Gene Symbol(s) |
| --- | --- | --- | --- |
| 1 | ALIKQLFEA | 168417, 441234, 89958 | ZNF679, ZNF716, SAPCD2 |
| 2 | ALLPRYFFL | 23120 | ATP10B |
| 3 | RLIPDTLYSV | 1303 | COL12A1 |
| 4 | RLAELTVDEFL | 26155, 401010 | NOC2L, LOC401010 |
| 5 | WLFDDGGLTL | 6557, 6558, 6559 | SLC12A1, SLC12A2, SLC12A3 |
| 6 | FLAELPGSLSL | 5326 | PLAGL2 |
| 7 | YLTRHLAVL | 4583 | MUC2 |
| 8 | ALMLQGVDLL | 3329 | HSPD1 |
| 9 | ILDDHLSRV | 8313 | AXIN2 |
| 10 | RMYNKIFAI | 80201 | HKDC1 |
| 11 | YLFEKTFNM | 90161 | HS6ST2 |
| 12 | ALVQGILERV | 4843 | NOS2 |
| 13 | FLLAEDTKV | 10592 | SMC2 |
| 14 | FLDKPEDVLL | 2036 | EPB41L1 |
| 15 | LQLDKEFQL | 24140 | FTSJ1 |
| 16 | VLVDQSWVL | 5655 | KLK10 |
| 17 | ALAAARVEL | 6558 | SLC12A2 |
| 18 | FLSSLKGGLL | 83608 | C18orf21 |
| 19 | RLYTKLLNEA | 4651 | MYO10 |
| 20 | YLKDGDVML | 11180 | WDR6 |
| 21 | VLIDHRWVL | 43849 | KLK12 |
| 22 | GLIDEVMVL | 54905 | CYP2W1 |
| 23 | FLDANGHFV | 54905 | CYP2W1 |
| 24 | VLDGVLMEL | 4190 | MDH1 |
| 25 | SLADRLIGV | 57535 | KIAA1324 |
| 26 | GLASKENFSNVSL | 6840 | SVIL |
| 27 | LLADEDSSYL | 51510 | CHMP5 |
| 28 | ALTEIQEFI | 5591 | PRKDC |
| 29 | QMLDVAIRV | 8943 | AP3D1 |
| 30 | GLSSAYGGL | 10787, 3856, 728638 | NCKAP1, KRT8, KRT8P3 |
| 31 | LLYGKYVSV | 84065 | TMEM222 |
| 32 | KLNTETFGV | 149986 | LSM14B |
| 33 | ALWEKNTHL | 11190 | CEP250 |
| 34 | ILLEKSVSV | 80728 | ARHGAP39 |
| 35 | KLLDLTVRI | 10562 | OLFM4 |
| 36 | GLLESPSIFNFTA | 23185 | LARP4B |

TABLE 1-continued

Peptides according to the present invention

| SEQ ID No. | Sequence | GeneID(s) | Official Gene Symbol(s) |
|---|---|---|---|
| 37 | GLFAGLGGAGA | 10916 | MAGED2 |
| 38 | SLAPTPVSA | 8870 | IER3 |
| 39 | GLNGGSPAAA | 1045 | CDX2 |
| 40 | ALSNVIHKV | 5268 | SERPINB5 |
| 41 | ILDDSFKLL | 9843 | HEPH |
| 42 | SILDDSFKL | 9843 | HEPH |
| 43 | TLDAAQPRV | 6649 | SOD3 |
| 44 | SLESKLTSV | 9289 | GPR56 |
| 45 | ALAELLHGA | 26470 | SEZ6L2 |
| 46 | GLDDRYSLV | 11187 | PKP3 |
| 47 | KLYERCEVV | 2065 | ERBB3 |
| 48 | FLDASDPAL | 65266 | WNK4 |
| 49 | SGMGGITAV | 3856 | KRT8 |
| 50 | TLMAEMHVV | 2186 | BPTF |
| 51 | QVWEIQHTV | 26290 | GALNT8 |
| 52 | ALDSSNSMQTI | 3875 | KRT18 |
| 53 | FLLGSEIKL | 54885 | TBC1D8B |
| 54 | ALLNGEYLLAA | 57418 | WDR18 |
| 55 | QIITSVVSV | 5378 | PMS1 |
| 56 | VLFTDEGVPKFL | 4731 | NDUFV3 |
| 57 | NLLEKENYL | 5318 | PKP2 |
| 58 | AMADKMDMSL | 10189 | ALYREF |
| 59 | LLTDNVVKL | 79810 | PTCD2 |
| 60 | VLDEDEPRFL | 23287 | AGTPBP1 |
| 61 | KLLKLFQGV | 26058 | GIGYF2 |
| 62 | YLAPENGYL | 6625 | SNRNP70 |
| 63 | KLFSILSTV | 54919 | HEATR2 |
| 64 | KTLGKLWRL | 30812, 6662, 6663 | SOX8, SOX9, SOX10 |
| 65 | FGAPGIISA | 5725 | PTBP1 |
| 66 | GLDDGPDFL | 58533 | SNX6 |
| 67 | SLNDLEKDVMLL | 6597 | SMARCA4 |
| 68 | SILQFVHMV | 5800 | PTPRO |
| 69 | GMLNEAEGKAIKL | 4629 | MYH11 |
| 70 | MISELEVRL | 4629 | MYH11 |
| 71 | RLWTEIPTAI | 3710 | ITPR3 |
| 72 | YLLDYPNNLL | 26057 | ANKRD17 |
| 73 | YLFDIAVSM | 51074 | APIP |
| 74 | YLMGFLHAV | 23779, 553158, 55615 | ARHGAP8, PRR5-ARHGAP8, PRR5 |
| 75 | EMIENIQSV | 1080 | CFTR |
| 76 | YLIGEKQHYL | 7429 | VIL1 |
| 77 | SLLKRDFGA | 1655 | DDX5 |
| 78 | ALDPELLLL | 57805 | KIAA1967 |
| 79 | SLAADQLLKL | 9295 | SRSF11 |
| 80 | QVDEVVDIMRV | 3604, 6844, 9341 | TNFRSF9, VAMP2, VAMP3 |
| 81 | ALLSQQTHL | 7050 | TGIF1 |
| 82 | QLYEEPDTKL | 10270 | AKAP8 |
| 83 | LTIEDGIFEV | 3306, 3312, 100287551 | HSPA2, HSPA8, HSPA8P8 |
| 84 | SMVEDITGLRL | 1832 | DSP |
| 85 | ILHDINSDGVL | 4924 | NUCB1 |
| 86 | KVFPGKISV | 56667 | MUC13 |
| 87 | LLFDAPDLRL | 55561 | CDC42BPG |
| 88 | KLDIKVETV | 55243 | KIRREL |
| 89 | SLIEYEFRV | 3655 | ITGA6 |
| 90 | GLLKPGLNVVL | 10969 | EBNA1BP2 |
| 91 | TVDVATPSV | 8924 | HERC2 |
| 92 | WIDDTSAFV | 5073 | PARN |
| 93 | SLQELRLLL | 55502 | HES6 |
| 94 | KSMDIVLTV | 4586, 727897 | MUC5AC, MUC5B |
| 95 | AILDAHIEV | 26290 | GALNT8 |
| 96 | KLYSRLVYV | 387496 | RASL11A |
| 97 | ALWWGVVTV | 3784 | KCNQ1 |
| 98 | AMNGKSFSV | 79572 | ATP13A3 |
| 99 | KLLEVDLDTV | 4648 | MYO7B |
| 100 | SLDDFLATA | 55341 | LSG1 |
| 101 | GLSEGHTFQV | 2318 | FLNC |
| 102 | KILVSLIEV | 10422 | UBAC1 |
| 103 | FLFGYPKRL | 64110 | MAGEF1 |
| 104 | ILLTIKDDTIYL | 4583 | MUC2 |
| 105 | YALDLSTFL | 8870 | IER3 |
| 106 | SLISEKILL | 26504 | CNNM4 |
| 107 | ALLGGGPYML | 80004 | ESRP2 |
| 108 | SLAELVPGVGGI | 9742 | IFT140 |
| 109 | ALDGDQMEL | 3192 | HNRNPU |

TABLE 1-continued

Peptides according to the present invention

| SEQ ID No. | Sequence | GeneID(s) | Official Gene Symbol(s) |
|---|---|---|---|
| 110 | LLGELPRLLLL | 1604 | CD55 |
| 111 | HMDDGGYSM | 27316, 494115 | RBMX, RBMXL1 |
| 112 | KLGQVLIYL | 51809 | GALNT7 |
| 113 | ILYDLQQNL | 3783 | KCNN4 |
| 114 | TAVGHALVL | 1293 | COL6A3 |
| 115 | SLFDVSHML | 275 | AMT |
| 116 | LVYQFVHPI | 25803 | SPDEF |
| 117 | TLQPVDNSTISL | 1266 | CNN3 |
| 118 | LLADLKTMV | 5141, 5142, 5143, 5144 | PDE4A, PDE4B, PDE4C, PDE4D |
| 119 | ILYQTVTGL | 83732 | RIOK1 |
| 120 | VLYEGVDEV | 93432 | MGAM2 |
| 121 | SLAPNIISQL | 25824 | PRDX5 |
| 122 | SLMGMVLKL | 11169 | WDHD1 |

TABLE 2

Additional peptides according to the present invention with no prior known cancer association - J = phosphoserine

| SEQ ID No. | Sequence | GeneID(s) | Official Gene Symbol(s) |
|---|---|---|---|
| 123 | KTLERSYLL | 6240 | RRM1 |
| 124 | RVLPPSALQSV | 9212 | AURKB |
| 125 | KLGDFGLLVEL | 9088 | PKMYT1 |
| 126 | TLAKYLMEL | 891, 9133 | CCNB1, CCNB2 |
| 127 | RLAELTVDEFLA | 26155 | NOC2L |
| 128 | MLDDRAYLV | 23511 | NUP188 |
| 129 | VLIDVLKEL | 23019 | CNOT1 |
| 130 | GLGGSQLIDTHL | 23215 | PRRC2C |
| 131 | KLLDVVHPA | 10574 | CCT7 |
| 132 | ALLNAILHSA | 25926 | NOL11 |
| 133 | RTFEKIEEV | 3978 | LIG1 |
| 134 | GVAGGSILKGV | 1968, 255308 | EIF2S3, LOC255308 |
| 135 | KLQEEIPVL | 1062 | CENPE |
| 136 | KLFDIFSQQV | 55737 | VPS35 |
| 137 | QLTEIKPLL | 57446 | NDRG3 |
| 138 | KQFEGTVEI | 675 | BRCA2 |
| 139 | VLLNEILEQV | 64151 | NCAPG |
| 140 | LLNEILEQV | 64151 | NCAPG |
| 141 | AVIEHLERL | 283459 | GATC |
| 142 | SLVQRVETI | 1894 | ECT2 |
| 143 | KLSDVWKEL | 197259 | MLKL |
| 144 | LLNDRIWLA | 90204 | ZSWIM1 |
| 145 | LLLEVVKQV | 65065 | NBEAL1 |
| 146 | ALSDETWGL | 2886 | GRB7 |
| 147 | TLTELRAFL | 8242 | KDM5C |
| 148 | RLLENMTEVV | 23042 | PDXDC1 |
| 149 | YQFDKVGILTL | 8563 | THOC5 |
| 150 | RLADLEALKV | 10535 | RNASEH2A |
| 151 | SAQGSDVSLTACKV | 100507703, 3105 | LOC100507703, HLA-A |
| 152 | KLLAVIHEL | 25788 | RAD54B |
| 153 | ILFSEDSTKLFV | 84916 | CIRH1A |
| 154 | KLPSETIFVGC | 50628 | GEMIN4 |
| 155 | RLLGEEVVRV | 9894 | TELO2 |
| 156 | SLMMTIINL | 7153 | TOP2A |
| 157 | SLIERDLKL | 9875 | URB1 |
| 158 | GLLDPSVFHV | 79050 | NOC4L |
| 159 | VLVDDDGIKVV | 79022 | TMEM106C |
| 160 | KLLEFDQLQL | 8871 | SYNJ2 |
| 161 | FLKNELDNV | 10293 | TRAIP |
| 162 | KLMDYIDEL | 85444 | LRRCC1 |
| 163 | RLLHEVQEL | 10540 | DCTN2 |
| 164 | KMLDEILLQL | 5425 | POLD2 |
| 165 | RLLDFPEAMVL | 23113 | CUL9 |
| 166 | GLLEARGILGL | 990 | CDC6 |
| 167 | SVIDHIHLISV | 10755 | GIPC1 |
| 168 | GLIRFPLMTI | 55643 | BTBD2 |
| 169 | YLAHFIEGL | 64328 | XPO4 |
| 170 | ALAGGITMV | 790 | CAD |
| 171 | RLQETEGMVAV | 10042 | HMGXB4 |
| 172 | LLLDTVTMQV | 22820 | COPG1 |
| 173 | KLGDLMVLL | 57647 | DHX37 |
| 174 | ILLDDNMQIRL | 5261 | PHKG2 |
| 175 | TLLGGKEAQALGV | 94059 | LENG9 |
| 176 | RTLDKVLEV | 9933 | KIAA0020 |

TABLE 2-continued

Additional peptides according to the present invention with no prior known cancer association - J = phosphoserine

| SEQ ID No. | Sequence | GeneID(s) | Official Gene Symbol(s) |
|---|---|---|---|
| 177 | ALLQGAIESV | 25894 | PLEKHG4 |
| 178 | YLFREPATI | 4728 | NDUFS8 |
| 179 | RLLJPLSSA | 125950 | RAVER1 |
| 180 | NLLEIAPHL | 2820 | GPD2 |
| 181 | NLFDLGGQYLRV | 22827 | PUF60 |
| 182 | SLNKWIFTV | 339665 | SLC35E4 |
| 183 | TLQEVVTGV | 55750 | AGK |
| 184 | SLLDENNVSSYL | 5591 | PRKDC |
| 185 | VLYTGVVRV | 64682 | ANAPC1 |
| 186 | KMSEKILLL | 5690 | PSMB2 |
| 187 | GLHNVVYGI | 23019 | CNOT1 |
| 188 | FLVDGPRVQL | 90204 | ZSWIM1 |
| 189 | AISEVIGKITA | 9183 | ZW10 |
| 190 | AMAEMVLQV | 9918 | NCAPD2 |
| 191 | QLFSEIHNL | 55755 | CDK5RAP2 |

TABLE 3

Peptides useful for e.g. personalized cancer therapies - J = phosphoserine

| SEQ ID No. | Sequence | GeneID(s) | Official Gene Symbol(s) |
|---|---|---|---|
| 192 | KIQEMQHFL | 4321 | MMP12 |
| 193 | KLSPTVVGL | 8313 | AXIN2 |
| 194 | SLYKGLLSV | 25788 | RAD54B |
| 195 | LLLGERVAL | 23475 | QPRT |
| 196 | KIQEILTQV | 10643 | IGF2BP3 |
| 197 | SLFGQDVKAV | 26036 | ZNF451 |
| 198 | VLYGPDVPTI | 4680 | CEACAM6 |
| 199 | FLLEREQLL | 165055 | CCDC138 |
| 200 | SAVDFIRTL | 9263 | STK17A |
| 201 | GJFNGALAAV | 39 | ACAT2 |
| 202 | GLAALAVHL | 2175 | FANCA |
| 203 | KLIDLSQVMYL | 346389 | MACC1 |
| 204 | KLLDLETERILL | 2803 | GOLGA4 |
| 205 | RLHDENILL | 23322 | RPGRIP1L |
| 206 | RIAGIRGIQGV | 23167 | EFR3A |
| 207 | KLCEGFNEV | 51142, 646630 | CHCHD2, CHCHD2P8 |
| 208 | RLIDRIKTV | 60560 | NAA35 |
| 209 | KLQDGLLHI | 7076 | TIMP1 |
| 210 | KLAVALLAA | 3576 | IL8 |
| 211 | SLFGKKYIL | 2274 | FHL2 |
| 212 | FLLDGSANV | 1293 | COL6A3 |
| 213 | LLWAPTAQA | 389812 | LCN15 |
| 214 | SVLEKEIYSI | 127602 | DNAH14 |
| 215 | KLQEKIQEL | 1062 | CENPE |
| 216 | YLWDLDHGFAGV | 832 | CAPZB |
| 217 | KLLDTMVDTFL | 100527963, 11243 | PMF1-BGLAP, PMF1 |
| 218 | KLSWDLIYL | 51148 | CERCAM |
| 219 | FLDEKGRCV | 4583 | MUC2 |
| 220 | KMDPVAYRV | 5859 | QARS |
| 221 | ILNVDGLIGV | 47 | ACLY |
| 222 | GVIAEILRGV | 10528 | NOP56 |
| 223 | VLMQDSRLYL | 983 | CDK1 |
| 224 | QLQEGKNVIGL | 8407 | TAGLN2 |
| 225 | YLYGQTTTYL | 7153 | TOP2A |
| 226 | FLVDGSWSV | 1303 | COL12A1 |
| 227 | LTAPPEALLMV | 79050 | NOC4L |
| 228 | SMSGYDQVL | 3187, 3188 | HNRNPH1, HNRNPH2 |
| 229 | YLLEKFVAV | 1663, 440081, 642846 | DDX11, DDX12P, LOC642846 |
| 230 | AMSSKFFLV | 7474 | WNT5A |
| 231 | RLFADILNDV | 64755 | C16orf58 |
| 232 | RLLDSVSRL | 3918 | LAMC2 |
| 233 | RLDDLKMTV | 3918 | LAMC2 |
| 234 | KMFESFIESV | 5576 | PRKAR2A |
| 235 | LLHEENFSV | 6942 | TCF20 |
| 236 | KMSELQTYV | 1063 | CENPF |
| 237 | KLVEFDFLGA | 10460 | TACC3 |
| 238 | NMLEAVHTI | 7272 | TTK |
| 239 | QLIEKNWLL | 56992 | KIF15 |
| 240 | VLAPRVLRA | 5954 | RCN1 |
| 241 | ILIDWLVQV | 891 | CCNB1 |

TABLE 3-continued

Peptides useful for e.g. personalized cancer therapies - J = phosphoserine

| SEQ ID No. | Sequence | GeneID(s) | Official Gene Symbol(s) |
|---|---|---|---|
| 242 | RLEEDDGDVAM | 10482 | NXF1 |
| 243 | TLMDMRLSQV | 24148 | PRPF6 |
| 244 | SLHFLILYV | 487, 488 | ATP2A1, ATP2A2 |
| 245 | QLIDYERQL | 11072 | DUSP14 |
| 246 | GLTDNIHLV | 25878 | MXRA5 |
| 247 | SLDTLMTYV | 22829 | NLGN4Y |
| 248 | ALYGDIDAV | 5743 | PTGS2 |
| 249 | ALYGRLEVV | 23294 | ANKS1A |
| 250 | ALCEENMRGV | 1938 | EEF2 |
| 251 | SLLQATDFMSL | 7070 | THY1 |
| 252 | YVYQNNIYL | 2191 | FAP |
| 253 | KLLDEVTYLEA | 1573 | CYP2J2 |
| 254 | VLFQEALWHV | 2194 | FASN |
| 255 | ALALWIPSL | 200634 | KRTCAP3 |
| 256 | GLLEELVTV | 642475 | MROH6 |
| 257 | SLADFMQEV | 23019 | CNOT1 |
| 258 | LLYEGKLTL | 440107 | PLEKHG7 |
| 259 | ALADKELLPSV | 84883 | AIFM2 |
| 260 | ALLAEGITWV | 54499 | TMCO1 |
| 261 | YLYDSETKNA | 4316 | MMP7 |
| 262 | VLAKPGVISV | 1293 | COL6A3 |
| 263 | LLAGQTYHV | 1293 | COL6A3 |
| 264 | RLLDVLAPLV | 80781 | COL18A1 |
| 265 | LLDKKIGV | 10576 | CCT2 |

The present invention furthermore generally relates to the peptides according to the present invention for use in the treatment of proliferative diseases, such as, for example, lung cancer, brain cancer, stomach cancer, kidney cancer, liver cancer, pancreatic cancer, prostate cancer, leukemia, breast cancer, Merkel cell carcinoma (MCC), melanoma, ovarian cancer, and esophageal cancer.

Particularly preferred are the peptides—alone or in combination—according to the present invention selected from the group consisting of SEQ ID NO: 1 to SEQ ID NO: 191. More preferred are the peptides—alone or in combination—selected from the group consisting of SEQ ID NO: 1 to SEQ ID NO: 68 (see Table 1), and their uses in the immunotherapy of CRC, lung cancer, brain cancer, stomach cancer, kidney cancer, liver cancer, pancreatic cancer, prostate cancer, leukemia, breast cancer, Merkel cell carcinoma, melanoma, ovarian cancer, and esophageal cancer, and preferably CRC.

Most preferred are the peptides—alone or in combination—selected from the group consisting of SEQ ID NO: 1, 3, 6, 11, 13, 16, 18, 19, 23, 24, 26, 31, 32, 34, 37, 40, 44, 45, 59, 67, 71, 82, 87, 88, 100, 103, 105, 113, 123, 124, 126, 129, 131, 132, 133, 135, 137, 140, 142, 150, 152, 153, and SEQ ID NO: 166, and their uses in the immunotherapy of CRC, lung cancer, brain cancer, stomach cancer, kidney cancer, liver cancer, pancreatic cancer, prostate cancer, leukemia, breast cancer, Merkel cell carcinoma, melanoma, ovarian cancer, and esophageal cancer, and preferably CRC.

As shown in the following Table 4A and B, many of the peptides according to the present invention are also found on other tumor types and can, thus, also be used in the immunotherapy of other indications. Also refer to FIG. 1D and Example 1.

TABLE 4A

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs/diseases |
|---|---|---|
| 1 | ALIKQLFEA | Lung, Brain, Ovary, Esophagus |
| 3 | RLIPDTLYSV | Lung, Pancreas, Breast, Ovary, Esophagus |
| 4 | RLAELTVDEFL | Lung, Ovary |
| 6 | FLAELPGSLSL | Lung, Liver, Leukocytes, Melanoma, Ovary |
| 8 | ALMLQGVDLL | Pancreas, Leukocytes |
| 10 | RMYNKIFAI | Liver |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs/diseases |
| --- | --- | --- |
| 11 | YLFEKTFNM | Lung, Brain, Esophagus |
| 13 | FLLAEDTKV | Melanoma |
| 15 | LQLDKEFQL | Lung, Esophagus |
| 16 | VLVDQSWVL | Ovary |
| 18 | FLSSLKGGLL | Ovary |
| 19 | RLYTKLLNEA | Brain, Esophagus |
| 25 | SLADRLIGV | Prostate, Ovary |
| 26 | GLASKENFSNVSL | Lung, Liver, Esophagus |
| 29 | QMLDVAIRV | Leukocytes |
| 31 | LLYGKYVSV | Lung, Kidney, Brain, Liver, Leukocytes, Ovary, Esophagus |
| 33 | ALWEKNTHL | Liver, MCC |
| 34 | ILLEKSVSV | Ovary |
| 37 | GLFAGLGGAGA | Esophagus |
| 38 | SLAPTPVSA | Pancreas |
| 40 | ALSNVIHKV | Lung, Pancreas, Esophagus |
| 44 | SLESKLTSV | Brain, Pancreas, Ovary |
| 45 | ALAELLHGA | Lung, Kidney, Brain, Liver, Prostate, Breast, Ovary |
| 46 | GLDDRYSLV | Esophagus |
| 47 | KLYERCEVV | Liver |
| 48 | FLDASDPAL | Kidney, Prostate |
| 53 | FLLGSEIKL | Kidney, Pancreas |
| 54 | ALLNGEYLLAA | Liver, Ovary, Esophagus |
| 55 | QIITSVVSV | Pancreas |
| 56 | VLFTDEGVPKFL | Lung, Kidney, Liver |
| 57 | NLLEKENYL | Ovary |
| 58 | AMADKMDMSL | Brain, Leukocytes, Melanoma |
| 59 | LLTDNVVKL | Lung, Liver, Esophagus |
| 61 | KLLKLFQGV | Kidney |
| 62 | YLAPENGYL | Lung, Liver, Melanoma, Esophagus |
| 63 | KLFSILSTV | Brain, Liver, Prostate, Ovary, Esophagus |
| 65 | FGAPGIISA | Stomach, Esophagus |
| 67 | SLNDLEKDVMLL | Leukocytes, Melanoma |
| 69 | GMLNEAEGKAIKL | Prostate |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs/diseases |
|---|---|---|
| 70 | MISELEVRL | Kidney, Stomach, Prostate, Esophagus |
| 71 | RLWTEIPTAI | Liver |
| 72 | YLLDYPNNLL | Lung, Kidney, Brain, Liver, Leukocytes, Breast, Ovary, Esophagus |
| 74 | YLMGFLHAV | Ovary |
| 76 | YLIGEKQHYL | Liver |
| 77 | SLLKRDFGA | Lung, Breast |
| 79 | SLAADQLLKL | Lung, Liver |
| 80 | QVDEVVDIMRV | Leukocytes |
| 81 | ALLSQQTHL | Esophagus |
| 82 | QLYEEPDTKL | Leukocytes, Esophagus |
| 83 | LTIEDGIFEV | Kidney, Leukocytes, MCC, Melanoma, Esophagus |
| 84 | SMVEDITGLRL | Lung, Liver, Esophagus |
| 87 | LLFDAPDLRL | Lung, Ovary |
| 88 | KLDIKVETV | Lung, Kidney, Liver, Melanoma, Ovary, Esophagus |
| 89 | SLIEYEFRV | Liver, Esophagus |
| 90 | GLLKPGLNVVL | Lung, Esophagus |
| 91 | TVDVATPSV | Breast, Ovary |
| 92 | WIDDTSAFV | Melanoma |
| 98 | AMNGKSFSV | Liver, Esophagus |
| 101 | GLSEGHTFQV | Prostate |
| 102 | KILVSLIEV | Lung, Kidney, Ovary, Esophagus |
| 103 | FLFGYPKRL | Brain, Liver, Prostate |
| 105 | YALDLSTFL | Kidney, Liver |
| 107 | ALLGGGPYML | Lung |
| 108 | SLAELVPGVGGI | Kidney, Brain, Liver, Ovary |
| 110 | LLGELPRLLLL | Lung, Pancreas, Leukocytes |
| 116 | LVYQFVHPI | Pancreas, Prostate, Breast, Ovary |
| 117 | TLQPVDNSTISL | Lung, Kidney, Liver, Pancreas, Esophagus |
| 118 | LLADLKTMV | Brain, Leukocytes, Melanoma |
| 119 | ILYQTVTGL | Esophagus |
| 121 | SLAPNIISQL | Liver, Leukocytes |
| 123 | KTLERSYLL | Lung, Kidney, Liver, MCC, Ovary, Esophagus |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs/diseases |
| --- | --- | --- |
| 124 | RVLPPSALQSV | Lung, Liver, MCC, Melanoma, Ovary, Esophagus |
| 125 | KLGDFGLLVEL | Lung, Brain, Melanoma, Ovary, Esophagus |
| 126 | TLAKYLMEL | Lung, Brain, Liver, Ovary, Esophagus |
| 127 | RLAELTVDEFLA | Ovary |
| 128 | MLDDRAYLV | Lung, Brain, Breast, MCC, Ovary, Esophagus |
| 129 | VLIDVLKEL | Kidney, Leukocytes |
| 131 | KLLDVVHPA | Lung, Brain, Liver, Prostate, Ovary |
| 132 | ALLNAILHSA | Lung, Brain, Liver, Ovary, Esophagus |
| 133 | RTFEKIEEV | Lung, Kidney, Brain, Stomach, Liver, Breast, MCC, Ovary, Esophagus |
| 134 | GVAGGSILKGV | Lung, Liver, Melanoma, Ovary, Esophagus |
| 135 | KLQEEIPVL | Lung |
| 136 | KLFDIFSQQV | Liver |
| 137 | QLTEIKPLL | Brain, Ovary |
| 138 | KQFEGTVEI | Esophagus |
| 139 | VLLNEILEQV | Lung, Liver, Melanoma, Ovary, Esophagus |
| 140 | LLNEILEQV | Lung, Melanoma, Ovary |
| 141 | AVIEHLERL | Lung, Kidney, Esophagus |
| 142 | SLVQRVETI | Lung, Kidney, Liver, Melanoma, Ovary, Esophagus |
| 143 | KLSDVWKEL | Lung |
| 144 | LLNDRIWLA | Esophagus |
| 145 | LLLEVVKQV | Melanoma, |
| 146 | ALSDETWGL | Kidney, Stomach, Pancreas, Breast, Ovary |
| 147 | TLTELRAFL | Kidney |
| 148 | RLLENMTEVV | Liver |
| 149 | YQFDKVGILTL | Leukocytes, Melanoma |
| 151 | SAQGSDVSLTACKV | Lung |
| 152 | KLLAVIHEL | Lung, Kidney, Pancreas, Ovary, Esophagus |
| 153 | ILFSEDSTKLFV | Lung, Liver, Leukocytes, Melanoma, Ovary, Esophagus |
| 154 | KLPSETIFVGC | Lung, Liver, Leukocytes, Ovary, Esophagus |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs/diseases |
|---|---|---|
| 155 | RLLGEEVVRV | Esophagus |
| 156 | SLMMTIINL | Lung, Liver, Melanoma |
| 157 | SLIERDLKL | Lung, Kidney, Brain, Liver, Esophagus |
| 158 | GLLDPSVFHV | Kidney, Brain, Liver, Esophagus |
| 159 | VLVDDDGIKVV | Liver, Melanoma, Ovary |
| 160 | KLLEFDQLQL | Lung, Kidney, Leukocytes, Ovary |
| 161 | FLKNELDNV | Lung, Liver, Leukocytes, Breast, Melanoma, Ovary |
| 162 | KLMDYIDEL | Brain, Esophagus |
| 163 | RLLHEVQEL | Brain |
| 164 | KMLDEILLQL | Brain |
| 165 | RLLDFPEAMVL | Lung, Ovary |
| 166 | GLLEARGILGL | Liver |
| 167 | SVIDHIHLISV | Lung, Melanoma, Ovary |
| 168 | GLIRFPLMTI | Lung, Kidney, Liver |
| 169 | YLAHFIEGL | Brain, Liver, Leukocytes, Esophagus |
| 170 | ALAGGITMV | Lung, Kidney, Liver, Pancreas, Melanoma, Esophagus |
| 171 | RLQETEGMVAV | Liver, Leukocytes, MCC |
| 172 | LLLDTVTMQV | Kidney, Melanoma, Ovary |
| 173 | KLGDLMVLL | Leukocytes |
| 174 | ILLDDNMQIRL | Liver, Melanoma, Ovary |
| 175 | TLLGGKEAQALGV | Ovary |
| 177 | ALLQGAIESV | Melanoma, Ovary, Esophagus |
| 178 | YLFREPATI | Lung, Brain, Liver, Prostate, Melanoma, Ovary, Esophagus |
| 180 | NLLEIAPHL | Brain, Leukocytes, Breast |
| 181 | NLFDLGGQYLRV | Brain, Liver, Ovary |
| 183 | TLQEVVTGV | Prostate, Breast |
| 184 | SLLDENNVSSYL | Lung, Kidney, Liver, Pancreas, Prostate, MCC, Melanoma, Ovary, Esophagus |
| 185 | VLYTGVVRV | Leukocytes, Melanoma, Ovary |
| 186 | KMSEKILLL | Esophagus |
| 187 | GLHNVVYGI | Prostate |
| 188 | FLVDGPRVQL | Breast, Melanoma |
| 189 | AISEVIGKITA | Ovary |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs/diseases |
|---|---|---|
| 190 | AMAEMVLQV | Lung |
| 191 | QLFSEIHNL | Brain, Liver |
| 192 | KIQEMQHFL | Lung, Esophagus |
| 193 | KLSPTVVGL | Liver, Ovary |
| 194 | SLYKGLLSV | Lung, Kidney, Brain, Liver, Ovary, Esophagus |
| 195 | LLLGERVAL | Liver, Ovary |
| 197 | SLFGQDVKAV | MCC, Esophagus |
| 198 | VLYGPDVPTI | Pancreas |
| 199 | FLLEREQLL | Kidney, Leukocytes, Melanoma |
| 200 | SAVDFIRTL | Breast, Esophagus |
| 201 | GJFNGALAAV | Brain, Pancreas |
| 202 | GLAALAVHL | Melanoma, Ovary, Esophagus |
| 203 | KLIDLSQVMYL | Lung, Kidney, Pancreas, Ovary |
| 204 | KLLDLETERILL | Lung, Liver, Prostate, Ovary |
| 205 | RLHDENILL | Lung, Kidney, Brain, Liver, Pancreas, Prostate, Ovary, Esophagus |
| 206 | RIAGIRGIQGV | Lung, Kidney, Liver, Prostate, Ovary |
| 207 | KLCEGFNEV | Brain, Liver |
| 208 | RLIDRIKTV | Lung, Brain, Liver, Ovary |
| 209 | KLQDGLLHI | Kidney, Brain, Liver, Pancreas |
| 210 | KLAVALLAA | Lung, Kidney, Brain, Liver, Esophagus |
| 211 | SLFGKKYIL | Kidney |
| 212 | FLLDGSANV | Lung, Pancreas, Esophagus |
| 214 | SVLEKEIYSI | Lung, Liver, Prostate, Breast, Ovary, Esophagus |
| 215 | KLQEKIQEL | Lung, Ovary, Esophagus |
| 216 | YLWDLDHGFAGV | Lung, Brain, Liver, Prostate, Melanoma, Ovary, Esophagus |
| 217 | KLLDTMVDTFL | Lung, Kidney, Brain, Liver, Ovary, Esophagus |
| 218 | KLSWDLIYL | Lung, Kidney |
| 220 | KMDPVAYRV | Liver, Prostate |
| 221 | ILNVDGLIGV | Kidney, Brain, Liver, Prostate, Leukocytes |
| 222 | GVIAEILRGV | Lung, Kidney, Brain, Liver |
| 223 | VLMQDSRLYL | Lung |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs/diseases |
|---|---|---|
| 224 | QLQEGKNVIGL | Pancreas |
| 225 | YLYGQTTTYL | Lung, Kidney, Stomach, Liver, Melanoma, Ovary, Esophagus |
| 226 | FLVDGSWSV | Lung, Stomach, Pancreas, Breast, Ovary, Esophagus |
| 227 | LTAPPEALLMV | Lung, Kidney, Brain, Liver, Pancreas, Leukocytes, Ovary, Esophagus |
| 228 | SMSGYDQVL | Lung, Leukocytes |
| 229 | YLLEKFVAV | Lung, Liver, Ovary |
| 230 | AMSSKFFLV | Lung, Brain, Stomach, Liver, Pancreas, Prostate, Breast, Ovary, Esophagus |
| 231 | RLFADILNDV | Lung, Brain, Liver, Prostate, MCC, Ovary |
| 232 | RLLDSVSRL | Lung, Kidney, Liver, Pancreas, Breast, Ovary, Esophagus |
| 233 | RLDDLKMTV | Lung, Kidney, Pancreas, Breast, Ovary, Esophagus |
| 234 | KMFESFIESV | Lung, Kidney, Brain, Liver, Prostate, Ovary, Esophagus |
| 235 | LLHEENFSV | Lung, Kidney, Liver, Ovary, Esophagus |
| 236 | KMSELQTYV | Lung, Pancreas, Melanoma, Ovary, Esophagus |
| 237 | KLVEFDFLGA | Lung, Brain, Stomach, Liver, MCC, Ovary, Esophagus |
| 238 | NMLEAVHTI | Lung, Liver, Melanoma, Ovary, Esophagus |
| 239 | QLIEKNWLL | Lung, Liver, Leukocytes, Ovary, Esophagus |
| 240 | VLAPRVLRA | Lung, Kidney, Brain, Liver, Pancreas, Ovary |
| 241 | ILIDWLVQV | Lung, Kidney, Brain, Liver, Pancreas, Ovary, Esophagus |
| 242 | RLEEDDGDVAM | Lung, Kidney, Brain, Liver, Pancreas, Leukocytes, Breast, Melanoma |
| 243 | TLMDMRLSQV | Lung, Kidney, Brain, Liver, Prostate, Ovary |
| 244 | SLHFLILYV | Lung, Kidney, Brain, Liver, Melanoma |
| 245 | QLIDYERQL | Lung, Kidney, Liver, Pancreas, Breast, Esophagus |
| 246 | GLTDNIHLV | Lung, Kidney, Pancreas, Breast, Ovary, Esophagus |
| 247 | SLDTLMTYV | Lung, Kidney, Brain, Pancreas, Prostate, Leukocytes, Esophagus |
| 248 | ALYGDIDAV | Lung, Brain, Pancreas, Esophagus |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs/diseases |
| --- | --- | --- |
| 249 | ALYGRLEVV | MCC, Ovary, Esophagus |
| 250 | ALCEENMRGV | Lung, Kidney, Brain, Liver, MCC, Esophagus |
| 251 | SLLQATDFMSL | Kidney, Pancreas, Esophagus |
| 252 | YVYQNNIYL | Lung, Stomach, Liver, Pancreas, Breast, Melanoma, Ovary, Esophagus |
| 253 | KLLDEVTYLEA | Liver |
| 254 | VLFQEALWHV | Liver |
| 255 | ALALWIPSL | Lung, Pancreas, Ovary, Esophagus |
| 256 | GLLEELVTV | Lung, Stomach, Pancreas, Ovary |
| 257 | SLADFMQEV | Lung, Prostate, MCC, Ovary |
| 258 | LLYEGKLTL | Breast, Ovary |
| 259 | ALADKELLPSV | Lung, Kidney, Liver, Pancreas, Prostate, Melanoma, Ovary, Esophagus |
| 260 | ALLAEGITWV | Liver |
| 261 | YLYDSETKNA | Kidney, Liver, Pancreas, Ovary, Esophagus |
| 262 | VLAKPGVISV | Lung, Pancreas |
| 264 | RLLDVLAPLV | Kidney, Liver |
| 265 | LLDKKIGV | Kidney, Ovary, Esophagus |

TABLE 4B

Peptides according to the present invention and their specific uses in other proliferative diseases, especially in other cancerous diseases (amendment of Table 4A). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thyroid gland, trachea, ureter, urinary bladder.

| SEQ ID NO. | Sequence | Additional Entities |
| --- | --- | --- |
| 1 | ALIKQLFEA | SCLC, GC, BRCA, Melanoma, Urinary bladder cancer, Uterine Cancer, Gallbladder Cancer, Bile Duct Cancer, AML, NHL |
| 2 | ALLPRYFFL | Uterine Cancer |
| 3 | RLIPDTLYSV | Melanoma, Urinary bladder cancer, Uterine Cancer, Gallbladder Cancer, Bile Duct Cancer |
| 4 | RLAELTVDEFL | CLL, Melanoma, Urinary bladder cancer, AML |

TABLE 4B-continued

Peptides according to the present invention and their specific uses in other proliferative diseases, especially in other cancerous diseases (amendment of Table 4A). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thyroid gland, trachea, ureter, urinary bladder.

| SEQ ID NO. | Sequence | Additional Entities |
|---|---|---|
| 6 | FLAELPGSLSL | SCLC, Urinary bladder cancer, Uterine Cancer, Gallbladder Cancer, Bile Duct Cancer, AML, NHL |
| 8 | ALMLQGVDLL | BRCA, Melanoma, Urinary bladder cancer, AML |
| 11 | YLFEKTFNM | SCLC, Urinary bladder cancer |
| 13 | FLLAEDTKV | Urinary bladder cancer, AML, NHL, OC |
| 15 | LQLDKEFQL | CLL, BRCA, Urinary bladder cancer, Uterine Cancer, PC |
| 16 | VLVDQSWVL | Esophageal Cancer, Urinary bladder cancer |
| 18 | FLSSLKGGLL | Melanoma, Urinary bladder cancer, Uterine Cancer, AML |
| 19 | RLYTKLLNEA | Melanoma, Urinary bladder cancer, Uterine Cancer, Gallbladder Cancer, Bile Duct Cancer |
| 22 | GLIDEVMVL | Gallbladder Cancer, Bile Duct Cancer |
| 23 | FLDANGHFV | GC, Esophageal Cancer, Gallbladder Cancer, Bile Duct Cancer |
| 25 | SLADRLIGV | SCLC, BRCA, Uterine Cancer |
| 26 | GLASKENFSNVSL | Urinary bladder cancer, Uterine Cancer, Gallbladder Cancer, Bile Duct Cancer |
| 28 | ALTEIQEFI | NSCLC, Brain Cancer, HCC, BRCA, Melanoma, Esophageal Cancer, Urinary bladder cancer, Gallbladder Cancer, Bile Duct Cancer, AML, NHL |
| 29 | QMLDVAIRV | BRCA |
| 31 | LLYGKYVSV | SCLC, Melanoma, Urinary bladder cancer, Uterine Cancer |
| 32 | KLNTETFGV | GC, BRCA, Esophageal Cancer, AML |
| 33 | ALWEKNTHL | Urinary bladder cancer |
| 34 | ILLEKSVSV | BRCA, Melanoma, Esophageal Cancer, Urinary bladder cancer |
| 35 | KLLDLTVRI | Gallbladder Cancer, Bile Duct Cancer |
| 36 | GLLESPSIFNFTA | BRCA |
| 37 | GLFAGLGGAGA | BRCA, Melanoma, Urinary bladder cancer, Uterine Cancer, Gallbladder Cancer, Bile Duct Cancer |
| 38 | SLAPTPVSA | Uterine Cancer |
| 40 | ALSNVIHKV | Urinary bladder cancer |
| 42 | SILDDSFKL | Gallbladder Cancer, Bile Duct Cancer |
| 43 | TLDAAQPRV | PrC, Esophageal Cancer |
| 44 | SLESKLTSV | Melanoma, Urinary bladder cancer, Uterine Cancer |

TABLE 4B-continued

Peptides according to the present invention and their specific uses in other proliferative diseases, especially in other cancerous diseases (amendment of Table 4A). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thyroid gland, trachea, ureter, urinary bladder.

| SEQ ID NO. | Sequence | Additional Entities |
|---|---|---|
| 45 | ALAELLHGA | Melanoma, Urinary bladder cancer, Uterine Cancer, Gallbladder Cancer, Bile Duct Cancer |
| 46 | GLDDRYSLV | Urinary bladder cancer |
| 47 | KLYERCEVV | Melanoma |
| 53 | FLLGSEIKL | HCC, Melanoma, Urinary bladder cancer, AML |
| 54 | ALLNGEYLLAA | NSCLC, Brain Cancer, GC, BRCA, Melanoma, Urinary bladder cancer, Uterine Cancer, Gallbladder Cancer, Bile Duct Cancer, AML, NHL |
| 55 | QIITSVVSV | CLL, Urinary bladder cancer, Uterine Cancer, AML |
| 56 | VLFTDEGVPKFL | BRCA, Melanoma, Urinary bladder cancer, Uterine Cancer, OC |
| 58 | AMADKMDMSL | NSCLC, SCLC, BRCA, Urinary bladder cancer, Uterine Cancer, Gallbladder Cancer, Bile Duct Cancer, AML, NHL |
| 59 | LLTDNVVKL | Melanoma, AML, NHL |
| 61 | KLLKLFQGV | Melanoma, AML |
| 62 | YLAPENGYL | SCLC, CLL, Urinary bladder cancer, Uterine Cancer, Gallbladder Cancer, Bile Duct Cancer, AML, NHL |
| 63 | KLFSILSTV | SCLC, Melanoma, Urinary bladder cancer, Uterine Cancer, Gallbladder Cancer, Bile Duct Cancer, NHL |
| 64 | KTLGKLWRL | Melanoma |
| 66 | GLDDGPDFL | Melanoma |
| 67 | SLNDLEKDVMLL | SCLC, Urinary bladder cancer, Uterine Cancer, AML, NHL |
| 71 | RLWTEIPTAI | NSCLC, SCLC, Melanoma, Esophageal Cancer, Urinary bladder cancer |
| 72 | YLLDYPNNLL | SCLC, Melanoma, Urinary bladder cancer, Uterine Cancer, Gallbladder Cancer, Bile Duct Cancer, NHL, PC |
| 74 | YLMGFLHAV | BRCA, Urinary bladder cancer |
| 75 | EMIENIQSV | Gallbladder Cancer, Bile Duct Cancer |
| 77 | SLLKRDFGA | SCLC, Melanoma, Esophageal Cancer, Urinary bladder cancer, Uterine Cancer, NHL |
| 78 | ALDPELLLL | AML |
| 79 | SLAADQLLKL | Uterine Cancer |
| 80 | QVDEVVDIMRV | AML |
| 81 | ALLSQQTHL | Urinary bladder cancer, AML |
| 82 | QLYEEPDTKL | SCLC, Melanoma, Urinary bladder cancer, Gallbladder Cancer, Bile Duct Cancer, AML, NHL |

TABLE 4B-continued

Peptides according to the present invention and their specific uses in other proliferative diseases, especially in other cancerous diseases (amendment of Table 4A). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thyroid gland, trachea, ureter, urinary bladder.

| SEQ ID NO. | Sequence | Additional Entities |
| --- | --- | --- |
| 83 | LTIEDGIFEV | NHL |
| 84 | SMVEDITGLRL | SCLC, OC, Urinary bladder cancer, Uterine Cancer, NHL |
| 87 | LLFDAPDLRL | SCLC, BRCA, Urinary bladder cancer, Uterine Cancer |
| 88 | KLDIKVETV | BRCA, Urinary bladder cancer |
| 90 | GLLKPGLNVVL | Urinary bladder cancer, AML |
| 91 | TVDVATPSV | CLL |
| 93 | SLQELRLLL | SCLC |
| 97 | ALWWGVVTV | CLL |
| 98 | AMNGKSFSV | NSCLC, SCLC, BRCA, Melanoma, OC, Urinary bladder cancer, Gallbladder Cancer, Bile Duct Cancer |
| 99 | KLLEVDLDTV | Gallbladder Cancer, Bile Duct Cancer, AML |
| 100 | SLDDFLATA | PC, CLL, BRCA, Melanoma, Esophageal Cancer, Urinary bladder cancer, Uterine Cancer, Gallbladder Cancer, Bile Duct Cancer |
| 102 | KILVSLIEV | NHL |
| 103 | FLFGYPKRL | NSCLC, SCLC, Melanoma, Urinary bladder cancer, Uterine Cancer, AML |
| 105 | YALDLSTFL | BRCA, Melanoma, Urinary bladder cancer, PC |
| 107 | ALLGGGPYML | Urinary bladder cancer, Gallbladder Cancer, Bile Duct Cancer |
| 108 | SLAELVPGVGGI | BRCA |
| 109 | ALDGDQMEL | AML |
| 110 | LLGELPRLLLL | Melanoma, Esophageal Cancer, Urinary bladder cancer |
| 113 | ILYDLQQNL | SCLC, CLL, BRCA, Melanoma, Urinary bladder cancer, Uterine Cancer, Gallbladder Cancer, Bile Duct Cancer, AML, NHL |
| 114 | TAVGHALVL | BRCA, Melanoma, Gallbladder Cancer, Bile Duct Cancer |
| 116 | LVYQFVHPI | Urinary bladder cancer, Uterine Cancer, Gallbladder Cancer, Bile Duct Cancer |
| 117 | TLQPVDNSTISL | Uterine Cancer, Gallbladder Cancer, Bile Duct Cancer |
| 118 | LLADLKTMV | NHL |
| 119 | ILYQTVTGL | CLL, Melanoma, Urinary bladder cancer, Uterine Cancer, AML, NHL |
| 120 | VLYEGVDEV | SCLC, BRCA, Gallbladder Cancer, Bile Duct Cancer |

TABLE 4B-continued

Peptides according to the present invention and their specific uses in other proliferative diseases, especially in other cancerous diseases (amendment of Table 4A). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thyroid gland, trachea, ureter, urinary bladder.

| SEQ ID NO. | Sequence | Additional Entities |
|---|---|---|
| 121 | SLAPNIISQL | AML |
| 123 | KTLERSYLL | SCLC, BRCA, Urinary bladder cancer, Uterine Cancer, AML, NHL, PC |
| 124 | RVLPPSALQSV | SCLC, BRCA, Urinary bladder cancer, Uterine Cancer, Gallbladder Cancer, Bile Duct Cancer, AML, NHL, PC |
| 125 | KLGDFGLLVEL | SCLC, Urinary bladder cancer, AML, PC |
| 126 | TLAKYLMEL | SCLC, BRCA, Melanoma, Urinary bladder cancer, Uterine Cancer, Gallbladder Cancer, Bile Duct Cancer, AML, NHL |
| 127 | RLAELTVDEFLA | SCLC, Melanoma, Urinary bladder cancer, Uterine Cancer, AML |
| 128 | MLDDRAYLV | PC |
| 129 | VLIDVLKEL | Melanoma, NHL |
| 130 | GLGGSQLIDTHL | Esophageal Cancer, Uterine Cancer |
| 131 | KLLDVVHPA | CLL, BRCA, Urinary bladder cancer, Uterine Cancer, AML, NHL |
| 132 | ALLNAILHSA | SCLC, CLL, Melanoma, Urinary bladder cancer, Uterine Cancer, NHL, PC |
| 133 | RTFEKIEEV | SCLC, Melanoma, Urinary bladder cancer, Uterine Cancer, AML, NHL |
| 134 | GVAGGSILKGV | CLL, BRCA, Urinary bladder cancer, Gallbladder Cancer, Bile Duct Cancer, NHL |
| 135 | KLQEEIPVL | BRCA, Melanoma, NHL |
| 136 | KLFDIFSQQV | Urinary bladder cancer, Uterine Cancer, NHL |
| 137 | QLTEIKPLL | CLL, Urinary bladder cancer, Uterine Cancer, Gallbladder Cancer, Bile Duct Cancer, AML, NHL |
| 138 | KQFEGTVEI | CLL, NHL |
| 139 | VLLNEILEQV | SCLC, CLL, Urinary bladder cancer, Uterine Cancer, AML, NHL, PC |
| 140 | LLNEILEQV | SCLC, CLL, Urinary bladder cancer, Uterine Cancer, Gallbladder Cancer, Bile Duct Cancer, AML, NHL |
| 142 | SLVQRVETI | SCLC, PC, BRCA, Urinary bladder cancer, Uterine Cancer, Gallbladder Cancer, Bile Duct Cancer, NHL |
| 143 | KLSDVWKEL | Gallbladder Cancer, Bile Duct Cancer |
| 144 | LLNDRIWLA | BRCA, Melanoma, Uterine Cancer |
| 145 | LLLEVVKQV | Gallbladder Cancer, Bile Duct Cancer, NHL |
| 146 | ALSDETWGL | SCLC, CLL, Esophageal Cancer, Urinary bladder cancer, Uterine Cancer, Gallbladder Cancer, Bile Duct Cancer |

TABLE 4B-continued

Peptides according to the present invention and their specific uses in other proliferative diseases, especially in other cancerous diseases (amendment of Table 4A). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thyroid gland, trachea, ureter, urinary bladder.

| SEQ ID NO. | Sequence | Additional Entities |
|---|---|---|
| 147 | TLTELRAFL | CLL, Uterine Cancer, Gallbladder Cancer, Bile Duct Cancer, NHL |
| 148 | RLLENMTEVV | CLL, OC, Urinary bladder cancer, Uterine Cancer, NHL |
| 149 | YQFDKVGILTL | SCLC, RCC, Brain Cancer |
| 150 | RLADLEALKV | Urinary bladder cancer, NHL |
| 152 | KLLAVIHEL | BRCA, Melanoma, Urinary bladder cancer, Gallbladder Cancer, Bile Duct Cancer, AML, NHL |
| 153 | ILFSEDSTKLFV | Urinary bladder cancer, NHL |
| 154 | KLPSETIFVGC | Melanoma, Uterine Cancer, AML |
| 155 | RLLGEEVVRV | Melanoma |
| 156 | SLMMTIINL | SCLC, GC, Urinary bladder cancer, Uterine Cancer, Gallbladder Cancer, Bile Duct Cancer, AML, NHL, OC |
| 158 | GLLDPSVFHV | Melanoma, Urinary bladder cancer, Gallbladder Cancer, Bile Duct Cancer, AML, NHL |
| 159 | VLVDDDGIKVV | SCLC, BRCA, Esophageal Cancer, Urinary bladder cancer, Uterine Cancer, Gallbladder Cancer, Bile Duct Cancer, NHL |
| 160 | KLLEFDQLQL | SCLC |
| 161 | FLKNELDNV | Esophageal Cancer, Urinary bladder cancer, Uterine Cancer, AML, NHL |
| 162 | KLMDYIDEL | NSCLC, BRCA, Melanoma, Urinary bladder cancer, Gallbladder Cancer, Bile Duct Cancer, NHL |
| 163 | RLLHEVQEL | RCC, AML, NHL |
| 164 | KMLDEILLQL | SCLC, RCC, CLL, Melanoma, OC, Urinary bladder cancer, AML, NHL |
| 165 | RLLDFPEAMVL | SCLC, CLL, Urinary bladder cancer, Uterine Cancer |
| 166 | GLLEARGILGL | Urinary bladder cancer, AML, NHL |
| 167 | SVIDHIHLISV | SCLC, BRCA |
| 168 | GLIRFPLMTI | CLL, Melanoma, Urinary bladder cancer, Uterine Cancer, AML |
| 169 | YLAHFIEGL | Urinary bladder cancer, OC |
| 170 | ALAGGITMV | CLL, Uterine Cancer, Gallbladder Cancer, Bile Duct Cancer, AML, NHL |
| 171 | RLQETEGMVAV | Melanoma, OC |
| 172 | LLLDTVTMQV | Urinary bladder cancer, Gallbladder Cancer, Bile Duct Cancer, AML |
| 173 | KLGDLMVLL | Melanoma, AML, NHL |

TABLE 4B-continued

Peptides according to the present invention and their specific uses in other proliferative diseases, especially in other cancerous diseases (amendment of Table 4A). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thyroid gland, trachea, ureter, urinary bladder.

| SEQ ID NO. | Sequence | Additional Entities |
|---|---|---|
| 174 | ILLDDNMQIRL | SCLC, CLL, Urinary bladder cancer, AML |
| 177 | ALLQGAIESV | SCLC, GC, Urinary bladder cancer, Gallbladder Cancer, Bile Duct Cancer |
| 178 | YLFREPATI | BRCA, Urinary bladder cancer, Uterine Cancer, PC |
| 179 | RLLJPLSSA | AML, BRCA, PC, Gallbaldder Cancer, HCC, Melanoma, NHL, OC, Esophageal Cancer, Brain Cancer, NSCLC, SCLC, Uterine Cancer |
| 180 | NLLEIAPHL | NSCLC, Melanoma, OC, Esophageal Cancer, Urinary bladder cancer, Uterine Cancer, Gallbladder Cancer, Bile Duct Cancer, AML |
| 181 | NLFDLGGQYLRV | CLL, Melanoma, Urinary bladder cancer |
| 182 | SLNKWIFTV | Melanoma |
| 183 | TLQEVVTGV | CLL, Melanoma, Urinary bladder cancer, Uterine Cancer, NHL |
| 184 | SLLDENNVSSYL | SCLC, CLL, BRCA, Urinary bladder cancer, Gallbladder Cancer, Bile Duct Cancer, AML, NHL, OC |
| 185 | VLYTGVVRV | SCLC, BRCA, Esophageal Cancer, AML, NHL |
| 186 | KMSEKILLL | Melanoma |
| 187 | GLHNVVYGI | CLL, Melanoma, Urinary bladder cancer, NHL |
| 188 | FLVDGPRVQL | CLL, Uterine Cancer |
| 189 | AISEVIGKITA | Gallbladder Cancer, Bile Duct Cancer, PC |
| 190 | AMAEMVLQV | SCLC, CLL, BRCA, Urinary bladder cancer, Gallbladder Cancer, Bile Duct Cancer, AML, NHL |
| 191 | QLFSEIHNL | SCLC, Melanoma, Urinary bladder cancer, Gallbladder Cancer, Bile Duct Cancer, AML, NHL, PC |

NSCLC=non-small cell lung cancer, SCLC=small cell lung cancer, RCC=kidney cancer, CRC=colon or rectum cancer, GC=stomach cancer, HCC=liver cancer, PC=pancreatic cancer, PrC=prostate cancer, BRCA=breast cancer, MCC=Merkel cell carcinoma, OC=ovarian cancer, NHL=non-Hodgkin lymphoma, AML=acute myeloid leukemia, CLL=chronic lymphocytic leukemia.

Thus, another aspect of the present invention relates to the use of at least one peptide according to the present invention according to any one of SEQ ID No. 1, 3, 4, 6, 11, 15, 26, 31, 40, 45, 56, 59, 62, 72, 77, 79, 84, 87, 88, 90, 102, 107, 110, 117, 123, 124, 125, 126, 128, 131, 132, 133, 134, 135, 139, 140, 141, 142, 143, 151, 152, 153, 154, 156, 157, 160, 161, 165, 167, 168, 170, 178, 184, 190, 192, 194, 203, 204, 205, 206, 208, 210, 212, 214, 215, 216, 217, 218, 222, 223, 225, 226, 227, 228, 229, 230, 231, 232, 233, 234, 235, 236, 237, 238, 239, 240, 241, 242, 243, 244, 245, 246, 247, 248, 250, 252, 255, 256, 257, 259, and 262 for the—in one preferred embodiment combined—treatment of lung cancer.

Thus, another aspect of the present invention relates to the use of at least one peptide according to the present invention according to any one of SEQ ID No. 1, 11, 19, 31, 44, 45, 58, 63, 72, 103, 108, 118, 125, 126, 128, 131, 132, 133, 137, 157, 158, 162, 163, 164, 169, 178, 180, 181, 191, 194, 201, 205, 207, 208, 209, 210, 216, 217, 221, 222, 227, 230, 231, 234, 237, 240, 241, 242, 243, 244, 247, 248, and 250 for the—in one preferred embodiment combined—treatment of brain cancer.

Thus, another aspect of the present invention relates to the use of at least one peptide according to the present invention according to any one of SEQ ID No. 65, 70, 133, 146, 225, 226, 230, 237, 252, and 256 for the—in one preferred embodiment combined —treatment of stomach cancer.

Thus, another aspect of the present invention relates to the use of at least one peptide according to the present invention according to any one of SEQ ID No. 31, 45, 48, 53, 56, 61, 70, 72, 83, 88, 102, 105, 108, 117, 123, 129, 133, 141, 142, 146, 147, 152, 157, 158, 160, 168, 170, 172, 184, 194, 199, 203, 205, 206, 209, 210, 211, 217, 218, 221, 222, 225, 227, 232, 233, 234, 235, 240, 241, 242, 243, 244, 245, 246, 247, 250, 251, 259, 261, 264, and 265 for the—in one preferred embodiment combined—treatment of kidney cancer.

Thus, another aspect of the present invention relates to the use of at least one peptide according to the present invention according to any one of SEQ ID No. 6, 10, 26, 31, 33, 45, 47, 54, 56, 59, 62, 63, 71, 72, 76, 79, 84, 88, 89, 98, 103, 105, 108, 117, 121, 123, 124, 126, 131, 132, 133, 134, 136, 139, 142, 148, 153, 154, 156, 157, 158, 159, 161, 166, 168, 169, 170, 171, 174, 178, 181, 184, 191, 193, 194, 195, 204, 205, 206, 207, 208, 209, 210, 214, 216, 217, 220, 221, 222, 225, 227, 229, 230, 231, 232, 234, 235, 237, 238, 239, 240, 241, 242, 243, 244, 245, 250, 252, 253, 254, 259, 260, 261, and 264 for the—in one preferred embodiment combined—treatment of liver cancer.

Thus, another aspect of the present invention relates to the use of at least one peptide according to the present invention according to any one of SEQ ID No. 3, 8, 38, 40, 44, 53, 55, 110, 116, 117, 146, 152, 170, 184, 198, 201, 203, 205, 209, 212, 224, 226, 227, 230, 232, 233, 236, 240, 241, 242, 245, 246, 247, 248, 251, 252, 255, 256, 259, 261, and 262 for the—in one preferred embodiment combined—treatment of pancreatic cancer.

Thus, another aspect of the present invention relates to the use of at least one peptide according to the present invention according to any one of SEQ ID No. 25, 45, 48, 63, 69, 70, 101, 103, 116, 131, 178, 183, 184, 187, 204, 205, 206, 214, 216, 220, 221, 230, 231, 234, 243, 247, 257, and 259 for the—in one preferred embodiment combined—treatment of prostate cancer.

Thus, another aspect of the present invention relates to the use of at least one peptide according to the present invention according to any one of SEQ ID No. 6, 8, 29, 31, 58, 67, 72, 80, 82, 83, 110, 118, 121, 129, 149, 153, 154, 160, 161, 169, 171, 173, 180, 185, 199, 221, 227, 228, 239, 242, and 247 for the—in one preferred embodiment combined—treatment of leukemia.

Thus, another aspect of the present invention relates to the use of at least one peptide according to the present invention according to any one of SEQ ID No. 3, 45, 72, 77, 91, 116, 128, 133, 146, 161, 180, 183, 188, 200, 214, 226, 230, 232, 233, 242, 245, 246, 252, and 258 for the—in one preferred embodiment combined—treatment of breast cancer.

Thus, another aspect of the present invention relates to the use of at least one peptide according to the present invention according to any one of SEQ ID No. 33, 83, 123, 124, 128, 133, 171, 184, 197, 231, 237, 249, 250, and 257 for the—in one preferred embodiment combined—treatment of Merkel cell carcinoma.

Thus, another aspect of the present invention relates to the use of at least one peptide according to the present invention according to any one of SEQ ID No. 6, 13, 58, 62, 67, 83, 88, 92, 118, 124, 125, 134, 139, 140, 142, 145, 149, 153, 156, 159, 161, 167, 170, 172, 174, 177, 178, 184, 185, 188, 199, 202, 216, 225, 236, 238, 242, 244, 252, and 259 for the—in one preferred embodiment combined—treatment of melanoma.

Thus, another aspect of the present invention relates to the use of at least one peptide according to the present invention according to any one of SEQ ID No. 1, 3, 4, 6, 16, 18, 25, 31, 34, 44, 45, 54, 57, 63, 72, 74, 87, 88, 91, 102, 108, 116, 123, 124, 125, 126, 127, 128, 131, 132, 133, 134, 137, 139, 140, 142, 146, 152, 153, 154, 159, 160, 161, 165, 167, 172, 174, 175, 177, 178, 181, 184, 185, 189, 193, 194, 195, 202, 203, 204, 205, 206, 208, 214, 215, 216, 217, 225, 226, 227, 229, 230, 231, 232, 233, 234, 235, 236, 237, 238, 239, 240, 241, 243, 246, 249, 252, 255, 256, 257, 258, 259, 261, and 265 for the—in one preferred embodiment combined—treatment of ovarian cancer.

Thus, another aspect of the present invention relates to the use of at least one peptide according to the present invention according to any one of SEQ ID No. 1, 3, 11, 15, 19, 26, 31, 37, 40, 46, 54, 59, 62, 63, 65, 70, 72, 81, 82, 83, 84, 88, 89, 90, 98, 102, 117, 119, 123, 124, 125, 126, 128, 132, 133, 134, 138, 139, 141, 142, 144, 152, 153, 154, 155, 157, 158, 162, 169, 170, 177, 178, 184, 186, 192, 194, 197, 200, 202, 205, 210, 212, 214, 215, 216, 217, 225, 226, 227, 230, 232, 233, 234, 235, 236, 237, 238, 239, 241, 245, 246, 247, 248, 249, 250, 251, 252, 255, 259, 261, and 265 for the—in one preferred embodiment combined—treatment of esophageal cancer.

Thus, another aspect of the present invention relates to the use of the peptides according to the present invention for the—preferably combined—treatment of a proliferative disease selected from the group of CRC, lung cancer, brain cancer, stomach cancer, kidney cancer, liver cancer, pancreatic cancer, prostate cancer, leukemia, breast cancer, Merkel cell carcinoma, melanoma, ovarian cancer, and esophageal cancer.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 191.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T-cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No. 191, preferably containing SEQ ID No. 1 to SEQ ID No. 68, or a variant amino acid sequence.

The present invention further relates to activated T-cells, produced by the method according to the present invention, wherein said T-cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T-cells as produced according to the present invention.

The present invention further relates to the use of any peptide as described, the nucleic acid according to the present invention, the expression vector according to the present invention, the cell according to the present invention, the activated T lymphocyte, the T-cell receptor or the antibody or other peptide- and/or peptide-MHC-binding molecules according to the present invention as a medicament or in the manufacture of a medicament. Preferably, said medicament is active against cancer.

Preferably, said medicament is a cellular therapy, a vaccine or a protein based on a soluble TCR or antibody.

The present invention further relates to a use according to the present invention, wherein said cancer cells are CRC, lung cancer, brain cancer, stomach cancer, kidney cancer, liver cancer, pancreatic cancer, prostate cancer, leukemia, breast cancer, Merkel cell carcinoma (MCC), melanoma, ovarian cancer, and esophageal cancer, and preferably CRC cells.

The present invention further relates to biomarkers based on the peptides according to the present invention, herein called "targets", that can be used in the diagnosis of cancer, preferably CRC. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these novel targets in the context of cancer treatment.

Both therapeutic and diagnostic uses against additional cancerous diseases are disclosed in the following more detailed description of the underlying expression products (polypeptides) of the peptides according to the invention.

AKAP8 (also called AKAP95) encodes a member of the A-kinase anchor protein family, which includes scaffold proteins that contain a binding domain for the RI/RII subunit of protein kinase A (PKA) and recruit PKA and other signaling molecules to specific subcellular locations. AKAP8 binds to the RII alpha subunit of PKA and may play a role in chromosome condensation during mitosis by targeting PKA and the condensin complex to chromatin (RefSeq, 2002). AKAP8 protein expression is significantly up-regulated in rectal and lung cancer and is associated with cell differentiation and the histopathological type, suggesting an important role in tumor development and progression. The expression of AKAP8 correlates with the expression of Cyclin E and Cyclin D (Chen et al., 2012; Hu et al., 2013; Qi et al., 2015).

ARHGAP39 (also called Vilse or CrGAP) encodes a Rho GTPase-activating protein that is involved in Roundabout (Robo) receptor-mediated repulsive axon guidance and the regulation of RAC-dependent cytoskeletal changes (Hu et al., 2005). ARHGAP39 is frequently up-regulated in bladder cancer cell lines (Matsuda et al., 2011). ARHGAP39 is involved in directional migration of endothelial cells (Kaur et al., 2008).

AURKB (also called AIM-1) encodes aurora kinase B a member of the aurora kinase subfamily of serine/threonine kinases. AURKB regulates together with other proteins the segregation of chromosomes during mitosis and meiosis through association with microtubules (RefSeq, 2002). AURKB expression is up-regulated in different cancer types, including lung, colorectal and breast cancer as well as leukemia and thereby associated with poor prognosis. So development of AURKB inhibitors for clinical therapy is an interesting field (Hayama et al., 2007; Pohl et al., 2011; Hegyi et al., 2012; Goldenson and Crispino, 2015). AURKB over-expression leads to phosphorylation of histone H3 and to chromosome instability, a crucial factor for carcinogenesis (Ota et al., 2002; Tatsuka et al., 1998). AURKB activity augments the oncogenic Ras-mediated cell transformation (Kanda et al., 2005).

C18orf21 (also called XTP13) encodes an abnormal hemoglobin beta chain peptide associated with inhibition of HIV infection (Liu et al., 2011a; Aschauer et al., 1983).

CCNB1 encodes for cyclin B1 a regulatory protein involved in mitosis. It has two alternative transcripts, one expressed constitutively and the other predominantly during G2/M phase (RefSeq, 2002). CCNB1 encodes cyclin B1, a regulatory protein involved in mitosis (RefSeq, 2002). CCNB1 is a well-described tumor antigen and CCNB1 over-expression has been described for breast, head and neck, prostate, colorectal, lung and liver cancers (Egloff et al., 2006). CCNB1 was shown to be up-regulated in a variety of cancer entities, including colorectal cancer, breast cancer, lung cancer and renal cancer.

The down-regulation of CCNB1 leads to G2/M phase cell cycle arrest and the inhibition of proliferation and migration (Chang et al., 2013; Sakurai et al., 2014; Fang et al., 2014; Ding et al., 2014). Genetic polymorphisms in the CCNB1 gene are related with breast cancer susceptibility, progression and survival of Chinese Han woman (Li et al., 2013).

CCNB2 encodes cyclin B2, a member of the family of cyclins that plays a role in cell cycle regulation (RefSeq, 2002). CCNB2 is up-regulated in colorectal adenocarcinoma (Park et al., 2007). CCNB2 is over-expressed in various human tumors. Strong CCNB2 expression in tumor cells is associated with a poor prognosis in patients with adenocarcinoma of lung and invasive breast carcinoma (Takashima et al., 2014; Albulescu, 2013).

CCT7 encodes for chaperonin containing TCP1 complex (CCT) subunit 7 (eta), which is involved in the ATP-dependent folding of various proteins including actin and tubulin. CCT7 was found to be a part of a protein subnetwork, which is significantly discriminative of late stage human colorectal cancer (Nibbe et al., 2009).

CDC42BPG (also called MRCKgamma) encodes CDC42 Binding Protein Kinase Gamma (DMPK-Like), a member of the myotonic dystrophy kinase-related CDC42 binding kinases family (Ng et al., 2004).

CDC6 encodes a protein essential for the initiation of DNA replication (RefSeq, 2002). CDC6 expression is de-regulated in different cancer types including gallbladder, cervical and prostate cancer (Wu et al., 2009; Wang et al., 2009c; Robles et al., 2002; Shu et al., 2012). CDC6 co-operates with c-Myc to promote genetic instability, tumor-like transformation and apoptosis attenuation (Chen et al., 2014a). Hypoxia-induced ATR promotes the degradation of CDC6. Initiation of DNA replication is regulated by p53 through Cdc6 protein stability (Duursma and Agami, 2005; Martin et al., 2012).

CENPE encodes centromere protein E, 312 kDa, a kinesin-like motor protein that accumulates in the G2 phase of the cell cycle. CENPE is proposed to be one of the motors responsible for mammalian chromosome movement and/or spindle elongation (RefSeq, 2002). CENPE expression significantly correlated with glioma grade and might complement other parameters for predicting survival time for glioma patients (Bie et al., 2011). CENPE is up-regulated in chemo-resistant epithelial ovarian tumors compared to chemo-sensitive tumors (Ju et al., 2009). CENPE is up-regulated in invasive and aggressive-invasive prolactin pituitary tumors (Wierinckx et al., 2007).

CIRH1A (also called Cirhin) encodes cirrhosis autosomal recessive 1 A, a WD40-repeat-containing protein localized in the nucleolus. It causes North American Indian childhood cirrhosis (NAIC) (RefSeq, 2002). CIRH1A can up-regulate a canonical NF-kappaB element and might participate in the regulation of other genes containing NF-kappaB elements. This suggests that CIRH1A can influence the cancer-related NF-kappaB pathway (Yu et al., 2009).

CNOT1 encodes an enzymatic relevant subunit of the CCR4-NOT deadenylase complex which is an important regulator of translation and mRNA stability (Ito et al., 2011; Boland et al., 2013). Single-nucleotide polymorphisms (SNPs) in the CNOT1 gene were detected in osteosarcoma and acute lymphoblastic leukemia (ALL) (Gutierrez-Camino et al., 2014; Bilbao-Aldaiturriaga et al., 2015). CNOT1 depletion induces stabilization of mRNAs and activation of ER stress-mediated apoptosis (Ito et al., 2011).

COL12A1 encodes the alpha chain of type XII collagen, a member of the FACIT (fibril-associated collagens with interrupted triple helices) collagen family and thus is a part of extracellular matrix (ECM) (RefSeq, 2002). COL12A1 is over-expressed in drug-resistant variants of ovarian cancer cell lines (Januchowski et al., 2014). In colorectal cancer, COL12A1 is over-expressed in desmoplastic stroma by and around cancer-associated fibroblasts, as well as in cancer cells lining the invasion front (Karagiannis et al., 2012).

CYP2W1 encodes a member of the cytochrome P450 superfamily of enzymes which are monooxygenases catalyzing many reactions involved in drug metabolism and in the synthesis of cholesterol, steroids and other lipids (RefSeq, 2002). CYP2W1 is over-expressed in a variety of human cancers including hepatocellular, colorectal and gastric cancer. CYP2W1 over-expression is associated with tumor progression and poor survival (Aung et al., 2006; Gomez et al., 2010; Zhang et al., 2014e). Due to tumor-specific expression, CYP2W1 is an interesting drug target or enzymatic activator of pro-drugs during cancer therapy (Karlgren and Ingelman-Sundberg, 2007; Nishida et al., 2010).

ECT2 encodes the epithelial cell transforming protein 2, a guanine nucleotide exchange factor and transforming protein that is related to Rho-specific exchange factors and cell cycle regulators (RefSeq, 2002). ECT2 is over-expressed as a result of tumor-specific gene amplifications in a variety of human tumors including lung, ovarian, gastric and pancreatic cancer. ECT2 is important for cell proliferation, migration, invasion and tumorigenicity (Fields and Justilien, 2010; Jin et al., 2014). Protein kinase C iota and ECT2 activate through MEK/ERK signaling a tumor-initiating cell phenotype in ovarian cancer (Wang et al., 2013e). Nuclear ECT2 is binding preferentially to the Rho GTPase Rac1 and leads through Rac1 activation to cellular transformation, while cytoplasmic ECT2 binds to the Rho GTPase RhoA and leads through RhoA activation to the formation of cytokinetic furrow (Su et al., 2011; Huff et al., 2013).

GPR56 encodes adhesion G protein-coupled receptor G1 (ADGRG1), which regulates brain cortical patterning. GPR56 binds specifically to transglutaminase 2, an inhibitor of tumor progression (RefSeq, 2002). GPR56 inhibits tumorigenesis by suppression of tumor growth and metastasis in melanomas and prostate cancer. The role in other cancer types appeared to be complex, maybe due to the varying ability of the different splicing variants of GPR56 to activate transcription factors like for c-myc and p53 response elements (Kim et al., 2010b; Xu et al., 2010; Yang and Xu, 2012). GPR56 inhibits VEGF production from melanoma cells and impedes their angiogenesis and growth through a signaling pathway involving protein kinase C alpha (Yang et al., 2011a).

HS6ST2 encodes a member of the heparin sulfate (HS) sulfotransferase gene family. HS6ST2 catalyzes the transfer of sulfate to HS (RefSeq, 2002). HS6ST2 is over-expressed in different cancer types including thyroid, colorectal and ovarian cancer and is associated with migration, invasion and poor prognosis (Backen et al., 2007; Hatabe et al., 2013; Di et al., 2014). TGF-beta promotes cancer metastasis by stimulation of HS6ST2 and IL-11 production (Pollari et al., 2012). HS6ST2 is a regulator of angiogenesis in response to EGF, FGF2 and VEGF signaling pathways (Ferreras et al., 2012; Cole et al., 2014).

IER3 (also called IEX-1) encodes immediate early response 3 that has a function in protection of cells from Fas- or tumor necrosis factor alpha-induced apoptosis (RefSeq, 2002). De-regulation of IER3 expression in ovarian, pancreatic, blood, breast and colorectal cancer, lymphoma and myeloma is linked to poor or better prognosis, depending on the type and progression stages of tumors and makes the protein a valuable biomarker, either alone or with other genes (Wu et al., 2013). IER3 gene expression plays an important role in regulating apoptosis and cell growth through a positive or negative way. Over-expression of IER3 renders some cells sensitive to apoptosis and accelerates cell cycle progression, but reduces proliferation of other cells, whereas disruption of IER3 expression is associated with a decrease in both apoptosis and cell cycle progression (Zhang et al., 2011a). IER3 interferes with certain signaling pathways, in particular NF-kappaB, MAPK/ERK and PI3K/Akt. Mouse models also revealed an involvement of IER3 expression in immune functions (Arlt and Schafer, 2011; Wu, 2003).

ITPR3 encodes a receptor for inositol 1,4,5-trisphosphate containing a C-terminal calcium-channel and a N-terminal ligand-binding site. ITPR3 plays a role in exocrine secretion underlying energy metabolism and growth (RefSeq, 2002). ITPR3 is over-expressed in several cancer types including colorectal, gastric and breast cancer and directly related to cancer progression and the aggressiveness of the tumor (Shibao et al., 2010; Mound et al., 2013; Sakakura et al., 2003). Akt can protect cells in an ITPR3-dependent manner from apoptosis through reducing the Ca2+ release from the endoplasmatic reticulum (Marchi et al., 2012).

KCNN4 (also called KCa3.1 or hIKCa1) encodes a part of a heterotetrameric voltage-independent potassium channel that is activated by intracellular calcium. The activation of this channel is followed by membrane hyper-polarization which promotes calcium influx (RefSeq, 2002). KCNN4 is up-regulated in several cancers including breast, lung and prostate cancer and is associated with cell proliferation and tumor growth (Chou et al., 2008; Lallet-Daher et al., 2009; Haren et al., 2010; Bulk et al., 2015). Inhibition of KCNN4 regulates reactive oxygen species (ROS) levels and promotes p53 activation which suppresses the growth and migration of cells and leads to apoptosis (Liu et al., 2015b).

KIRREL (also called NEPH1) encodes a member of the nephrin-like protein family whose members interact with the cytoplasmic domain of podocin (RefSeq, 2002).

KLK10 (also called NES1) encodes a member of the kallikrein subfamily of serine proteases which play a role in carcinogenesis and have potential as biomarkers (RefSeq, 2002). KLK10 is up-regulated in colon, ovarian and gastric cancer but down-regulated in breast, lung and prostate cancer (Yousef et al., 2005; Feng et al., 2006; Zhang et al., 2010; Li et al., 2001). The epigenetic silencing of KLK10 is maintained by TGFbeta/Smad signaling whereas KLK10 up-regulation is promoted by activate Ras/MEK/ERK and PI3K/Akt signaling (Paliouras and Diamandis, 2008; Papageorgis et al., 2010).

LIG1 is a DNA repair gene involved in the nucleotide excision repair (NER) and the base excision repair (BER) pathways. LIG1 single-nucleotide polymorphisms are associated with the risk of lung cancer, endometrial cancer and glioma (Doherty et al., 2011; Lee et al., 2008b; Liu et al., 2009).

LSG1 encodes large 60S subunit nuclear xxport GTPase 1. The protein is necessary for cell viability and may localize in the endoplasmic reticulum, nucleus and cytoplasm (RefSeq, 2002).

LSM14B (also called RAP55B) encodes a member of the LSM (like Sm) domain family that is involved in RNA metabolism, regulation of the mitotic G2/M phase, translational repression, incorporation into mRNP particles, P-body formation and stress granule localization (Marnef et al., 2009; Albrecht and Lengauer, 2004).

MAGED2 encodes melanoma antigen family D, 2, a member of a new defined MAGE-D cluster in Xp11.2, a hot spot for X-linked mental retardation. MAGED2 is expressed ubiquitously with high expression levels in specific brain regions and in the interstitium of testes. MAGED2 is a potential negative regulator of wildtype p53 activity (Langnaese et al., 2001; Papageorgio et al., 2007). MAGED2 over-expression is associated with melanoma, breast cancer and colon cancer (Li et al., 2004; Strekalova et al., 2015).

MAGEF1 encodes a member of the melanoma antigen (MAGE) superfamily that contains a microsatellite repeat and is ubiquitously expressed, suggesting a role in normal cell physiology (Stone et al., 2001). Flavopiridol induces an inhibition of human tumor cell proliferation and the down-regulation of MAGEF1 in different human tumor cell lines (Lu et al., 2004). MAGEF1 is significantly over-expressed in colorectal cancer tissues (Chung et al., 2010).

MDH1 encodes malate dehydrogenase, an enzyme that catalyzes the reversible oxidation of malate to oxaloacetate utilizing the NAD/NADH cofactor system in the citric acid cycle. MDH1 is localized to the cytoplasm and may play a pivotal role in the malate-aspartate shuttle which operates in the metabolic coordination between cytosol and mitochondria (RefSeq, 2002). In glioblastoma MDH1 is a target for several de-regulated microRNAs and its expression is repressed. Together with known tumor suppressors or onco-genes MDH1 can help to discriminate low versus high grade gliomas (Lages et al., 2011; Kounelakis et al., 2013). MDH1 is over-expressed in null cell pituitary adenomas and in thyroid oncocytomas (Hu et al., 2007; Baris et al., 2004).

MYO10 encodes a member of the myosin superfamily that represents an unconventional myosin. It functions as an actin-based molecular motor and plays a role in the integration of F-actin and microtubule cytoskeletons during meiosis (RefSeq, 2002). MYO10 is over-expressed in several cancer entities, including breast and lung cancer and is associated with metastasis, cell migration and an aggressive phenotype (Cao et al., 2014; Sun et al., 2015b; Courson and Cheney, 2015). Mutant p53 promotes NCAPG encodes the non-SMC condensing I complex subunit G which is responsible for the condensation and stabilization of chromosomes during mitosis and meiosis (RefSeq, 2002). NCAPG is down-regulated in patients with multiple myeloma, acute myeloid leukemia, and leukemic cells from blood or myeloma cells (Cohen et al., 2014). NCAPG may be a multi-drug resistant gene in colorectal cancer (Li et al., 2012). NCAPG is highly up-regulated in the chromophobe subtype of human cell carcinoma but not in conventional human renal cell carcinoma (Kim et al., 2010a). Up-regulation of NCAPG is associated with melanoma progression (Ryu et al., 2007). NCAPG is associated with uveal melanoma (Van Ginkel et al., 1998). NCAPG shows variable expression in different tumor cells (Jager et al., 2000).

NDRG3 encodes a member of N-myc downstream-regulated genes that is highly expressed in testis, prostate and ovary and may play a role in spermatogenesis (Zhao et al., 2001). NDRG3 may function as a tumor suppressor gene in different cancer types including bladder cancer (Yang et al., 2013; Tsui et al., 2015). NDRG3 acts as a tumor promoter in prostate cancer where an up-regulated expression leads to an increased growth rate, higher migration and induction of angiogenic chemokines. Up-regulation of NDRG3 is associated with a malignant phenotype in hepatocellular cancer cells (Wang et al., 2009b; Fan et al., 2011).

NOL11 encodes nucleolar protein 11 that is required for optimal rDNA transcription in the ribosome biogenesis (Freed et al., 2012; Griffin et al., 2015). Nol11 is an interactor of the breast and ovarian tumor suppressor BRCA1 (Hill et al., 2014).

PLAGL2 encodes a member of pleiomorphic adenoma gene (PLAG) family and is a zinc finger protein that recognizes DNA and/or RNA (Kas et al., 1998). PLAGL2 functions as a proto-oncogene in a variety of cancers including leukemia, gliomas, colorectal cancer and lung adenocarcinomas. There is also evidence that PLAGL2 can act as a tumor suppressor by initiating cell cycle arrest and apoptosis (Yang et al., 2011b; Hanks and Gauss, 2012; Liu et al., 2014a). PLAGL2 prevents proteosomal degradation of the E3 ubiquitin ligase Pirh2 which is regulating the stability of p53. PLAGL2 expression also increases the p73 level and up-regulates p73 target genes like p21 and Bax (Zheng et al., 2007; Hanks and Gauss, 2012; Landrette et al., 2005).

PTCD2 encodes the pentatricopeptide repeat domain protein 2 that may be involved in processing RNA transcripts, including cytochrome b derived from mitochondrial DNA. Dysfunction of this protein plays a possible role in the etiology of heart failure (Xu et al., 2008).

RAD54 encodes a protein belonging to the DEAD-like helicase superfamily. It shares similarity with *Saccharomyces cerevisiae* RAD54 and RDH54, both of which are involved in homologous recombination and repair of DNA. This protein binds to double-stranded DNA, and displays ATPase activity in the presence of DNA. This gene is highly expressed in testis and spleen, which suggests active roles in meiotic and mitotic recombination (RefSeq, 2002). Homozygous mutations of RAD54B were observed in primary lymphoma and colon cancer (Hiramoto et al., 1999). RAD54B counteracts genome-destabilizing effects of direct binding of RAD51 to dsDNA in human tumor cells (Mason et al., 2015).

RNASEH2A encodes a component of the heterotrimeric type II ribonuclease H enzyme and is the major source of its activity. RNASEH2A is an endonuclease and is predicted to remove Okazaki fragment RNA primers during lagging strand DNA synthesis (RefSeq, 2002). RNASEH2A is up-regulated in transformed mesenchymal stem cells and overexpressed in numerous cancer cells, including aggressive prostate cancer. Knock-down of RNASEH2A inhibits anchorage-independent growth but does not alter proliferation of cancer cells (Flanagan et al., 2009; Williams et al., 2014).

RRM1 encodes ribonucleotide reductase M1 an enzyme that is essential for the production of deoxyribonucleotides prior to DNA synthesis in S phase of dividing cells. It is one of several genes located in the imprinting gene domain of 11p15.5, an important tumor suppressor gene region (RefSeq, 2002). RRM1 is involved in the regulation of cell proliferation, cell migration, tumorigenesis and metastasis development. Studies with large numbers of patients with different types of cancer, such as lung, pancreatic, breast and gastric cancer establish the prognostic or predictive value of RRM1 (Carvalho et al., 2009; Jordheim et al., 2011; Wang et al., 2013d). The nucleoside analog gemcitabine, a common chemotherapeutic in cancer treatment, is targeting RRM1 (Jordheim and Dumontet, 2013).

SERPINB5 (also called maspin) encodes serpin peptidase inhibitor clade B member 5 that is characterized as a class II tumor suppressor based on its ability to promote apoptosis and inhibit cell invasion and angiogenesis (Bailey et al., 2006). SERPINB5 is both a valuable molecular marker for the diagnosis and a predictor for the prognosis of many cancer types including breast, lung, head and neck, oral and prostate cancer (Marioni et al., 2009; Lonardo et al., 2010; Sager et al., 1996; Sheng, 2004). SERPINB5 acts as an endogenous regulator of HDAC1 activity and interacts with the p53 tumor suppressor pathway (Maass et al., 2000; Kaplun et al., 2012).

SEZ6L2 encodes a seizure-related protein that is localized on the cell surface and enriched in pancreatic beta-cells (RefSeq, 2002; Stutzer et al., 2013). The expression of SEZ6L2 is up-regulated in lung cancer and a higher expression level is related to a shorter survival (Ishikawa et al., 2006).

SMARCA4 (also called BRG1) encodes a member of the helicase and ATPase containing proteins of the SWI/SNF family that is part of the large ATP-dependent chromatin remodeling complex SWI/SNF. The complex is required for transcriptional activation of genes normally repressed by chromatin (RefSeq, 2002). SMARCA4 acts as a tumor suppressor and is down-regulated via mutations in different cancer entities including breast, lung and colon cancer. Low SMARCA4 levels are associated with tumor progression like mutation and invasion (Medina and Sanchez-Cespedes, 2008; Bai et al., 2013b; Reisman et al., 2003; Wang et al., 2016). SMARCA4 is related to several tumor suppressors and important tumor associated proteins like p53, p16INK4a, hTERT and Akt (Medina and Sanchez-Cespedes, 2008; Becker et al., 2009; Naidu et al., 2009; Liu et al., 2014b; Wu et al., 2014a).

SMC2 (also called CAP-E or SMC2L1) encodes a member of the structural maintenance of chromosomes family which is critical for mitotic chromosome condensation and DNA repair (RefSeq, 2002). The SMC2 gene is altered by frameshift mutation and loss of expression in gastric and colorectal cancer with microsatellite instability suggesting that SMC2 might be involved in tumor pathogenesis (Je et al., 2014). SMC2 gene alterations can play a role in genome instability, which accelerates the accumulation of other alterations in pyothorax-associated lymphomas (Ham et al., 2007).

SVIL encodes supervillin, a bipartite protein with distinct amino- and carboxy-terminal domains that appears to aid in myosin II assembly during cell spreading and disassembly of focal adhesions (RefSeq, 2002). SVIL is significantly down-regulated in prostate cancer tissue mainly through promoter methylation (Vanaja et al., 2006). SVIL regulates cell survival through control of p53 levels. SVIL expression is necessary for the cross-talk between survival signaling and cell motility pathways (Fang and Luna, 2013).

TMEM222 encodes the transmembrane protein 222 located on chromosome 1p36.11 (RefSeq, 2002).

ZNF679 encodes a zinc finger protein containing a KRAB (KrUppel-associated box) domain that functions as a transcription factor. The promoter region of ZNF679 is bound by the co-repressor KAP1 and H3me3K9 (histon 3 trimethylation of lysine 9) (O'Geen et al., 2007).

DETAILED DESCRIPTION OF THE INVENTION

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

As used herein and except as noted otherwise all terms are defined as given below.

The term "T-cell response" means the specific proliferation and activation of effector functions induced by a peptide in vitro or in vivo. For MHC class I restricted cytotoxic T-cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13, or 14 or longer, and in case of MHC class II peptides (elongated variants of the peptides of the invention) they can be as long as 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T-cell "epitope" requires a short peptide that is bound to a class I MHC receptor, forming a ternary complex (MHC class I alpha chain, beta-2-microglobulin, and peptide) that can be recognized by a T-cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 5

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein bind to A*02. A vaccine may also include pan-binding MHC class II peptides. Therefore, the vaccine of the invention can be used to treat cancer in patients that are A*02 positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86% (calculated from www.allelefrequencies.net).

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" shall mean a short nucleic acid sequence that can be paired with one strand of DNA and provides a free 3'-OH end at which a DNA polymerase starts synthesis of a deoxyribonucleotide chain.

The term "promoter" shall mean a region of DNA involved in binding of RNA polymerase to initiate transcription.

The term "isolated" shall mean that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human.

Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{percent identity} = 100[1-(C/R)]$$

wherein C is the number of differences between the Reference Sequence and the Compared Sequence over the length of alignment between the Reference Sequence and the Compared Sequence, wherein
(i) each base or amino acid in the Reference Sequence that does not have a corresponding aligned base or amino acid in the Compared Sequence and
(ii) each gap in the Reference Sequence and
(iii) each aligned base or amino acid in the Reference Sequence that is different from an aligned base or amino acid in the Compared Sequence, constitutes a difference and
(iiii) the alignment has to start at position 1 of the aligned sequences;
and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 191 or a variant thereof which is 88% homologous to SEQ ID NO: 1 to SEQ ID NO: 191, or a variant thereof that will induce T-cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T-cells induced by a variant of a specific peptide will be able to cross-react with the peptide itself (Appay et al., 2006; Colombetti et al., 2006; Fong et al., 2001; Zaremba et al., 1997).

By a "variant" of a given amino acid sequence, the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 191. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T-cells.

These T-cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 191, by maintaining the known anchor residues, and would be able to determine whether such variants maintain the ability to bind MHC class I or II molecules. The variants of the present invention retain the ability to bind to the TCR of activated T-cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or -II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or -II is substantially changed, or is negatively affected, when compared to the non-modified peptide.

The amino acid residues that do not substantially contribute to interactions with the T-cell receptor can be modified by replacement with other amino acids whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 6

Variants and motif of the peptides according to SEQ ID NO: 7, 9, 31, 192, 212, and 142

| | Position | | | | | | | | |
|---|---|---|---|---|---|---|---|---|---|
| | 1 | 2 | 3 | 4 | 5 | 6 | 7 | 8 | 9 |
| SEQ ID NO. 7 Variants | Y | L | T | R | H | L | A | V | L |
| | | | | | | | | | V |
| | | | | | | | | | I |
| | | | | | | | | | A |
| | | M | | | | | | | V |
| | | M | | | | | | | I |
| | | M | | | | | | | |
| | | M | | | | | | | A |
| | | A | | | | | | | V |
| | | A | | | | | | | I |
| | | A | | | | | | | |
| | | A | | | | | | | A |
| | | V | | | | | | | V |
| | | V | | | | | | | I |
| | | V | | | | | | | |
| | | V | | | | | | | A |
| | | T | | | | | | | V |
| | | T | | | | | | | I |
| | | T | | | | | | | |
| | | T | | | | | | | A |
| | | Q | | | | | | | V |
| | | Q | | | | | | | I |
| | | Q | | | | | | | |
| | | Q | | | | | | | A |
| SEQ ID NO. 9 Variants | I | L | D | D | H | L | S | R | V |
| | | | | | | | | | I |
| | | | | | | | | | L |
| | | | | | | | | | A |
| | | M | | | | | | | |
| | | M | | | | | | | I |
| | | M | | | | | | | L |
| | | M | | | | | | | A |
| | | A | | | | | | | |
| | | A | | | | | | | I |
| | | A | | | | | | | L |
| | | A | | | | | | | A |
| | | V | | | | | | | |
| | | V | | | | | | | I |
| | | V | | | | | | | L |
| | | V | | | | | | | A |
| | | T | | | | | | | |
| | | T | | | | | | | I |
| | | T | | | | | | | L |
| | | T | | | | | | | A |
| | | Q | | | | | | | |
| | | Q | | | | | | | I |
| | | Q | | | | | | | L |
| | | Q | | | | | | | A |
| SEQ ID NO. 31 Variants | L | L | Y | G | K | Y | V | S | V |
| | | | | | | | | | I |
| | | | | | | | | | L |
| | | | | | | | | | A |
| | | M | | | | | | | |
| | | M | | | | | | | I |
| | | M | | | | | | | L |
| | | M | | | | | | | A |
| | | A | | | | | | | |
| | | A | | | | | | | I |
| | | A | | | | | | | L |
| | | A | | | | | | | A |
| | | V | | | | | | | |
| | | V | | | | | | | I |
| | | V | | | | | | | L |
| | | V | | | | | | | A |
| | | T | | | | | | | |
| | | T | | | | | | | I |
| | | T | | | | | | | L |
| | | T | | | | | | | A |
| | | Q | | | | | | | |
| | | Q | | | | | | | I |
| | | Q | | | | | | | L |
| | | Q | | | | | | | A |
| SEQ ID 192 Variants | K | I | Q | E | M | Q | H | F | L |
| | | L | | | | | | | V |
| | | L | | | | | | | I |
| | | L | | | | | | | |
| | | L | | | | | | | A |
| | | M | | | | | | | V |

TABLE 6-continued

Variants and motif of the peptides according to SEQ ID NO: 7, 9, 31, 192, 212, and 142

| | Position | | | | | | | | |
|---|---|---|---|---|---|---|---|---|---|
| | 1 | 2 | 3 | 4 | 5 | 6 | 7 | 8 | 9 |
| | | M | | | | | | | I |
| | | M | | | | | | | |
| | | M | | | | | | | A |
| | | A | | | | | | | V |
| | | A | | | | | | | I |
| | | A | | | | | | | |
| | | A | | | | | | | A |
| | | V | | | | | | | V |
| | | V | | | | | | | I |
| | | V | | | | | | | |
| | | V | | | | | | | A |
| | | T | | | | | | | V |
| | | T | | | | | | | I |
| | | T | | | | | | | |
| | | T | | | | | | | A |
| | | Q | | | | | | | V |
| | | Q | | | | | | | I |
| | | Q | | | | | | | |
| | | Q | | | | | | | A |
| SEQ ID 212 Variants | F | L | L | D | G | S | A | N | V |
| | | | | | | | | | I |
| | | | | | | | | | L |
| | | | | | | | | | A |
| | | M | | | | | | | |
| | | M | | | | | | | I |
| | | M | | | | | | | L |
| | | M | | | | | | | A |
| | | A | | | | | | | |
| | | A | | | | | | | I |
| | | A | | | | | | | L |
| | | A | | | | | | | A |
| | | V | | | | | | | |
| | | V | | | | | | | I |
| | | V | | | | | | | L |
| | | V | | | | | | | A |
| | | T | | | | | | | |
| | | T | | | | | | | I |
| | | T | | | | | | | L |
| | | T | | | | | | | A |
| | | Q | | | | | | | |
| | | Q | | | | | | | I |
| | | Q | | | | | | | L |
| | | Q | | | | | | | A |
| SEQ ID 142 Variants | S | L | V | Q | R | V | E | T | I |
| | | | | | | | | | V |
| | | | | | | | | | L |
| | | | | | | | | | A |
| | | | | | | | | | V |
| | | M | | | | | | | |
| | | M | | | | | | | L |
| | | M | | | | | | | A |
| | | M | | | | | | | V |
| | | A | | | | | | | |
| | | A | | | | | | | L |
| | | A | | | | | | | A |
| | | V | | | | | | | V |
| | | V | | | | | | | |
| | | V | | | | | | | L |
| | | V | | | | | | | A |
| | | T | | | | | | | V |
| | | T | | | | | | | |
| | | T | | | | | | | L |
| | | T | | | | | | | A |
| | | Q | | | | | | | V |
| | | Q | | | | | | | |
| | | Q | | | | | | | L |
| | | Q | | | | | | | A |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 7.

TABLE 7

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T-cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by T-cells from more than one individual, at least two, and more preferably three individuals.

In a particularly preferred embodiment of the invention the peptide consists or consists essentially of an amino acid sequence according to SEQ ID NO: 1 to SEQ ID NO: 191.

"Consisting essentially of" shall mean that a peptide according to the present invention, in addition to the sequence according to any of SEQ ID NO: 1 to SEQ ID NO 191 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH═CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural TUMAPs recorded from CRC samples (N=24 A*02-positive samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from 24 CRC patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from CRC tissue samples were purified and HLA-associated peptides were isolated and analyzed by LC-MS (see examples). All TUMAPs contained in the present application were identified with this approach on primary CRC samples confirming their presentation on primary CRC.

TUMAPs identified on multiple CRC and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

Furthermore, the discovery pipeline XPRESIDENT® v2.x allows the direct absolute quantitation of MHC-, preferably HLA-restricted, peptide levels on cancer or other infected tissues. Briefly, the total cell count was calculated from the total DNA content of the analyzed tissue sample. The total peptide amount for a TUMAP in a tissue sample was measured by nanoLC-MS/MS as the ratio of the natural TUMAP and a known amount of an isotope-labelled version of the TUMAP, the so-called internal standard. The efficiency of TUMAP isolation was determined by spiking peptide:MHC complexes of all selected TUMAPs into the tissue lysate at the earliest possible point of the TUMAP isolation procedure and their detection by nanoLC-MS/MS following completion of the peptide isolation procedure. The total cell count and the amount of total peptide were calculated from triplicate measurements per tissue sample. The peptide-specific isolation efficiencies were calculated as an average from 10 spike experiments each measured as a triplicate (see Example 6 and Table 12).

The present invention provides peptides that are useful in treating cancers/tumors, preferably CRC that over- or exclusively present the peptides of the invention. These peptides were shown by mass spectrometry to be naturally presented by HLA molecules on primary human CRC samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy cells from the large intestine (colon or rectum) or other normal tissue cells, demonstrating a high degree of tumor association of the source genes (see Example 2). Moreover, the peptides themselves are strongly over-presented on tumor tissue—"tumor tissue" in relation to this invention shall mean a sample from a patient suffering from CRC, but not on normal tissues (see Example 1).

HLA-bound peptides can be recognized by the immune system, specifically T lymphocytes. T-cells can destroy the cells presenting the recognized HLA/peptide complex, e.g. CRC cells presenting the derived peptides.

The peptides of the present invention have been shown to be capable of stimulating T-cell responses and/or are over-presented and thus can be used for the production of antibodies and/or TCRs, such as soluble TCRs, according to the present invention (see Example 3, Example 4). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are peptides capable of binding to TCRs and antibodies when presented by an MHC molecule. The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to a peptide-HLA molecule complex with a binding affinity (KD) of about 100 μM or less, about 50 μM or less, about 25 μM or less, or about 10 μM or less. More preferred are high affinity TCRs having binding affinities of about 1 μM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for a peptide-HLA molecule complex of 100 μM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta heterodimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, an peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to the peptides according tot he invention can be enhanced by methods well known in the art.

The present description further relates to a method of identifying and isolating a TCR according to the present description, said method comprising incubating PBMCs from HLA-A*02-negative healthy donors with A2/peptide monomers, incubating the PBMCs with tetramer-phycoerythrin (PE) and isolating the high avidity T-cells by fluo-rescence activated cell sorting (FACS)—Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with peptide of interest, incubating PBMCs obtained from the transgenic mice with tetramer-phycoerythrin (PE), and isolating the high avidity T-cells by fluorescence activated cell sorting (FACS)—Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient. In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1 a and the spleen focus-forming virus (SFFV) promoter. In a preferred embodiment, the promoter is heterologous to the nucleic acid being expressed. In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Nucleic acids encoding TCRs of the present description may be codon optimized to increase expression from a host cell. Redundancy in the genetic code allows some amino acids to be encoded by more than one codon, but certain codons are less "op-timal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion). (Schmitt et al. 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH$_2$ group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutics such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin 2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T-cells. However, stimulation of CD8 T-cells is more efficient in the presence of help provided by CD4 T-helper cells. Thus, for MHC Class I epitopes that stimulate CD8 T-cells the fusion partner or sections of a hybrid molecule suitably provide epitopes which stimulate CD4-positive T-cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 191, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos.

4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill in the art.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells.

However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T-cells for the respective opposite CDR as noted above.

The medicament of the invention may also include one or more adjuvants. Adjuvants are substances that non-specifically enhance or potentiate the immune response (e.g., immune responses mediated by CD8-positive T-cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid coglycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T-cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonal®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g.

anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonal®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomateous or cancerous diseases. Exemplary formulations can be found in, for example, EP2112253.

It is important to realize that the immune response triggered by the vaccine according to the invention attacks the cancer in different cell-stages and different stages of development. Furthermore different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Bancherau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T-cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T-cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example a fluorescence-labelling, for example provided by a fluorescence dye, can provide a visualisation of the bound aptamer by fluorescence or laser scanning microscopy or flow cytometry.

Each scaffold can be conjugated with a second active molecule such as for example IL-21, anti-CD3, anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO 191, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 191, or a variant thereof which is at least 88% homologous (preferably identical) to SEQ ID NO: 1 to SEQ ID NO: 191 or a variant thereof that induces T-cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 191 or a variant thereof which is at least 88% homologous (preferably identical) to SEQ ID NO: 1 to SEQ ID NO: 191, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 191.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of CRC.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, where-in the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 191 or said variant amino acid sequence.

The present invention further relates to activated T-cells, produced by the method according to the present invention, wherein said T-cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T-cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are CRC cells or other solid or haematological tumor cells such as lung cancer, brain cancer, stomach cancer, kidney cancer, liver cancer, pancreatic cancer, prostate cancer, leukemia, breast cancer, Merkel cell carcinoma, melanoma, ovarian cancer, and esophageal cancer.

The present invention further relates to particular marker proteins and biomarkers based on the peptides according to the present invention, herein called "targets" that can be used in the diagnosis and/or prognosis of CRC. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a CRC marker (poly)peptide, delivery of a toxin to a CRC cell expressing a cancer marker gene at an increased level, and/or inhibiting the activity of a CRC marker polypeptide) according to the invention.

Whenever possible, the antibodies of the invention may be purchased from commercial sources. The antibodies of the invention may also be generated using well-known methods. The skilled artisan will understand that either full length CRC marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 191 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the CRC marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields an F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating CRC, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), domains recruiting effector cells such as an anti-CD3 domain, etc., in order to execute particular functions on target cells. Moreover, it could be expressed in T-cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 μM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T-cells, the method comprising contacting in vitro T-cells with antigen loaded human MHC molecules expressed on the surface of a suitable antigen-presenting cell for a period of time sufficient to activate the T-cell in an antigen specific manner, wherein the antigen is a peptide according to the invention. Preferably, a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and *Drosophila* cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T-cells are CD8-positive T-cells.

If an antigen-presenting cell is transfected to express such an epitope, preferably the cell comprises an expression vector capable of expressing a peptide containing SEQ ID NO: 1 to SEQ ID NO: 191, or a variant amino acid sequence thereof.

A number of other methods may be used for generating T-cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T-cells. Furthermore, the production of autologous T-cells by pulsing dendritic cells with peptide or polypeptide, or via infection with recombinant virus is possible. Also, B cells can be used in the production of autologous T-cells. In addition, macrophages pulsed with peptide or polypeptide, or infected with recombinant virus, may be used in the preparation of autologous T-cells. S. Walter et al. (Walter et al., 2003) describe the in vitro priming of T-cells by using artificial antigen presenting cells (aAPCs), which is also a suitable way for generating T-cells against the peptide of choice. In the present invention, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively elicit high- or low-avidity antigen-specific T-cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e.g. cytokines, like interleukin 12.

Allogeneic cells may also be used in the preparation of T-cells and a method is described in detail in WO 97/26328, incorporated herein by reference. For example, in addition to *Drosophila* cells and T2 cells, other cells may be used to present antigens such as CHO cells, baculovirus-infected insect cells, bacteria, yeast, vaccinia-infected target cells. In addition plant viruses may be used (see, for example, Porta et al. (Porta et al., 1994) which describes the development of cowpea mosaic virus as a high-yielding system for the presentation of foreign peptides.

The activated T-cells that are directed against the peptides of the invention are useful in therapy. Thus, a further aspect of the invention provides activated T-cells obtainable by the foregoing methods of the invention.

Activated T-cells, which are produced by the above method, will selectively recognize a cell that aberrantly expresses a polypeptide that comprises an amino acid sequence of SEQ ID NO: 1 to SEQ ID NO 191.

Preferably, the T-cell recognizes the cell by interacting through its TCR with the HLA/peptide-complex (for example, binding). The T-cells are useful in a method of killing target cells in a patient whose target cells aberrantly express a polypeptide comprising an amino acid sequence of the invention wherein the patient is administered an effective number of the activated T-cells. The T-cells that are administered to the patient may be derived from the patient and activated as described above (i.e. they are autologous T-cells). Alternatively, the T-cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T-cells according to the present invention can be cells of the tumor (which sometimes express MHC class II) and/or stromal cells surrounding the tumor (tumor cells) (which sometimes also express MHC class II; (Dengjel et al., 2006)).

The T-cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T-cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T-cells may be obtained by methods known in the art, e.g. those described above.

Protocols for this so-called adoptive transfer of T-cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T-cell. This engineered T-cell can then be transferred to a patient for therapy of cancer.

Any molecule of the invention, i.e. the peptide, nucleic acid, antibody, expression vector, cell, activated T-cell, T-cell receptor or the nucleic acid encoding it, is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

The present invention is further directed at a kit comprising:
(a) a container containing a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from two to six administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from CRC, the medicament of the invention is preferably used to treat CRC.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T-cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of CRC patients with various HLA-A HLA-B and HLA-C alleles. It may contain MHC class I and MHC class II peptides or elongated MHC class I peptides. In addition to the tumor associated peptides collected from several CRC tissues, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, CRC samples from patients and blood from healthy donors were analyzed in a stepwise approach:
1. HLA ligands from the malignant material were identified by mass spectrometry
2. Genome-wide messenger ribonucleic acid (mRNA) expression analysis was used to identify genes over-expressed in the malignant tissue (CRC) compared with a range of normal organs and tissues
3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T-cells from healthy donors as well as from CRC patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T-cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 µm sterile filter. The final bulk solution is obtained.

Final bulk solution is filled into vials and stored at −20° C. until use. One vial contains 700 µL solution, containing 0.578 mg of each peptide. Of this, 500 µL (approx. 400 µg per peptide) will be applied for intradermal injection.

In addition to being useful for treating cancer, the peptides of the present invention are also useful as diagnostics. Since the peptides were generated from CRC cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for CRC. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T-cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying figures, nevertheless, without being limited thereto. For the purposes of the present invention, all references as cited herein are incorporated by reference in their entireties.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A to 1M show the over-presentation of various peptides in normal tissues (white bars) and CRC (black bars). FIG. 1A: Gene symbol(s): ZNF679, ZNF716, SAPCD2, Peptide: ALIKQLFEA (SEQ ID NO.: 1), Tissues from left to right: 1 adipose tissues, 3 adrenal glands, 6 arteries, 3 bone marrows, 7 brains, 3 breasts, 1 nerv, 1 ovary, 8 esophagi, 2 gallbladders, 5 hearts, 16 kidneys, 21 livers, 46 lungs, 3 lymph nodes, 4 leukocyte samples, 3 ovaries, 7 pancreas, 4 peripheral nerves, 1 peritoneum, 1 pituitary gland, 2 placentas, 3 pleuras, 1 prostate, 2 salivary glands, 4 skeletal muscles, 4 skins, 2 small intestines, 4 spleens, 7 stomachs, 4 testes, 2 thymi, 3 thyroid glands, 1 trachea, 1 ureter, 3 urinary bladders, 2 uteri, 2 veins, 13 colons, 6 recti, 24 CRC. The peptide has additionally been detected on 9/99 lung cancers, 2/28 brain cancers, 4/20 ovarian cancers, 1/45 stomach cancers, 1/33 prostate cancers, and 2/15 esophageal cancers (not shown). FIG. 1B: Gene symbol(s): BRCA2, Peptide: KQFEGTVEI (SEQ ID NO.: 138), Tissues from left to right: 1 adipose tissues, 3 adrenal glands, 6 arteries, 3 bone marrows, 7 brains, 3 breasts, 1 nerv, 1 ovary, 8 esophagi, 2 gallbladders, 5 hearts, 16 kidneys, 21 livers, 46 lungs, 3 lymph nodes, 4 leukocyte samples, 3 ovaries, 7 pancreas, 4 peripheral nerves, 1 peritoneum, 1 pituitary gland, 2 placentas, 3 pleuras, 1 prostate, 2 salivary glands, 4 skeletal muscles, 4 skins, 2 small intestines, 4 spleens, 7 stomachs, 4 testes, 2 thymi, 3 thyroid glands, 1 trachea, 1 ureter, 3 urinary bladders, 2 uteri, 2 veins, 13 colons, 6 recti, 24 CRC. The peptide has additionally been detected on 1/15 esophageal cancers, 1/28 brain cancers, 1/45 stomach cancers, and 3/91 lung cancers (not shown). FIG. 1C: Gene symbol(s): IL8, Peptide: KLAVALLAA (SEQ ID NO.: 210), Tissues from left to right: 1 adipose tissues, 3 adrenal glands, 6 arteries, 3 bone marrows, 7 brains, 3 breasts, 1 nerv, 1 ovary, 8 esophagi, 2 gallbladders, 5 hearts, 16 kidneys, 21 livers, 46 lungs, 3 lymph nodes, 4 leukocyte samples, 3 ovaries, 7 pancreas, 4 peripheral nerves, 1 peritoneum, 1 pituitary gland, 2 placentas, 3 pleuras, 1 prostate, 2 salivary glands, 4 skeletal muscles, 4 skins, 2 small intestines, 4 spleens, 7 stomachs, 4 testes, 2 thymi, 3 thyroid glands, 1 trachea, 1 ureter, 3 urinary bladders, 2 uteri, 2 veins, 13 colons, 6 recti, 24 CRC. The peptide has additionally been detected on 14/99 lung cancers, 1/18 kidney cancers, 2/28 brain cancers, 2/16 liver cancers, 1/20 ovarian cancers, 1/45 stomach cancers, and 3/15 esophageal cancers (not shown). FIG. 1D) Gene symbol(s): TMEM222, Peptide: LLYGKYVSV (SEQ ID NO.: 31) Tissues from left to right: 3 pancreatic cell lines, 3 skin cell lines, 1 leucocytic cell line, 0 normal tissues, 28 cancer tissues (2 brain cancers, 1 breast cancer, 1 colon cancer, 1 esophageal cancer, 2 kidney cancers, 1 leukemia, 5 liver cancers, 7 lung cancers, 5 ovarian cancers, 1 prostate cancer, 2 rectal cancers). The normal tissue panel tested was the same as in FIG. 1A-C. Discrepancies regarding the list of tumor types between FIG. 1D and table 4 might be due to the more stringent selection criteria applied in table 4 (for details please refer to table 4). FIG. 1D shows all samples with detectable presentation of the peptide Y, regardless of over-presentation parameters and technical sample quality check. FIG. 1E: Gene symbol(s): ZNF679, ZNF716, SAPCD2, Peptide: ALIKQLFEA (SEQ ID NO.: 1), Tissues from left to right: 7 cancer cell lines, 1 primary cancer cell culture, 58 cancer tissues (5 brain cancers, 1 breast cancer, 9 colon cancers, 1 colorectal cancer, 3 esophageal cancers, 1 gallbladder cancer, 2 leukocytic leukemia cancers, 15 lung cancers, 2 lymph node cancers, 1 myeloid cells cancer, 5 ovarian cancers, 1 prostate cancer, 4 rectum cancers, 1 skin cancer, 2 stomach cancers, 2 urinary bladder cancers, 3 uterus cancers). The normal tissue panel tested was the same as in FIGS. 1A-1C. FIG. 1F: F) Gene symbol(s): PLAGL2, Peptide: FLAELPGSLSL (SEQ ID NO.: 6), Tissues from left to right: 8 cancer cell lines, 1 primary cancer cell culture, 2 normal tissues (1 lymph node, 1 spleen), 57 cancer tissues (1 bone marrow cancer, 1 breast cancer, 1 cecum cancer, 5 colon cancers, 2 esophageal cancers, 1 gallbladder cancer, 3 leukocytic leukemia cancers, 2 liver cancers, 13 lung cancers, 8 lymph node cancers, 1 myeloid cells cancer, 9 ovarian cancers, 2 rectum cancers, 1 skin cancer, 1 stomach cancer, 4 urinary bladder cancers, 2 uterus cancers). The normal tissue panel tested was the same as in FIGS. 1A-1C. FIG. 1G: Gene symbol(s): CYP2W1, Peptide: FLDANGHFV (SEQ ID NO.: 23), Tissues from left to right: 1 primary cancer cell culture, 3 normal tissues (3 placentas), 12 cancer tissues (5 colon cancers, 1 esophageal cancer, 1 gallbladder cancer, 2 rectum cancers, 3 stomach cancers). The normal tissue panel tested was the same as in FIG. 1A-C. FIG. 1H: Gene symbol(s): CYP2W1, Peptide: GLIDEVMVL (SEQ ID NO.: 22), Tissues from left to right: 1 normal tissue (1 stomach), 6 cancer tissues (3 colon cancers, 1 gallbladder cancer, 2 rectum cancers). The normal tissue panel tested was the same as in FIGS. 1A-1C. FIG. 1I: Gene symbol(s): AXIN2, Peptide: ILDDHLSRV (SEQ ID NO.: 9), Tissues from left to right: 5 cancer tissues (1 cecum cancer, 1 colon cancer, 1 lung cancer, 2 rectum cancers). The normal tissue panel tested was the same as in FIG. 1A-1C. FIG. 1J: Gene symbol(s): RAD54B, Peptide: KLLAVIHEL (SEQ ID NO.: 152), Tissues from left to right: 3 cell lines, 2 normal tissues (1 lymph node, 1 spleen), 34 cancer tissues (1 breast cancer, 7 colon cancers, 1 esophageal cancer, 1 gallbladder cancer, 1 kidney cancer, 8 lung cancers, 4 lymph node cancers, 1 myeloid cells cancer, 4 ovarian cancers, 1 pancreas cancer, 1 rectum cancer, 3 skin cancers, 1 urinary bladder cancer). The normal tissue panel tested was the same as in FIGS. 1A-1C. FIG. 1K: Gene symbol(s): ECT2, Peptide: SLVQRVETI (SEQ ID NO.: 142), Tissues from left to right: 5 cell lines, 1 primary culture, 47 cancer tissues (2 bile duct cancers, 2 breast cancers, 1 cecum cancer, 7 colon cancers, 3 esophageal cancers, 3 gallbladder cancers, 1 kidney cancer, 2 liver cancers, 10 lung cancers, 2 lymph node cancers, 4 ovarian cancers, 1 pancreas cancer, 2 rectum cancers, 2 skin cancers, 1 stomach cancer, 2 urinary bladder cancers, 2 uterus cancers). The normal tissue panel tested was the same as in FIG. 1A-1C. FIG. 1L:Gene symbol(s): MMP12, Peptide: KIQEMQHFL (SEQ ID NO.: 192), Tissues from left to right: 1 primary culture, 44 cancer tissues (5 colon cancers, 1 esophageal cancer, 1 gallbladder cancer, 1 head and neck cancer, 30 lung cancers, 1 lymph node cancer, 1 rectum cancer, 1 stomach cancer, 1 testis cancer, 1 urinary bladder cancer, 1 uterus cancer). The normal tissue panel tested was the same as in FIG. 1A-1C. FIG. 1M: Gene symbol(s): COL6A3, Peptide: FLLDGSANV (SEQ ID NO.: 212), Tissues from left to right: 3 cell lines, 2 normal tissues (1 placenta, 1 spleen), 146 cancer tissues (4 bile duct cancers, 13 breast cancers, 1 cecum cancer, 8 colon cancers, 1 colorectal cancer, 6 esophageal cancers, 5 gallbladder cancers, 5 head and neck cancers, 2 kidney cancers, 1 liver cancer, 62 lung cancers, 2 lymph node cancers, 9 ovarian cancers, 7 pancreas cancers, 3 rectum cancers, 4 skin cancers, 5 stomach cancers, 5 urinary bladder cancers, 3 uterus cancers). The normal tissue panel tested was the same as in FIGS. 1A-1C.

FIGS. 2A to 2C show exemplary expression profiles (relative expression compared to normal colon and rectum) of source genes of the present invention that are highly over-expressed or exclusively expressed in CRC in a panel of normal tissues (white bars) and 10 CRC samples (black bars). Tissues from left to right: adrenal gland, artery, bone marrow, brain (whole), breast, colon, esophagus, heart, kidney (triplicate), leukocytes, liver, lung, lymph node, ovary, pancreas, placenta, prostate, salivary gland, skeletal muscle, skin, small intestine, spleen, stomach, testis, thymus, thyroid gland, urinary bladder, uterine cervix, uterus, vein, 3 normal colon samples, 10 CRC samples. FIG. 2A, CCNB1; FIG. 2B, CDK1; FIG. 2C, CHMP5. FIG. 2D shows exemplary expression profiles (relative expression compared to normal colon and rectum) of source genes of the present invention that are highly over-expressed or exclusively expressed in CRC in a panel of normal tissues (white bars) and 20 CRC samples (black bars). Tissues from left to right: 6 arteries, 2 blood cells, 2 brains, 1 heart, 2 livers, 3 lungs, 2 veins, 1 adipose tissue, 1 adrenal gland, 5 bone marrows, 1 cartilage, 1 colon, 1 esophagus, 2 eyes, 2 gallbladders, 2 salivary glands, 1 kidney, 6 lymph nodes, 4 pancreases, 2 peripheral nerves, 2 pituitary glands, 1 rectum, 2 skeletal muscles, 1 skin, 1 small intestine, 1 spleen, 1 stomach, 1 thyroid gland, 7 tracheas, 1 urinary bladder, 1 breast, 5 ovaries, 5 placentas, 1 prostate, 1 testis, 1 thymus, 1 uterus, 20 CRC samples. FIG. 2D: ECT2.

EXAMPLES

Example 1

Figure 1A:
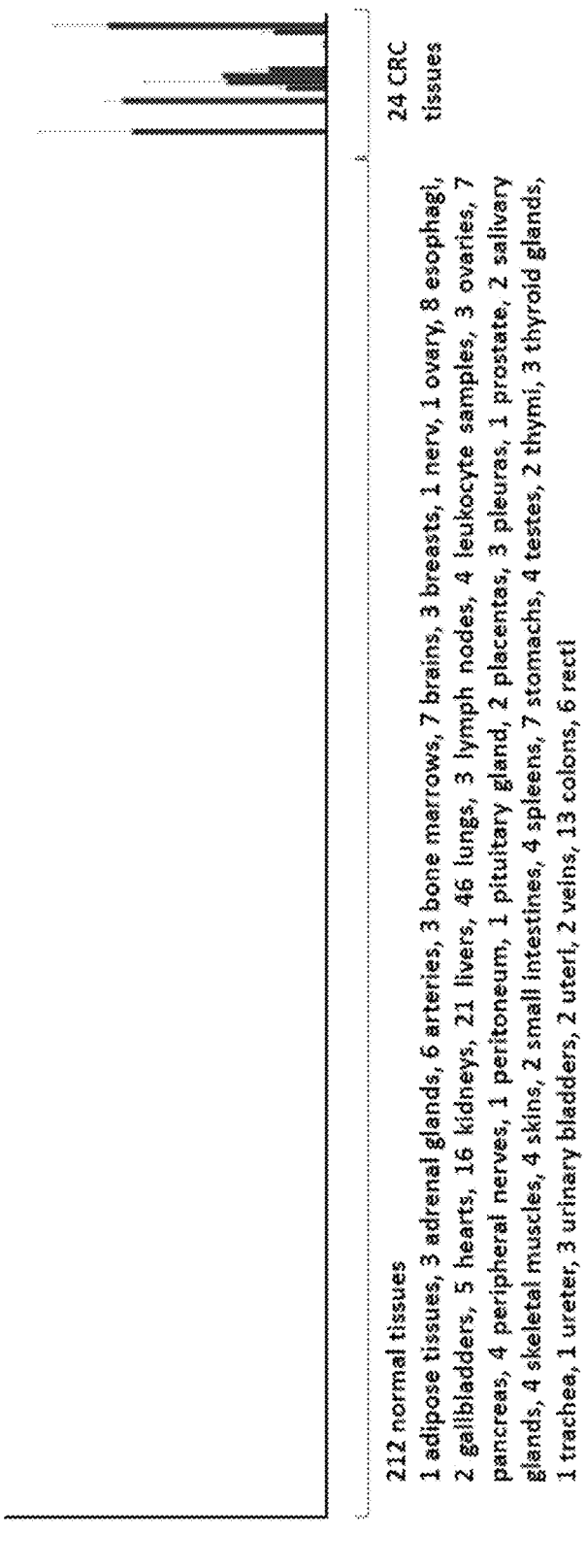
Figure 1B:
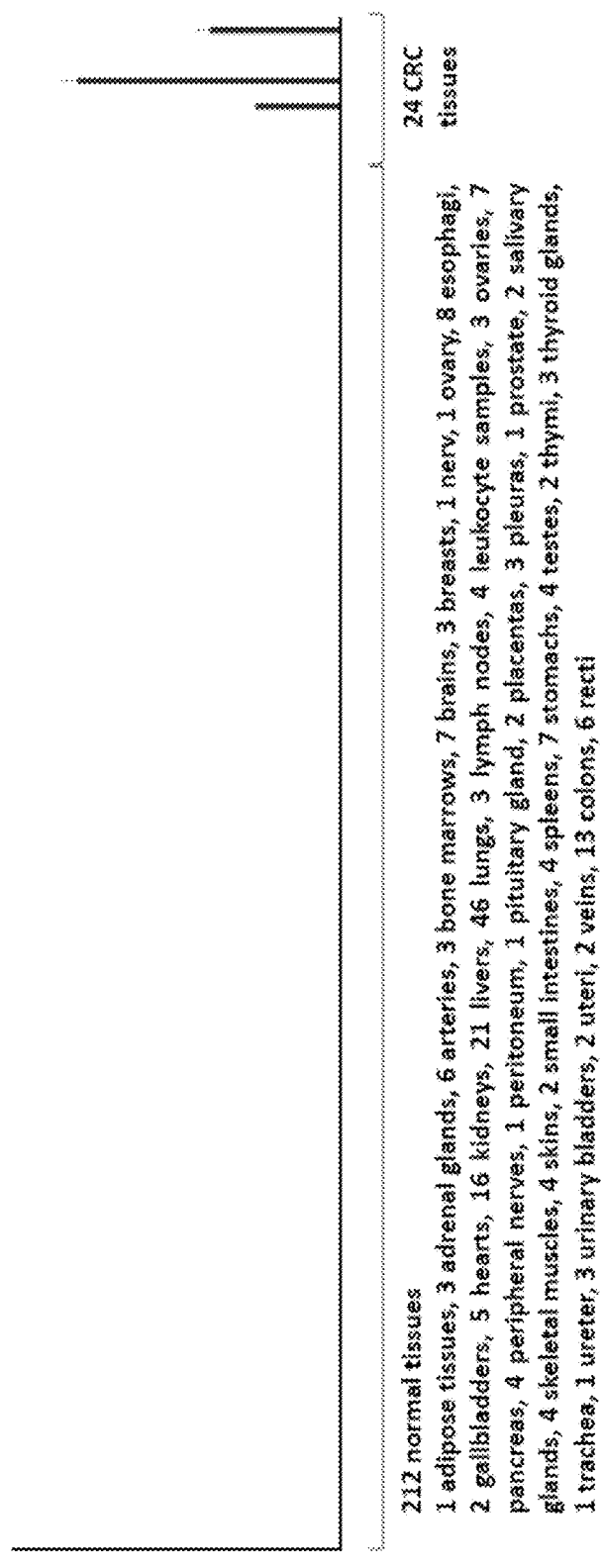
Figure 1C:
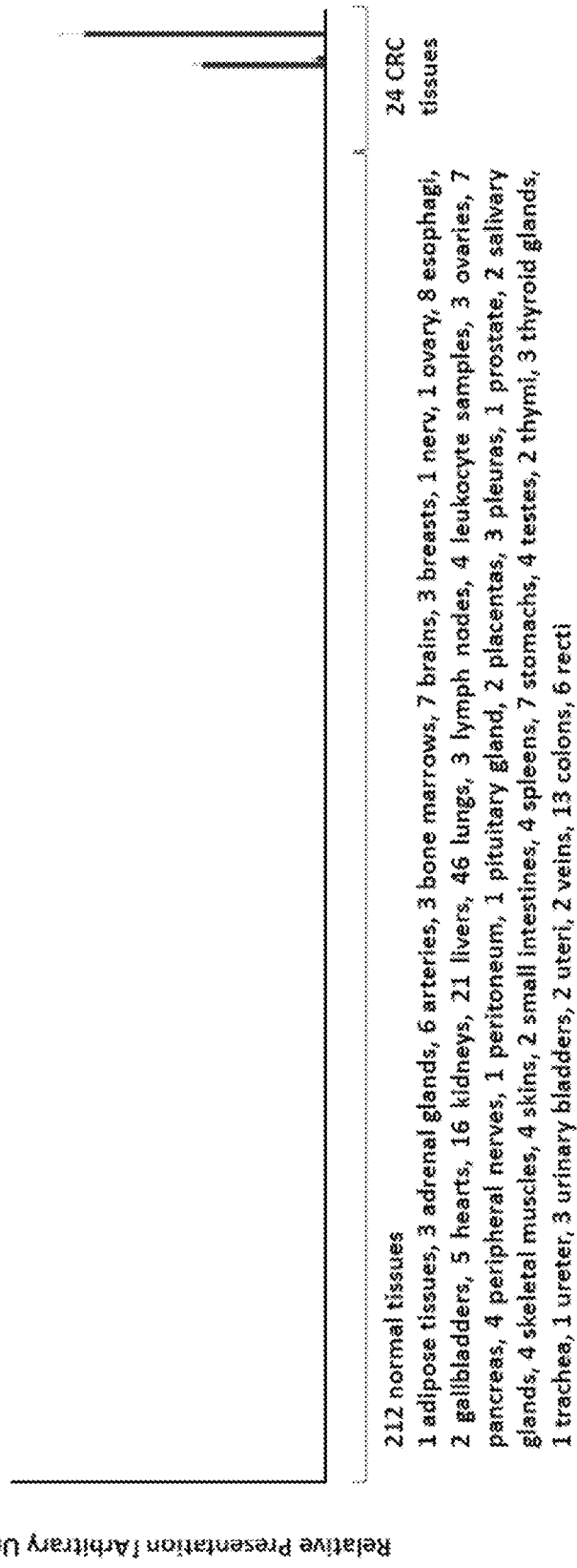
Figure 1D:
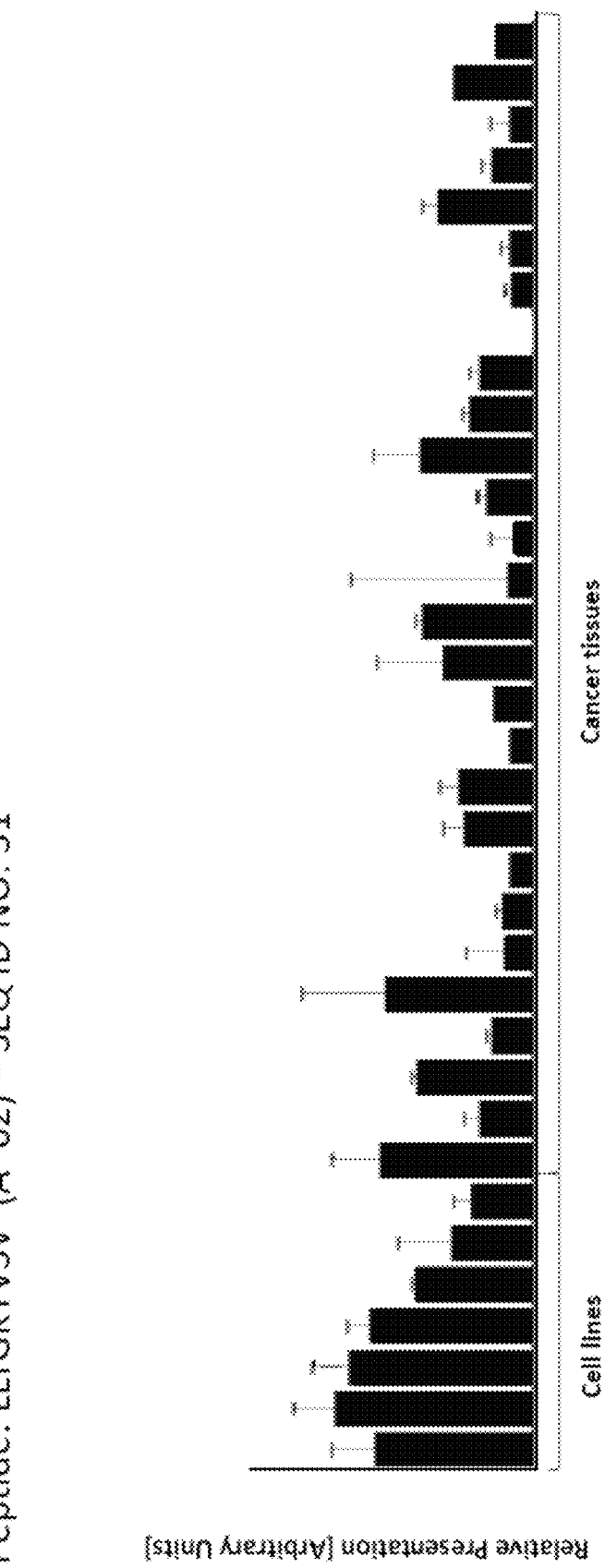
Figure 1F:
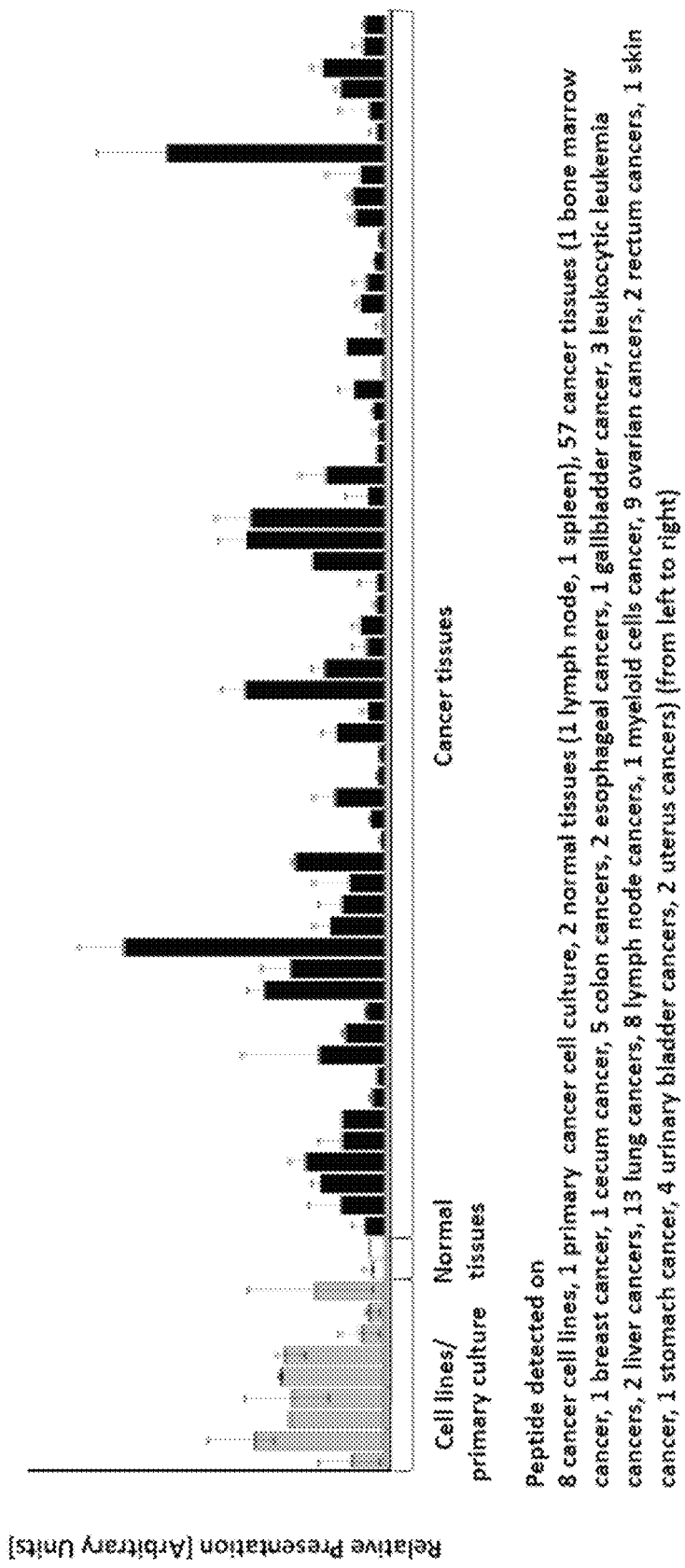

Identification and Quantitation of Tumor Associated Peptides Presented on the Cell Surface
Tissue Samples Patients' tumor tissues were obtained from University Hospital of Tübingen.

Normal tissues were obtained from Asterand, Detroid, USA and Royston, Herts, UK; Bio-Options Inc, CA, USA; BioServe, Beltsville, Md., USA; Capital BioScience Inc, Rockville, Md., USA; Geneticist Inc., Glendale, Calif., USA; Tissue Solutions Ltd, Glasgow, Scotland, UK; University Hospital of Geneva; University Hospital of Heidelberg; Kyoto Prefectural University of Medicine (KPUM); University Hospital Munich; ProteoGenex Inc., Culver City, Calif., USA; University Hospital of Tübingen. Written informed consents of all patients had been given before surgery or autopsy. Tissues were shock-frozen immediately after excision and stored until isolation of TUMAPs at −70° C. or below.
Isolation of HLA Peptides from Tissue Samples HLA peptide pools from shock-frozen tissue samples were obtained by immune precipitation from solid tissues according to a slightly modified protocol (Falk et al., 1991; Seeger et al., 1999) using the HLA-A*02-specific antibody BB7.2, the HLA-A, -B, C-specific antibody W6/32, CNBr-activated sepharose, acid treatment, and ultrafiltration.
Mass Spectrometry Analyses The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 μm i.d.× 250 mm) packed with 1.7 μm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOPS strategy. In brief, a scan cycle was initiated with a full scan of high mass accuracy in the orbitrap (R=30 000), which was followed by MS/MS scans also in the orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose CRC samples to a baseline of normal tissue samples. Presentation profiles of exemplary over-presented peptides are shown in FIGS. 1A-1M. Presentation scores for exemplary peptides are shown in Table 8.

TABLE 8

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+).

| SEQ ID No. | Sequence | PeptidePresentation |
|---|---|---|
| 1 | ALIKQLFEA | +++ |
| 2 | ALLPRYFFL | +++ |
| 3 | RLIPDTLYSV | +++ |
| 4 | RLAELTVDEFL | +++ |
| 5 | WLFDDGGLTL | +++ |
| 6 | FLAELPGSLSL | + |
| 7 | YLTRHLAVL | +++ |
| 8 | ALMLQGVDLL | +++ |
| 9 | ILDDHLSRV | +++ |
| 10 | RMYNKIFAI | +++ |
| 11 | YLFEKTFNM | +++ |

TABLE 8-continued

Presentation scores. The table lists peptides
that are very highly over-presented on tumors
compared to a panel of normal tissues (+++),
highly over-presented on tumors compared
to a panel of normal tissues (++) or
over-presented on tumors compared to a
panel of normal tissues (+).

| SEQ ID No. | Sequence | PeptidePresentation |
|---|---|---|
| 12 | ALVQGILERV | +++ |
| 13 | FLLAEDTKV | +++ |
| 15 | LQLDKEFQL | + |
| 16 | VLVDQSWVL | +++ |
| 17 | ALAAARVEL | +++ |
| 18 | FLSSLKGGLL | +++ |
| 19 | RLYTKLLNEA | +++ |
| 21 | VLIDHRWVL | +++ |
| 22 | GLIDEVMVL | +++ |
| 23 | FLDANGHFV | + |
| 25 | SLADRLIGV | +++ |
| 26 | GLASKENFSNVSL | +++ |
| 27 | LLADEDSSYL | +++ |
| 30 | GLSSAYGGL | +++ |
| 31 | LLYGKYVSV | +++ |
| 32 | KLNTETFGV | +++ |
| 33 | ALWEKNTHL | +++ |
| 34 | ILLEKSVSV | +++ |
| 35 | KLLDLTVRI | +++ |
| 36 | GLLESPSIFNFTA | +++ |
| 37 | GLFAGLGGAGA | +++ |
| 38 | SLAPTPVSA | +++ |
| 39 | GLNGGSPAAA | +++ |
| 40 | ALSNVIHKV | +++ |
| 41 | ILDDSFKLL | ++ |
| 42 | SILDDSFKL | +++ |
| 43 | TLDAAQPRV | ++ |
| 44 | SLESKLTSV | +++ |
| 45 | ALAELLHGA | +++ |
| 46 | GLDDRYSLV | + |
| 47 | KLYERCEVV | ++ |
| 48 | FLDASDPAL | +++ |
| 51 | QVWEIQHTV | ++ |
| 53 | FLLGSEIKL | ++ |
| 54 | ALLNGEYLLAA | + |
| 56 | VLFTDEGVPKFL | + |
| 57 | NLLEKENYL | ++ |
| 58 | AMADKMDMSL | + |
| 59 | LLTDNVVKL | + |
| 60 | VLDEDEPRFL | + |
| 61 | KLLKLFQGV | +++ |
| 62 | YLAPENGYL | ++ |
| 63 | KLFSILSTV | + |
| 64 | KTLGKLWRL | +++ |
| 65 | FGAPGIISA | +++ |
| 66 | GLDDGPDFL | + |
| 67 | SLNDLEKDVMLL | + |
| 68 | SILQFVHMV | ++ |
| 69 | GMLNEAEGKAIKL | + |
| 70 | MISELEVRL | + |
| 71 | RLWTEIPTAI | ++ |
| 72 | YLLDYPNNLL | ++ |
| 73 | YLFDIAVSM | ++ |
| 74 | YLMGFLHAV | ++ |
| 75 | EMIENIQSV | + |
| 77 | SLLKRDFGA | + |
| 78 | ALDPELLLL | + |
| 80 | QVDEVVDIMRV | ++ |
| 81 | ALLSQQTHL | ++ |
| 82 | QLYEEPDTKL | ++ |
| 83 | LTIEDGIFEV | + |
| 88 | KLDIKVETV | + |
| 89 | SLIEYEFRV | ++ |
| 90 | GLLKPGLNVVL | + |
| 92 | WIDDTSAFV | +++ |
| 93 | SLQELRLLL | + |
| 95 | AILDAHIEV | + |
| 96 | KLYSRLVYV | ++ |
| 97 | ALWWGVVTV | ++ |
| 100 | SLDDFLATA | + |

TABLE 8-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+).

| SEQ ID No. | Sequence | PeptidePresentation |
|---|---|---|
| 102 | KILVSLIEV | +++ |
| 103 | FLFGYPKRL | + |
| 110 | LLGELPRLLLL | + |
| 111 | HMDDGGYSM | + |
| 112 | KLGQVLIYL | +++ |
| 113 | ILYDLQQNL | + |
| 123 | KTLERSYLL | +++ |
| 124 | RVLPPSALQSV | ++ |
| 125 | KLGDFGLLVEL | +++ |
| 126 | TLAKYLMEL | +++ |
| 127 | RLAELTVDEFLA | +++ |
| 128 | MLDDRAYLV | ++ |
| 129 | VLIDVLKEL | +++ |
| 130 | GLGGSQLIDTHL | +++ |
| 131 | KLLDVVHPA | +++ |
| 132 | ALLNAILHSA | +++ |
| 133 | RTFEKIEEV | +++ |
| 134 | GVAGGSILKGV | +++ |
| 135 | KLQEEIPVL | +++ |
| 136 | KLFDIFSQQV | +++ |
| 137 | QLTEIKPLL | +++ |
| 138 | KQFEGTVEI | +++ |
| 139 | VLLNEILEQV | + |
| 141 | AVIEHLERL | +++ |
| 142 | SLVQRVETI | +++ |
| 143 | KLSDVWKEL | +++ |
| 144 | LLNDRIWLA | + |
| 145 | LLLEVVKQV | +++ |
| 146 | ALSDETWGL | + |
| 148 | RLLENMTEVV | ++ |
| 150 | RLADLEALKV | +++ |
| 152 | KLLAVIHEL | + |
| 153 | ILFSEDSTKLFV | + |
| 154 | KLPSETIFVGC | + |
| 155 | RLLGEEVVRV | ++ |

TABLE 8-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+).

| SEQ ID No. | Sequence | PeptidePresentation |
|---|---|---|
| 156 | SLMMTIINL | ++ |
| 157 | SLIERDLKL | ++ |
| 158 | GLLDPSVFHV | +++ |
| 159 | VLVDDDGIKVV | +++ |
| 160 | KLLEFDQLQL | ++ |
| 161 | FLKNELDNV | ++ |
| 162 | KLMDYIDEL | ++ |
| 163 | RLLHEVQEL | ++ |
| 164 | KMLDEILLQL | ++ |
| 165 | RLLDFPEAMVL | +++ |
| 166 | GLLEARGILGL | + |
| 168 | GLIRFPLMTI | ++ |
| 170 | ALAGGITMV | ++ |
| 171 | RLQETEGMVAV | + |
| 172 | LLLDTVTMQV | + |
| 173 | KLGDLMVLL | + |
| 177 | ALLQGAIESV | + |
| 178 | YLFREPATI | + |
| 179 | RLLJPLSSA | + |
| 180 | NLLEIAPHL | ++ |
| 183 | TLQEVVTGV | + |
| 185 | VLYTGVVRV | + |
| 186 | KMSEKILLL | + |
| 187 | GLHNVVYGI | ++ |
| 188 | FLVDGPRVQL | + |
| 192 | KIQEMQHFL | +++ |
| 193 | KLSPTVVGL | +++ |
| 194 | SLYKGLLSV | +++ |
| 195 | LLLGERVAL | +++ |
| 198 | VLYGPDVPTI | ++ |
| 199 | FLLEREQLL | +++ |
| 201 | GJFNGALAAV | +++ |
| 202 | GLAALAVHL | +++ |
| 203 | KLIDLSQVMYL | + |
| 204 | KLLDLETERILL | ++ |

TABLE 8-continued

Presentation scores. The table lists peptides
that are very highly over-presented on tumors
compared to a panel of normal tissues (+++),
highly over-presented on tumors compared
to a panel of normal tissues (++) or
over-presented on tumors compared to a
panel of normal tissues (+).

| SEQ ID No. | Sequence | PeptidePresentation |
|---|---|---|
| 205 | RLHDENILL | +++ |
| 206 | RIAGIRGIQGV | ++ |
| 207 | KLCEGFNEV | +++ |
| 208 | RLIDRIKTV | +++ |
| 209 | KLQDGLLHI | +++ |
| 210 | KLAVALLAA | +++ |
| 211 | SLFGKKYIL | +++ |
| 213 | LLWAPTAQA | +++ |
| 214 | SVLEKEIYSI | +++ |
| 215 | KLQEKIQEL | +++ |
| 216 | YLWDLDHGFAGV | +++ |
| 217 | KLLDTMVDTFL | ++ |
| 218 | KLSWDLIYL | + |
| 220 | KMDPVAYRV | + |
| 221 | ILNVDGLIGV | + |
| 223 | VLMQDSRLYL | +++ |
| 224 | QLQEGKNVIGL | +++ |
| 225 | YLYGQTTTYL | + |
| 226 | FLVDGSWSV | + |
| 227 | LTAPPEALLMV | ++ |
| 228 | SMSGYDQVL | + |
| 229 | YLLEKFVAV | ++ |
| 230 | AMSSKFFLV | ++ |
| 231 | RLFADILNDV | +++ |
| 232 | RLLDSVSRL | + |
| 233 | RLDDLKMTV | ++ |
| 234 | KMFESFIESV | ++ |
| 235 | LLHEENFSV | ++ |
| 236 | KMSELQTYV | + |
| 237 | KLVEFDFLGA | ++ |
| 238 | NMLEAVHTI | ++ |
| 239 | QLIEKNWLL | +++ |
| 240 | VLAPRVLRA | ++ |
| 241 | ILIDWLVQV | + |
| 242 | RLEEDDGDVAM | ++ |
| 243 | TLMDMRLSQV | + |
| 244 | SLHFLILYV | + |
| 245 | QLIDYERQL | + |
| 246 | GLTDNIHLV | + |
| 247 | SLDTLMTYV | + |
| 249 | ALYGRLEVV | + |
| 250 | ALCEENMRGV | + |
| 252 | YVYQNNIYL | + |
| 254 | VLFQEALWHV | ++ |
| 257 | SLADFMQEV | ++ |
| 259 | ALADKELLPSV | + |
| 261 | YLYDSETKNA | + |

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; Bio-Chain, Hayward, Calif., USA). The RNA from several individuals (between 2 and 123 individuals) was mixed such that RNA from each individual was equally weighted.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 µg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalization, 100 housekeeping genes provided by Affymetrix were used. Relative expression values were calculated from the signal log ratios given by the software and the normal kidney sample was arbitrarily set to 1.0. Exemplary expression profiles of source genes of the present invention that are highly over-expressed or exclusively expressed in CRC are shown in FIGS. 2A-2D. Expression scores for further exemplary genes are shown in Table 9.

TABLE 9

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+).

| SEQ ID NO. | Gene Name | Sequence | Gene Expression |
|---|---|---|---|
| 2 | ATP10B | ALLPRYFFL | +++ |
| 5 | SLC12A1, SLC12A2, SLC12A3 | WLFDDGGLTL | +++ |
| 6 | PLAGL2 | FLAELPGSLSL | +++ |
| 7 | MUC2 | YLTRHLAVL | + |
| 8 | HSPD1 | ALMLQGVDLL | + |
| 13 | SMC2 | FLLAEDTKV | +++ |
| 16 | KLK10 | VLVDQSWVL | + |
| 17 | SLC12A2 | ALAAARVEL | +++ |
| 19 | MYO10 | RLYTKLLNEA | +++ |
| 27 | CHMP5 | LLADEDSSYL | ++ |
| 29 | AP3D1 | QMLDVAIRV | + |
| 35 | OLFM4 | KLLDLTVRI | + |
| 36 | LARP4B | GLLESPSIFNFTA | + |
| 39 | CDX2 | GLNGGSPAAA | ++ |
| 40 | SERPINB5 | ALSNVIHKV | + |
| 41 | HEPH | ILDDSFKLL | ++ |
| 42 | HEPH | SILDDSFKL | ++ |
| 46 | PKP3 | GLDDRYSLV | + |
| 47 | ERBB3 | KLYERCEVV | + |
| 53 | TBC1D8B | FLLGSEIKL | + |
| 55 | PMS1 | QIITSVVSV | ++ |
| 57 | PKP2 | NLLEKENYL | ++ |
| 60 | AGTPBP1 | VLDEDEPRFL | + |
| 63 | HEATR2 | KLFSILSTV | ++ |
| 64 | SOX8, SOX9, SOX10 | KTLGKLWRL | ++ |
| 67 | SMARCA4 | SLNDLEKDVMLL | ++ |
| 68 | PTPRO | SILQFVHMV | + |
| 73 | APIP | YLFDIAVSM | + |
| 74 | ARHGAP8, PRR5-ARHGAP8, PRR5 | YLMGFLHAV | + |
| 75 | CFTR | EMIENIQSV | +++ |
| 77 | DDX5 | SLLKRDFGA | + |
| 79 | SRSF11 | SLAADQLLKL | ++ |
| 81 | TGIF1 | ALLSQQTHL | + |
| 84 | DSP | SMVEDITGLRL | + |
| 86 | MUC13 | KVFPGKISV | +++ |
| 89 | ITGA6 | SLIEYEFRV | ++ |
| 90 | EBNA1BP2 | GLLKPGLNVVL | ++ |
| 92 | PARN | WIDDTSAFV | + |
| 98 | ATP13A3 | AMNGKSFSV | +++ |
| 104 | MUC2 | ILLTIKDDTIYL | + |
| 112 | GALNT7 | KLGQVLIYL | ++ |
| 113 | KCNN4 | ILYDLQQNL | + |
| 123 | RRM1 | KTLERSYLL | +++ |
| 124 | AURKB | RVLPPSALQSV | ++ |
| 126 | CCNB1, CCNB2 | TLAKYLMEL | +++ |
| 129 | CNOT1 | VLIDVLKEL | + |
| 130 | PRRC2C | GLGGSQLIDTHL | ++ |
| 132 | NOL11 | ALLNAILHSA | ++ |
| 134 | EIF2S3, LOC255308 | GVAGGSILKGV | + |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+).

| SEQ ID NO. | Gene Name | Sequence | Gene Expression |
|---|---|---|---|
| 135 | CENPE | KLQEEIPVL | + |
| 138 | BRCA2 | KQFEGTVEI | ++ |
| 139 | NCAPG | VLLNEILEQV | +++ |
| 140 | NCAPG | LLNEILEQV | +++ |
| 142 | ECT2 | SLVQRVETI | ++ |
| 144 | ZSWIM1 | LLNDRIWLA | ++ |
| 147 | KDM5C | TLTELRAFL | + |
| 148 | PDXDC1 | RLLENMTEVV | + |
| 152 | RAD54B | KLLAVIHEL | + |
| 156 | TOP2A | SLMMTIINL | +++ |
| 157 | URB1 | SLIERDLKL | + |
| 160 | SYNJ2 | KLLEFDQLQL | + |
| 161 | TRAIP | FLKNELDNV | + |
| 166 | CDC6 | GLLEARGILGL | + |
| 171 | HMGXB4 | RLQETEGMVAV | + |
| 172 | COPG1 | LLLDTVTMQV | + |
| 180 | GPD2 | NLLEIAPHL | + |
| 183 | AGK | TLQEVVTGV | ++ |
| 184 | PRKDC | SLLDENNVSSYL | + |
| 187 | CNOT1 | GLHNVVYGI | + |
| 188 | ZSWIM1 | FLVDGPRVQL | ++ |
| 190 | NCAPD2 | AMAEMVLQV | + |
| 191 | CDK5RAP2 | QLFSEIHNL | + |
| 192 | MMP12 | KIQEMQHFL | ++ |
| 194 | RAD54B | SLYKGLLSV | + |
| 197 | ZNF451 | SLFGQDVKAV | + |
| 198 | CEACAM6 | VLYGPDVPTI | ++ |
| 202 | FANCA | GLAALAVHL | ++ |
| 204 | GOLGA4 | KLLDLETERILL | + |
| 205 | RPGRIP1L | RLHDENILL | + |
| 206 | EFR3A | RIAGIRGIQGV | + |
| 208 | NAA35 | RLIDRIKTV | + |
| 215 | CENPE | KLQEKIQEL | + |
| 219 | MUC2 | FLDEKGRCV | + |
| 223 | CDK1 | VLMQDSRLYL | +++ |
| 225 | TOP2A | YLYGQTTTYL | +++ |
| 228 | HNRNPH1, HNRNPH2 | SMSGYDQVL | +++ |
| 229 | DDX11, DDX12P, LOC642846 | YLLEKFVAV | + |
| 230 | WNT5A | AMSSKFFLV | + |
| 232 | LAMC2 | RLLDSVSRL | ++ |
| 233 | LAMC2 | RLDDLKMTV | ++ |
| 235 | TCF20 | LLHEENFSV | + |
| 236 | CENPF | KMSELQTYV | ++ |
| 239 | KIF15 | QLIEKNWLL | +++ |
| 240 | RCN1 | VLAPRVLRA | ++ |
| 241 | CCNB1 | ILIDWLVQV | +++ |
| 250 | EEF2 | ALCEENMRGV | + |
| 257 | CNOT1 | SLADFMQEV | + |

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T-cells with artificial antigen presenting cells (aAPCs) loaded with peptide/MHC complexes and anti-CD28 antibody. This way the inventors could show immunogenicity for 22 HLA-A*0201 restricted TUMAPs of the invention so far, demonstrating that these peptides are T-cell epitopes against which CD8+ precursor T-cells exist in humans (Table 10).

In Vitro Priming of CD8+ T-Cells

In order to perform in vitro stimulations by artificial antigen presenting cells loaded with peptide-MHC complex (pMHC) and anti-CD28 antibody, the inventors first isolated CD8+ T-cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 266) from modified Melan-A/MART-1) and A*0201/DDX5-001 (YLLPAIVHI from DDX5, SEQ ID NO. 267), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating 1×10$^6$ CD8+ T-cells with 2×10$^6$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oreg., USA). In vitro priming of specific multimer+CD8+ lymphocytes was detected by by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+cells was at least 10× the median of the negative control stimulations).

In Vitro Immunogenicity for CRC Peptides

Figure 3:
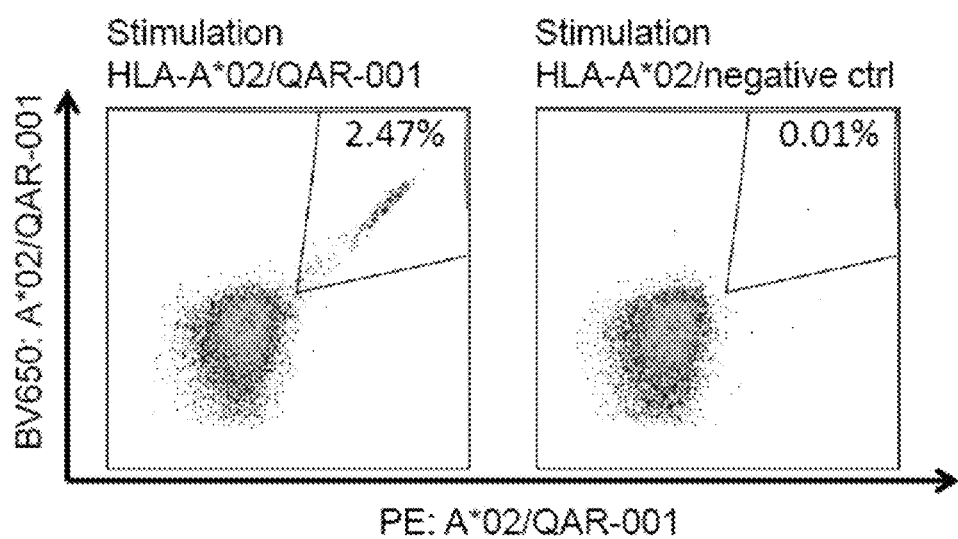
FIG. 3 shows exemplary immunogenicity data: flow cytometry results after peptide-specific multimer staining.

For tested HLA class I peptides, in vitro immunogenicity could be demonstrated by generation of peptide specific T-cell lines. Exemplary flow cytometry results after TUMAP-specific multimer staining for 1 peptide of the invention are shown in FIG. 3 together with corresponding negative controls. Results for 2 peptides from the invention are summarized in Table 10A.

TABLE 10A in vitro immunogenicity of HLA class I peptides of the invention Exemplary results of in vitro immunogenicity experiments conducted by the applicant for the peptides of the invention.

| Seq ID | Peptide ID | wells | donors |
|---|---|---|---|
| 219 | MUC2-001 | ++ | +++ |
| 220 | QAR-001 | +++ | ++++ |

<20% = +;
20%-49% = ++;
50%-69% = +++;
>=70% = ++++

TABLE 10B

Additional data for in vitro immunogenicity of HLA class I peptides of the invention. Exemplary results of in vitro immunogenicity experiments conducted by the applicant for HLA-A*02 restricted peptides of the invention. Results of in vitro immunogenicity experiments are indicated. Percentage of positive wells and donors (among evaluable) are summarized as indicated <20% = +; 20%-49% = ++; 50%-69% = +++; >=70% = ++++

| SEQ ID NO | Sequence | Wells positive [%] |
|---|---|---|
| 1 | ALIKQLFEA | "+" |
| 2 | ALLPRYFFL | "++++" |
| 3 | RLIPDTLYSV | "+++" |
| 5 | WLFDDGGLTL | "++" |
| 7 | YLTRHLAVL | "+" |
| 9 | ILDDHLSRV | "+" |
| 10 | RMYNKIFAI | "++++" |
| 11 | YLFEKTFNM | "+" |
| 12 | ALVQGILERV | "++++" |
| 13 | FLLAEDTKV | "++" |
| 17 | ALAAARVEL | "++" |
| 18 | FLSSLKGGLL | "+" |
| 19 | RLYTKLLNEA | "+++" |
| 21 | VLIDHRWVL | "+" |
| 22 | GLIDEVMVL | "++" |
| 31 | LLYGKYVSV | "++" |
| 32 | KLNTETFGV | "++" |
| 37 | GLFAGLGGAGA | "+" |
| 38 | SLAPTPVSA | "+" |
| 42 | SILDDSFKL | "+" |
| 47 | KLYERCEVV | "+" |
| 59 | LLTDNVVKL | "+" |
| 64 | KTLGKLWRL | "++++" |
| 123 | KTLERSYLL | "+" |
| 124 | RVLPPSALQSV | "+" |

TABLE 10B-continued

Additional data for in vitro immunogenicity of HLA class I peptides of the invention. Exemplary results of in vitro immunogenicity experiments conducted by the applicant for HLA-A*02 restricted peptides of the invention. Results of in vitro immunogenicity experiments are indicated. Percentage of positive wells and donors (among evaluable) are summarized as indicated <20% = +; 20%-49% = ++; 50%-69% = +++; >=70% = ++++

| SEQ ID NO | Sequence | Wells positive [%] |
|---|---|---|
| 127 | RLAELTVDEFLA | "+" |
| 132 | ALLNAILHSA | "+" |
| 133 | RTFEKIEEV | "+" |
| 136 | KLFDIFSQQV | "++" |
| 141 | AVIEHLERL | "+" |
| 142 | SLVQRVETI | "+" |
| 150 | RLADLEALKV | "++" |

Example 4

Synthesis of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizates (trifluoro acetate salt) in purities of >50%. All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko et al., 2006).

96 well MAXISorp plates (NUNC) were coated over night with 2 ug/ml streptavidin in PBS at room temperature, washed 4× and blocked for 1 h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 ug/ml HRP conjugated anti-β2m for 1 h at 37° C., washed again and detected with TMB solution that is stopped with NH2SO4. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 11

MHC class I binding scores. Binding of HLA-class I restricted peptides to HLA-A*02:01 was ranged by peptide exchange yield: ≥10% = +; ≥20% = ++; ≥50 = +++; ≥75% = ++++; J = Phosphoserine

| SEQ ID NO | Sequence | Peptide exchange |
|---|---|---|
| 1 | ALIKQLFEA | "+++" |
| 2 | ALLPRYFFL | "++" |
| 3 | RLIPDTLYSV | "++++" |
| 4 | RLAELTVDEFL | "+++" |
| 5 | WLFDDGGLTL | "++++" |
| 6 | FLAELPGSLSL | "+++" |
| 7 | YLTRHLAVL | "++" |
| 8 | ALMLQGVDLL | "+++" |
| 9 | ILDDHLSRV | "++" |
| 10 | RMYNKIFAI | "+++" |
| 11 | YLFEKTFNM | "+++" |
| 12 | ALVQGILERV | "+++" |
| 13 | FLLAEDTKV | "+++" |
| 14 | FLDKPEDVLL | "++" |
| 15 | LQLDKEFQL | "+++" |
| 16 | VLVDQSWVL | "+++" |
| 17 | ALAAARVEL | "+++" |
| 18 | FLSSLKGGLL | "+++" |
| 19 | RLYTKLLNEA | "+++" |
| 20 | YLKDGDVML | "+++" |
| 21 | VLIDHRWVL | "+++" |
| 22 | GLIDEVMVL | "+++" |
| 23 | FLDANGHFV | "+++" |
| 24 | VLDGVLMEL | "+++" |
| 25 | SLADRLIGV | "++++" |
| 26 | GLASKENFSNVSL | "++" |
| 27 | LLADEDSSYL | "++" |
| 28 | ALTEIQEFI | "++++" |
| 29 | QMLDVAIRV | "+++" |
| 30 | GLSSAYGGL | "+" |
| 31 | LLYGKYVSV | "+++" |
| 32 | KLNTETFGV | "++" |
| 33 | ALWEKNTHL | "+++" |

TABLE 11-continued

MHC class I binding scores. Binding of HLA-class I restricted peptides to HLA-A*02:01 was ranged by peptide exchange yield: ≥10% = +; ≥20% = ++; ≥50 = +++; ≥75% = ++++; J = Phosphoserine

| SEQ ID NO | Sequence | Peptide exchange |
|---|---|---|
| 34 | ILLEKSVSV | "+++" |
| 35 | KLLDLTVRI | "+++" |
| 36 | GLLESPSIFNFTA | "+++" |
| 37 | GLFAGLGGAGA | "+++" |
| 38 | SLAPTPVSA | "++" |
| 40 | ALSNVIHKV | "++" |
| 41 | ILDDSFKLL | "++" |
| 42 | SILDDSFKL | "++++" |
| 43 | TLDAAQPRV | "++" |
| 44 | SLESKLTSV | "+++" |
| 45 | ALAELLHGA | "+++" |
| 46 | GLDDRYSLV | "+++" |
| 47 | KLYERCEVV | "++" |
| 48 | FLDASDPAL | "++" |
| 50 | TLMAEMHVV | "+++" |
| 51 | QVWEIQHTV | "++" |
| 52 | ALDSSNSMQTI | "++" |
| 53 | FLLGSEIKL | "+++" |
| 54 | ALLNGEYLLAA | "+++" |
| 56 | VLFTDEGVPKFL | "++" |
| 57 | NLLEKENYL | "+++" |
| 58 | AMADKMDMSL | "++" |
| 59 | LLTDNVVKL | "+++" |
| 60 | VLDEDEPRFL | "++" |
| 61 | KLLKLFQGV | "+++" |
| 62 | YLAPENGYL | "++" |
| 63 | KLFSILSTV | "++" |
| 64 | KTLGKLWRL | "++" |
| 66 | GLDDGPDFL | "++" |
| 67 | SLNDLEKDVMLL | "+++" |
| 68 | SILQFVHMV | "+++" |
| 69 | GMLNEAEGKAIKL | "++" |
| 70 | MISELEVRL | "+++" |
| 71 | RLWTEIPTAI | "+++" |
| 72 | YLLDYPNNLL | "+++" |
| 73 | YLFDIAVSM | "+++" |
| 74 | YLMGFLHAV | "+++" |
| 75 | EMIENIQSV | "++" |
| 76 | YLIGEKQHYL | "+++" |
| 77 | SLLKRDFGA | "++" |
| 78 | ALDPELLLL | "++" |
| 79 | SLAADQLLKL | "++" |
| 80 | QVDEVVDIMRV | "++" |
| 81 | ALLSQQTHL | "+++" |
| 82 | QLYEEPDTKL | "++" |
| 83 | LTIEDGIFEV | "+++" |
| 84 | SMVEDITGLRL | "+++" |
| 85 | ILHDINSDGVL | "++" |
| 86 | KVFPGKISV | "++" |
| 87 | LLFDAPDLRL | "+++" |
| 88 | KLDIKVETV | "++++" |
| 89 | SLIEYEFRV | "+++" |
| 90 | GLLKPGLNVVL | "+++" |
| 91 | TVDVATPSV | "+++" |
| 92 | WIDDTSAFV | "+++" |
| 93 | SLQELRLLL | "++++" |
| 94 | KSMDIVLTV | "+++" |
| 95 | AILDAHIEV | "++++" |
| 96 | KLYSRLVYV | "++" |
| 97 | ALWWGVVTV | "++" |
| 98 | AMNGKSFSV | "++" |
| 99 | KLLEVDLDTV | "+++" |
| 100 | SLDDFLATA | "+++" |
| 101 | GLSEGHTFQV | "+++" |
| 102 | KILVSLIEV | "+++" |
| 103 | FLFGYPKRL | "++" |
| 104 | ILLTIKDDTIYL | "+++" |
| 105 | YALDLSTFL | "+++" |
| 106 | SLISEKILL | "+++" |
| 107 | ALLGGGPYML | "+++" |
| 108 | SLAELVPGVGGI | "+++" |
| 109 | ALDGDQMEL | "++" |

TABLE 11-continued

MHC class I binding scores. Binding of HLA-class I restricted peptides to HLA-A*02:01 was ranged by peptide exchange yield: ≥10% = +; ≥20% = ++; ≥50 = +++; ≥75% = ++++; J = Phosphoserine

| SEQ ID NO | Sequence | Peptide exchange |
|---|---|---|
| 110 | LLGELPRLLLL | "+++" |
| 112 | KLGQVLIYL | "++" |
| 113 | ILYDLQQNL | "++" |
| 114 | TAVGHALVL | "+" |
| 115 | SLFDVSHML | "+++" |
| 116 | LVYQFVHPI | "++" |
| 117 | TLQPVDNSTISL | "++" |
| 118 | LLADLKTMV | "+++" |
| 119 | ILYQTVTGL | "++" |
| 120 | VLYEGVDEV | "++" |
| 121 | SLAPNIISQL | "+++" |
| 122 | SLMGMVLKL | "+++" |
| 123 | KTLERSYLL | "++" |
| 124 | RVLPPSALQSV | "+++" |
| 125 | KLGDFGLLVEL | "++++" |
| 126 | TLAKYLMEL | "+++" |
| 127 | RLAELTVDEFLA | "+++" |
| 128 | MLDDRAYLV | "++" |
| 129 | VLIDVLKEL | "+++" |
| 130 | GLGGSQLIDTHL | "++" |
| 131 | KLLDVVHPA | "++" |
| 132 | ALLNAILHSA | "+++" |
| 133 | RTFEKIEEV | "++" |
| 134 | GVAGGSILKGV | "++++" |
| 135 | KLQEEIPVL | "++" |
| 136 | KLFDIFSQQV | "+++" |
| 137 | QLTEIKPLL | "+++" |
| 138 | KQFEGTVEI | "+++" |
| 139 | VLLNEILEQV | "+++" |
| 140 | LLNEILEQV | "+++" |
| 141 | AVIEHLERL | "++++" |
| 142 | SLVQRVETI | "+++" |
| 143 | KLSDVWKEL | "+++" |
| 144 | LLNDRIWLA | "+++" |
| 145 | LLLEVVKQV | "+++" |
| 146 | ALSDETWGL | "++" |
| 147 | TLTELRAFL | "++++" |
| 148 | RLLENMTEVV | "+++" |
| 149 | YQFDKVGILTL | "+++" |
| 150 | RLADLEALKV | "+++" |
| 151 | SAQGSDVSLTACKV | "+++" |
| 152 | KLLAVIHEL | "++" |
| 153 | ILFSEDSTKLFV | "+++" |
| 154 | KLPSETIFVGC | "+++" |
| 155 | RLLGEEVVRV | "+++" |
| 156 | SLMMTIINL | "++++" |
| 157 | SLIERDLKL | "+++" |
| 158 | GLLDPSVFHV | "+++" |
| 159 | VLVDDDGIKVV | "++" |
| 160 | KLLEFDQLQL | "+++" |
| 161 | FLKNELDNV | "+++" |
| 162 | KLMDYIDEL | "+++" |
| 163 | RLLHEVQEL | "+++" |
| 164 | KMLDEILLQL | "++++" |
| 165 | RLLDFPEAMVL | "++++" |
| 166 | GLLEARGILGL | "+++" |
| 167 | SVIDHIHLISV | "+++" |
| 168 | GLIRFPLMTI | "+++" |
| 169 | YLAHFIEGL | "+++" |
| 170 | ALAGGITMV | "+++" |
| 171 | RLQETEGMVAV | "++" |
| 172 | LLLDTVTMQV | "+++" |
| 173 | KLGDLMVLL | "+++" |
| 174 | ILLDDNMQIRL | "++++" |
| 175 | TLLGGKEAQALGV | "+++" |
| 176 | RTLDKVLEV | "++" |
| 177 | ALLQGAIESV | "+++" |
| 178 | YLFREPATI | "++" |
| 179 | RLLJPLSSA | "+++" |
| 181 | NLFDLGGQYLRV | "+++" |
| 182 | SLNKWIFTV | "++++" |
| 183 | TLQEVVTGV | "+++" |

TABLE 11-continued

MHC class I binding scores. Binding of HLA-class I restricted peptides to HLA-A*02:01 was ranged by peptide exchange yield: ≥10% = +; ≥20% = ++; ≥50 = +++; ≥75% = ++++; J = Phosphoserine

| SEQ ID NO | Sequence | Peptide exchange |
| --- | --- | --- |
| 184 | SLLDENNVSSYL | "+++" |
| 185 | VLYTGVVRV | "+++" |
| 186 | KMSEKILLL | "+++" |
| 187 | GLHNVVYGI | "+++" |
| 188 | FLVDGPRVQL | "+++" |
| 189 | AISEVIGKITA | "+++" |
| 190 | AMAEMVLQV | "+++" |
| 191 | QLFSEIHNL | "++++" |

Example 6

Figure 4A:
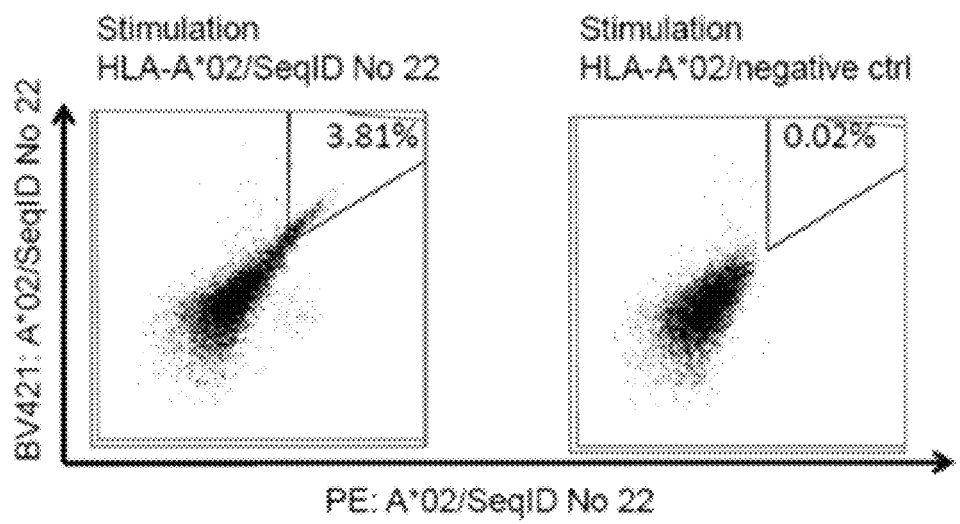
FIGS. 4A to 4C show exemplary results of peptide-specific in vitro CD8+ T cell responses of a healthy HLA-A*02+ donor. CD8+ T cells were primed using artificial APCs coated with anti-CD28 mAb and HLA-A*02 in complex with SeqID No 22 peptide (FIG. 4A, left panel), SeqID No 9 peptide (FIG. 4B, left panel) or SeqID No 142 peptide (FIG. 4C, left panel), respectively. After three cycles of stimulation, the detection of peptide-reactive cells was performed by 2D multimer staining with A*02/SeqID No 22 (A),A*02/SeqID No 9 (FIG. 4B) or A*02/SeqID No 142 (FIG. 4C). Right panels (FIGS. 4A, 4B and 4C) show control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.
Figure 4B:
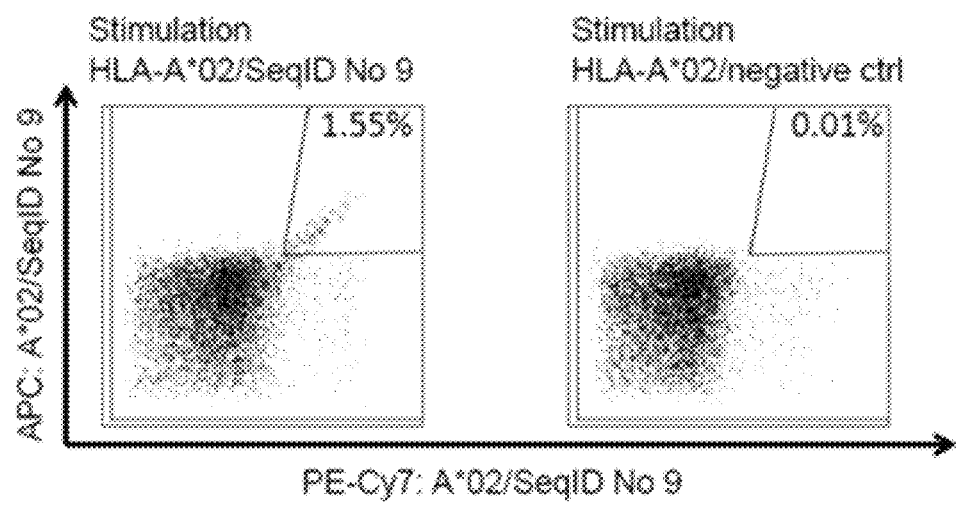
Figure 4C:
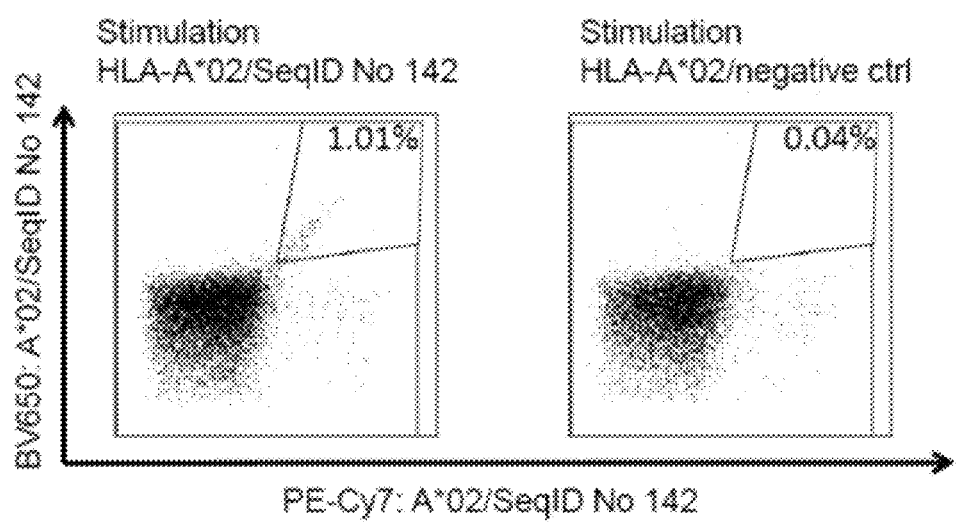

Absolute Quantitation of Tumor Associated Peptides Presented on the Cell Surface The generation of binders, such as antibodies and/or TCRs, is a laborious process, which may be conducted only for a number of selected targets. In the case of tumor-associated and—specific peptides, selection criteria include but are not restricted to exclusiveness of presentation and the density of peptide presented on the cell surface. In addition to the isolation and relative quantitation of peptides as described in EXAMPLE 1, the inventors did analyze absolute peptide copies per cell as described in patent x. The quantitation of TUMAP copies per cell in solid tumor samples requires the absolute quantitation of the isolated TUMAP, the efficiency of TUMAP isolation, and the cell count of the tissue sample analyzed. An overview on our experimental approach is given in FIGS. 4A-4C, experimental steps are described below.

Peptide Quantitation by nanoLC-MS/MS

For an accurate quantitation of peptides by mass spectrometry, a calibration curve was generated for each peptide using the internal standard method. The internal standard is a double-isotope-labelled variant of each peptide, i.e. two isotope-labelled amino acids were included in TUMAP synthesis. It differs from the tumor-associated peptide only in its mass but shows no difference in other physicochemical properties (Anderson et al., 2012). The internal standard was spiked to each MS sample and all MS signals were normalized to the MS signal of the internal standard to level out potential technical variances between MS experiments.

The calibration curves were prepared in at least three different matrices, i.e. HLA peptide eluates from natural samples similar to the routine MS samples, and each preparation was measured in duplicate MS runs. For evaluation, MS signals were normalized to the signal of the internal standard and a calibration curve was calculated by logistic regression.

For the quantitation of tumor-associated peptides from tissue samples, the respective samples were also spiked with the internal standard; the MS signals were normalized to the internal standard and quantified using the peptide calibration curve.

Efficiency of Peptide/MHC Isolation

As for any protein purification process, the isolation of proteins from tissue samples is associated with a certain loss of the protein of interest. To determine the efficiency of TUMAP isolation, peptide/MHC complexes were generated for all TUMAPs selected for absolute quantitation. To be able to discriminate the spiked from the natural peptide/MHC complexes, single-isotope-labelled versions of the TUMAPs were used, i.e. one isotope-labelled amino acid was included in TUMAP synthesis. These complexes were spiked into the freshly prepared tissue lysates, i.e. at the earliest possible point of the TUMAP isolation procedure, and then captured like the natural peptide/MHC complexes in the following affinity purification. Measuring the recovery of the single-labelled TUMAPs therefore allows conclusions regarding the efficiency of isolation of individual natural TUMAPs.

The efficiency of isolation was analyzed in a low number of samples and was comparable among these tissue samples. In contrast, the isolation efficiency differs between individual peptides. This suggests that the isolation efficiency, although determined in only a limited number of tissue samples, may be extrapolated to any other tissue preparation. However, it is necessary to analyze each TUMAP individually as the isolation efficiency may not be extrapolated from one peptide to others.

Determination of the Cell Count in Solid, Frozen Tissue

In order to determine the cell count of the tissue samples subjected to absolute peptide quantitation, the inventors applied DNA content analysis. This method is applicable to a wide range of samples of different origin and, most importantly, frozen samples (Alcoser et al., 2011; Forsey and Chaudhuri, 2009; Silva et al., 2013). During the peptide isolation protocol, a tissue sample is processed to a homogenous lysate, from which a small lysate aliquot is taken. The aliquot is divided in three parts, from which DNA is isolated (QiaAmp DNA Mini Kit, Qiagen, Hilden, Germany). The total DNA content from each DNA isolation is quantified using a fluorescence-based DNA quantitation assay (Qubit dsDNA HS Assay Kit, Life Technologies, Darmstadt, Germany) in at least two replicates.

In order to calculate the cell number, a DNA standard curve from aliquots of single healthy blood cells, with a range of defined cell numbers, has been generated. The standard curve is used to calculate the total cell content from the total DNA content from each DNA isolation. The mean total cell count of the tissue sample used for peptide isolation is extrapolated considering the known volume of the lysate aliquots and the total lysate volume.

Peptide Copies Per Cell

With data of the aforementioned experiments, the inventors calculated the number of TUMAP copies per cell by dividing the total peptide amount by the total cell count of the sample, followed by division through isolation efficiency. Copy cell number for selected peptides are shown in Table 12

TABLE 12

Absolute copy numbers. The table lists the results of absolute peptide quantitation in NSCLC tumor samples. The median number of copies per cell are indicated for each peptide: <100 = +; >=100 = ++; >=1,000 +++; >=10,000 = ++++. The number of samples, in which evaluable, high quality MS data are available, is indicated.

| SEQ ID No. | Peptide Code | Copies per cell (median) | Number of samples |
|---|---|---|---|
| 1 | ZNF-002 | + | 19 |
| 142 | ECT2-001 | + | 18 |
| 22 | CYP2W1-001 | ++ | 23 |
| 152 | RAD54B-002 | +++ | 6 |

REFERENCE LIST

Allison, J. P. et al., Science 270 (1995): 932-933
Andersen, R. S. et al., Nat. Protoc. 7 (2012): 891-902
Appay, V. et al., Eur. J Immunol. 36 (2006): 1805-1814
Banchereau, J. et al., Cell 106 (2001): 271-274
Beatty, G. et al., J Immunol 166 (2001): 2276-2282
Beggs, J. D., Nature 275 (1978): 104-109
Benjamini, Y. et al., Journal of the Royal Statistical Society. Series B (Methodological), Vol. 57 (1995): 289-300
Boulter, J. M. et al., Protein Eng 16 (2003): 707-711
Braumuller, H. et al., Nature (2013)
Brossart, P. et al., Blood 90 (1997): 1594-1599
Bruckdorfer, T. et al., Curr. Pharm. Biotechnol. 5 (2004): 29-43
Card, K. F. et al., Cancer Immunol Immunother. 53 (2004): 345-357
Chanock, S. J. et al., Hum. Immunol. 65 (2004): 1211-1223
Cohen, C. J. et al., J Mol Recognit. 16 (2003a): 324-332
Cohen, C. J. et al., J Immunol 170 (2003b): 4349-4361
Cohen, S. N. et al., Proc. Natl. Acad. Sci. U.S.A 69 (1972): 2110-2114
Coligan J E et al., (1995)
Colombetti, S. et al., J Immunol. 176 (2006): 2730-2738
Dengjel, J. et al., Clin Cancer Res 12 (2006): 4163-4170
Denkberg, G. et al., J Immunol 171 (2003): 2197-2207
Falk, K. et al., Nature 351 (1991): 290-296
Fong, L. et al., Proc. Natl. Acad. Sci. U.S.A 98 (2001): 8809-8814
Gabrilovich, D. I. et al., Nat Med. 2 (1996): 1096-1103
Gattinoni, L. et al., Nat Rev. Immunol 6 (2006): 383-393
Gnjatic, S. et al., Proc Natl. Acad. Sci. U.S.A 100 (2003): 8862-8867
Godkin, A. et al., Int. Immunol 9 (1997): 905-911
Green M R et al., 4th, (2012)
Greenfield E A, 2nd, (2014)
Hwang, M. L. et al., J Immunol. 179 (2007): 5829-5838
Jung, G. et al., Proc Natl Acad Sci USA 84 (1987): 4611-4615
Kibbe A H, rd, (2000)
Krieg, A. M., Nat Rev. Drug Discov. 5 (2006): 471-484
Liddy, N. et al., Nat Med. 18 (2012): 980-987
Ljunggren, H. G. et al., J Exp. Med. 162 (1985): 1745-1759
Longenecker, B. M. et al., Ann N.Y. Acad. Sci. 690 (1993): 276-291
Lukas, T. J. et al., Proc. Natl. Acad. Sci. U.S.A 78 (1981): 2791-2795
Lundblad R L, 3rd, (2004)
Meziere, C. et al., J Immunol 159 (1997): 3230-3237
Morgan, R. A. et al., Science 314 (2006): 126-129
Mori, M. et al., Transplantation 64 (1997): 1017-1027
Mortara, L. et al., Clin Cancer Res. 12 (2006): 3435-3443
Mueller, L. N. et al., J Proteome. Res 7 (2008): 51-61
Mueller, L. N. et al., Proteomics. 7 (2007): 3470-3480
Mumberg, D. et al., Proc. Natl. Acad. Sci. U.S.A 96 (1999): 8633-8638
Pinheiro J et al., (2015)
Plebanski, M. et al., Eur. J Immunol 25 (1995): 1783-1787
Porta, C. et al., Virology 202 (1994): 949-955
Rammensee, H. G. et al., Immunogenetics 50 (1999): 213-219
Rini, B. I. et al., Cancer 107 (2006): 67-74
Rock, K. L. et al., Science 249 (1990): 918-921
Rodenko, B. et al., Nat Protoc. 1 (2006): 1120-1132
Saiki, R. K. et al., Science 239 (1988): 487-491
Seeger, F. H. et al., Immunogenetics 49 (1999): 571-576
Sherman F et al., (1986)
Singh-Jasuja, H. et al., Cancer Immunol. Immunother. 53 (2004): 187-195
Small, E. J. et al., J Clin Oncol. 24 (2006): 3089-3094
Sturm, M. et al., BMC. Bioinformatics. 9 (2008): 163
Teufel, R. et al., Cell Mol Life Sci. 62 (2005): 1755-1762
Tran, E. et al., Science 344 (2014): 641-645
Walter, S. et al., J Immunol 171 (2003): 4974-4978
Walter, S. et al., Nat Med. 18 (2012): 1254-1261
Willcox, B. E. et al., Protein Sci. 8 (1999): 2418-2423
Zaremba, S. et al., Cancer Res. 57 (1997): 4570-4577
Albrecht, M. et al., FEBS Lett. 569 (2004): 18-26
Albulescu, R., Biomark. Med. 7 (2013): 203
Aschauer, H. et al., Wien. Klin. Wochenschr. 95 (1983): 785-788
Aung, P. P. et al., Oncogene 25 (2006): 2546-2557
Backen, A. C. et al., Br. J Cancer 96 (2007): 1544-1548
Bai, J. et al., PLoS. One. 8 (2013b): e59772
Bailey, C. M. et al., J Cell Physiol 209 (2006): 617-624
Baris, O. et al., J Clin Endocrinol. Metab 89 (2004): 994-1005
Becker, T. M. et al., Mol. Cancer 8 (2009): 4
Bie, L. et al., PLoS. One. 6 (2011): e25631
Bilbao-Aldaiturriaga, N. et al., Pediatr. Blood Cancer 62 (2015): 766-769
Boland, A. et al., Nat Struct. Mol. Biol 20 (2013): 1289-1297
Bulk, E. et al., Int. J Cancer 137 (2015): 1306-1317
Cao, R. et al., Br. J Cancer 111 (2014): 539-550
Carvalho, L. et al., Rev Port. Pneumol. 15 (2009): 683-696
Chang, H. Y. et al., PLoS. One. 8 (2013): e54117
Chen, C. H. et al., Oncotarget. 5 (2014a): 6300-6311
Chen, Y. D. et al., Zhonghua Lao. Dong. Wei Sheng Zhi. Ye. Bing. Za Zhi. 30 (2012): 725-729
Chou, C. C. et al., Expert. Rev Mol. Diagn. 8 (2008): 179-187
Chung, F. Y. et al., J Surg. Oncol 102 (2010): 148-153
Cohen, Y. et al., Hematology. 19 (2014): 286-292
Cole, C. L. et al., J Biol Chem 289 (2014): 10488-10501
Courson, D. S. et al., Exp. Cell Res 334 (2015): 10-15
Di, Maro G. et al., J Clin Endocrinol. Metab 99 (2014): E1617-E1626
Ding, K. et al., Med. Hypotheses 83 (2014): 359-364
Doherty, J. A. et al., Cancer Epidemiol. Biomarkers Prev. 20 (2011): 1873-1882
Duursma, A. et al., Mol. Cell Biol 25 (2005): 6937-6947
Egloff, A. M. et al., Cancer Res 66 (2006): 6-9
Fan, C. G. et al., Oncol Rep. 26 (2011): 1281-1286
Fang, Y. et al., Cancer Biol Ther. 15 (2014): 1268-1279

Fang, Z. et al., J Biol Chem 288 (2013): 7918-7929
Fang, Z. Q. et al., Genet. Mol Res 12 (2013): 1479-1489
Feng, B. et al., J Gastroenterol. Hepatol. 21 (2006): 1596-1603
Ferreras, C. et al., J Biol Chem 287 (2012): 36132-36146
Fields, A. P. et al., Adv. Enzyme Regul. 50 (2010): 190-200
Flanagan, J. M. et al., Mol. Cancer Ther. 8 (2009): 249-260
Freed, E. F. et al., PLoS. Genet. 8 (2012): e1002892
Goldenson, B. et al., Oncogene 34 (2015): 537-545
Gomez, A. et al., Mol. Pharmacol. 78 (2010): 1004-1011
Griffin, J. N. et al., PLoS. Genet. 11 (2015): e1005018
Gutierrez-Camino, A. et al., Pediatr. Res 75 (2014): 767-773
Ham, M. F. et al., Cancer Sci. 98 (2007): 1041-1047
Hanks, T. S. et al., Apoptosis. 17 (2012): 236-247
Haren, N. et al., Histol. Histopathol. 25 (2010): 1247-1255
Hatabe, S. et al., Mol. Clin Oncol 1 (2013): 845-850
Hayama, S. et al., Cancer Res 67 (2007): 4113-4122
Hegyi, K. et al., Pathobiology 79 (2012): 314-322
Hill, S. J. et al., Genes Dev. 28 (2014): 1957-1975
Hiramoto, T. et al., Oncogene 18 (1999): 3422-3426
Hu, J. et al., Pituitary. 10 (2007): 47-52
Hu, S. X. et al., Zhonghua Lao. Dong. Wei Sheng Zhi. Ye. Bing. Za Zhi. 31 (2013): 890-894
Huff, L. P. et al., Genes Cancer 4 (2013): 460-475
Ishikawa, N. et al., Cancer Sci. 97 (2006): 737-745
Ito, K. et al., Protein Cell 2 (2011): 755-763
Jager, D. et al., Cancer Res 60 (2000): 3584-3591
Januchowski, R. et al., Biomed. Res Int 2014 (2014): 365867
Jin, Y. et al., Int. J Clin Exp. Pathol. 7 (2014): 8724-8731
Jordheim, L. P. et al., Biomark. Med. 7 (2013): 663-671
Jordheim, L. P. et al., Lancet Oncol 12 (2011): 693-702
Ju, W. et al., Oncol. Res. 18 (2009): 47-56
Kanda, A. et al., Oncogene 24 (2005): 7266-7272
Kaplun, A. et al., Crit Rev Eukaryot. Gene Expr. 22 (2012): 249-258
Karlgren, M. et al., Expert. Opin. Ther. Targets. 11 (2007): 61-67
Kas, K. et al., J Biol Chem 273 (1998): 23026-23032
Kaur, S. et al., BMC. Cell Biol 9 (2008): 61
Kim, D. H., Yonsei Med. J 48 (2007): 694-700
Kim, D. S. et al., J Proteome. Res 9 (2010a): 3710-3719
Kim, J. E. et al., J Cancer Res Clin Oncol 136 (2010b): 47-53
Kounelakis, M. G. et al., IEEE J Biomed. Health Inform. 17 (2013): 128-135
Lages, E. et al., PLoS. One. 6 (2011): e20600
Lallet-Daher, H. et al., Oncogene 28 (2009): 1792-1806
Landrette, S. F. et al., Blood 105 (2005): 2900-2907
Langnaese, K. et al., Cytogenet. Cell Genet. 94 (2001): 233-240
Lee, Y. C. et al., Int. J Cancer 122 (2008b): 1630-1638
Li, B. et al., Cancer Res 61 (2001): 8014-8021
Li, G. H. et al., Bioinformatics. 30 (2014): 748-752
Li, J. F. et al., Zhonghua Wei Chang Wai Ke. Za Zhi. 15 (2012): 388-391
Li, Y. et al., PLoS. One. 8 (2013): e84489
Liu, B. et al., Int. J Clin Exp. Pathol. 7 (2014a): 3089-3100
Liu, L. et al., Retrovirology. 8 (2011a): 94
Liu, X. et al., Eur. J Cancer 50 (2014b): 2251-2262
Liu, Y. et al., Cancer Epidemiol. Biomarkers Prev. 18 (2009): 204-214
Liu, Y. et al., J Cancer 6 (2015b): 643-651
Lonardo, F. et al., Curr. Pharm. Des 16 (2010): 1877-1881
Lu, X. et al., Mol. Cancer Ther. 3 (2004): 861-872
Maass, N. et al., Acta Oncol 39 (2000): 931-934
Marchi, S. et al., Cell Death. Dis. 3 (2012): e304
Marioni, G. et al., Acta Otolaryngol. 129 (2009): 476-480
Marnef, A. et al., Int. J Biochem. Cell Biol 41 (2009): 977-981
Martin, L. et al., Oncogene 31 (2012): 4076-4084
Mason, J. M. et al., Nucleic Acids Res. 43 (2015): 3180-3196
Matsuda, R. et al., Br. J Cancer 104 (2011): 376-386
Medina, P. P. et al., Epigenetics. 3 (2008): 64-68
Mound, A. et al., Eur. J Cancer 49 (2013): 3738-3751
Naidu, S. R. et al., Oncogene 28 (2009): 2492-2501
Ng, Y. et al., J Biol Chem 279 (2004): 34156-34164
Nibbe, R. K. et al., Mol Cell Proteomics. 8 (2009): 827-845
Nishida, C. R. et al., Mol. Pharmacol. 78 (2010): 497-502
O'Geen, H. et al., PLoS. Genet. 3 (2007): e89
Ota, T. et al., Cancer Res 62 (2002): 5168-5177
Paliouras, M. et al., Tumour. Biol 29 (2008): 63-75
Papageorgio, C. et al., Int. J Oncol. 31 (2007): 1205-1211
Papageorgis, P. et al., Cancer Res 70 (2010): 968-978
Pohl, A. et al., Pharmacogenomics. J 11 (2011): 93-99
Pollari, S. et al., Mol. Cancer Res 10 (2012): 597-604
Qi, F. et al., Int. J Clin Exp. Pathol. 8 (2015): 1666-1673
RefSeq, The NCBI handbook [Internet], Chapter 18, (2002), www.ncbi.nlm.nih.gov/books/NBK21091/Reisman, D. N. et al., Cancer Res 63 (2003): 560-566
Robles, L. D. et al., J Biol Chem 277 (2002): 25431-25438
Ryu, B. et al., PLoS. One. 2 (2007): e594
Sager, R. et al., Curr. Top. Microbiol. Immunol. 213 (Pt 1) (1996): 51-64
Sakakura, C. et al., Anticancer Res 23 (2003): 3691-3697
Sakurai, Y. et al., Mol. Pharm. 11 (2014): 2713-2719
Sakurikar, N. et al., J Biol Chem 287 (2012): 39193-39204
Sheng, S., Front Biosci. 9 (2004): 2733-2745
Shibao, K. et al., Cell Calcium 48 (2010): 315-323
Shu, G. S. et al., Cancer Biomark. 11 (2012): 107-114
Stone, B. et al., Gene 267 (2001): 173-182
Strekalova, E. et al., Clin. Cancer Res. (2015)
Stutzer, I. et al., J Biol Chem 288 (2013): 10536-10547
Su, K. C. et al., Dev. Cell 21 (2011): 1104-1115
Sun, Y. et al., Oncotarget. 6 (2015b): 8244-8254
Takashima, S. et al., Tumour. Biol. 35 (2014): 4257-4265
Tatsuka, M. et al., Cancer Res 58 (1998): 4811-4816
Tsui, K. H. et al., Sci. Rep. 5 (2015): 12870
Van Ginkel, P. R. et al., Biochim. Biophys. Acta 1448 (1998): 290-297
Vanaja, D. K. et al., Clin Cancer Res 12 (2006): 1128-1136
Wang, G. et al., Oncogene 35 (2016): 651-661
Wang, G. et al., Tumour. Biol 36 (2015a): 1055-1065
Wang, Q. et al., PLoS. One. 8 (2013d): e70191
Wang, W. et al., Int. J Cancer 124 (2009b): 521-530
Wang, W. X. et al., Sichuan. Da. Xue. Xue. Bao. Yi. Xue. Ban. 40 (2009c): 857-860
Wierinckx, A. et al., Endocr. Relat Cancer 14 (2007): 887-900
Williams, K. A. et al., PLoS. Genet. 10 (2014): e1004809
Wu, M. X., Apoptosis. 8 (2003): 11-18
Wu, M. X. et al., Expert. Opin. Ther. Targets. 17 (2013): 593-606
Wu, S. et al., Cell Cycle 13 (2014a): 2869-2878
Wu, Z. et al., Neoplasia. 11 (2009): 66-76
Xu, F. et al., Biochem. J 416 (2008): 15-26
Yang, J. et al., Surg. Oncol 22 (2013): e53-e57
Yang, L. et al., Cancer Res 71 (2011a): 5558-5568
Yang, L. et al., Future. Oncol 8 (2012): 431-440
Yang, X. et al., Biomed. Pharmacother. 67 (2013): 681-684
Yang, Y. S. et al., Lung Cancer 74 (2011b): 12-24
Yousef, G. M. et al., Tumour. Biol 26 (2005): 227-235
Yu, B. et al., Exp. Cell Res 315 (2009): 3086-3098

Zhang, F. et al., J Viral Hepat. 21 (2014a): 241-250
Zhang, K. et al., Tumour. Biol 35 (2014e): 7669-7673
Zhang, M. et al., Zhong. Nan. Da. Xue. Xue. Bao. Yi. Xue. Ban. 36 (2011a): 274-276
Zhang, Y. et al., Cancer Sci. 101 (2010): 934-940
Zheng, G. et al., Biochem. Biophys. Res Commun. 364 (2007): 344-350
Follenzi A, et al. Nat Genet. 2000 June; 25(2):217-22.
Zufferey R, et al. J Virol. 1999 April; 73(4):2886-92.
Scholten K B, et al. Clin Immunol. 2006 May; 119(2):135-45.
Gustafsson C, et al. Trends Biotechnol. 2004 July; 22(7): 346-53. Review.
Kuball, J., et al. (2007). Blood 109, 2331-2338.
Schmitt, T. M., et al. (2009). Hum. Gene Ther. 20, 1240-1248

What is claimed:

1. A method of treating a HLA-A*02+ patient who has cancer, comprising administering to said patient a peptide consisting of the amino acid sequence of FLAELPGSLSL (SEQ ID NO: 6),
wherein said cancer is selected from the group consisting of colon or rectum cancer (CRC), lung cancer, glioma, stomach cancer, liver cancer, leukemia, breast cancer, skin cancer, ovarian cancer, bladder cancer, uterine cancer, gallbladder cancer, bile duct cancer, non-Hodgkin lymphoma, and esophageal cancer.

2. The method of claim 1, wherein the peptide is in the form of a composition comprising an adjuvant.

3. The method of claim 2, wherein the adjuvant is selected from anti-CD40 antibody, imiquimod, resiquimod, GM-CSF, cyclophosphamide, interferon-alpha, interferon-beta, CpG oligonucleotides and derivatives, poly-(I:C) and derivatives, RNA, sildenafil, particulate formulations with poly(lactide coglycolide) (PLG), virosomes, interleukin (IL)-1, IL-2, IL-4, IL-7, IL-12, IL-13, IL-15, IL-21, and IL-23.

4. The method of claim 1, wherein the cancer is colon or rectum cancer (CRC).

5. The method of claim 1, wherein the composition further comprises a carrier.

6. The method of claim 5, wherein the carrier is keyhole limpet haemocyanin or mannan.

7. The method of claim 2, wherein the adjuvant comprises IL-21.

8. The method of claim 1, wherein the cancer is lung cancer.

9. The method of claim 1, wherein the cancer is liver cancer.

10. The method of claim 1, wherein the cancer is prostate cancer.

11. The method of claim 1, wherein the cancer is breast cancer.

12. The method of claim 1, wherein the cancer is skin cancer.

13. The method of claim 2, wherein the adjuvant comprises IL-2, IL-7, or IL-15.

14. A composition comprising a peptide consisting of the amino acid sequence of FLAELPGSLSL (SEQ ID NO: 6) in the form of a pharmaceutically acceptable salt and an immunogenicity enhancing amount of at least one adjuvant.

15. The composition of claim 14, wherein the at least one adjuvant is selected from anti-CD40 antibody, imiquimod, resiquimod, GM-CSF, cyclophosphamide, interferon-alpha, interferon-beta, CpG oligonucleotides and derivatives, poly-(I:C) and derivatives, RNA, sildenafil, particulate formulations with poly(lactide coglycolide) (PLG), virosomes, interleukin (IL)-1, IL-2, IL-4, IL-7, IL-12, IL-13, IL-15, IL-21, and IL-23.

16. The composition of claim 14, wherein the at least one adjuvant comprises IL-21.

17. The composition of claim 14, wherein the pharmaceutically acceptable salt is chloride salt.

18. The composition of claim 14, wherein the at least one adjuvant comprises IL-2, IL-7, or IL-15.

* * * * *

SEQUENCE LISTING

```
<160> NUMBER OF SEQ ID NOS: 267

<210> SEQ ID NO 1
<211> LENGTH: 9
<212> TYPE: PRT
<213> ORGANISM: Homo sapiens

<400> SEQUENCE: 1

Ala Leu Ile Lys Gln Leu Phe Glu Ala
1               5

<210> SEQ ID NO 2
<211> LENGTH: 9
<212> TYPE: PRT
<213> ORGANISM: Homo sapiens

<400> SEQUENCE: 2

Ala Leu Leu Pro Arg Tyr Phe Phe Leu
1               5

<210> SEQ ID NO 3
<211> LENGTH: 10
<212> TYPE: PRT
<213> ORGANISM: Homo sapiens

<400> SEQUENCE: 3

Arg Leu Ile Pro Asp Thr Leu Tyr Ser Val
1               5                   10

<210> SEQ ID NO 4
<211> LENGTH: 11
<212> TYPE: PRT
<213> ORGANISM: Homo sapiens

<400> SEQUENCE: 4

Arg Leu Ala Glu Leu Thr Val Asp Glu Phe Leu
1               5                   10

<210> SEQ ID NO 5
<211> LENGTH: 10
<212> TYPE: PRT
<213> ORGANISM: Homo sapiens

<400> SEQUENCE: 5

Trp Leu Phe Asp Asp Gly Gly Leu Thr Leu
1               5                   10

<210> SEQ ID NO 6
<211> LENGTH: 11
<212> TYPE: PRT
<213> ORGANISM: Homo sapiens

<400> SEQUENCE: 6

Phe Leu Ala Glu Leu Pro Gly Ser Leu Ser Leu
1               5                   10
```

```
<210> SEQ ID NO 7
<211> LENGTH: 9
<212> TYPE: PRT
<213> ORGANISM: Homo sapiens

<400> SEQUENCE: 7

Tyr Leu Thr Arg His Leu Ala Val Leu
1               5

<210> SEQ ID NO 8
<211> LENGTH: 10
<212> TYPE: PRT
<213> ORGANISM: Homo sapiens

<400> SEQUENCE: 8

Ala Leu Met Leu Gln Gly Val Asp Leu Leu
1               5                   10

<210> SEQ ID NO 9
<211> LENGTH: 9
<212> TYPE: PRT
<213> ORGANISM: Homo sapiens

<400> SEQUENCE: 9

Ile Leu Asp Asp His Leu Ser Arg Val
1               5

<210> SEQ ID NO 10
<211> LENGTH: 9
<212> TYPE: PRT
<213> ORGANISM: Homo sapiens

<400> SEQUENCE: 10

Arg Met Tyr Asn Lys Ile Phe Ala Ile
1               5

<210> SEQ ID NO 11
<211> LENGTH: 9
<212> TYPE: PRT
<213> ORGANISM: Homo sapiens

<400> SEQUENCE: 11

Tyr Leu Phe Glu Lys Thr Phe Asn Met
1               5

<210> SEQ ID NO 12
<211> LENGTH: 10
<212> TYPE: PRT
<213> ORGANISM: Homo sapiens

<400> SEQUENCE: 12

Ala Leu Val Gln Gly Ile Leu Glu Arg Val
1               5                   10

<210> SEQ ID NO 13
<211> LENGTH: 9
<212> TYPE: PRT
<213> ORGANISM: Homo sapiens

<400> SEQUENCE: 13

Phe Leu Leu Ala Glu Asp Thr Lys Val
1               5
```

```
<210> SEQ ID NO 14
<211> LENGTH: 10
<212> TYPE: PRT
<213> ORGANISM: Homo sapiens

<400> SEQUENCE: 14

Phe Leu Asp Lys Pro Glu Asp Val Leu Leu
1               5                   10

<210> SEQ ID NO 15
<211> LENGTH: 9
<212> TYPE: PRT
<213> ORGANISM: Homo sapiens

<400> SEQUENCE: 15

Leu Gln Leu Asp Lys Glu Phe Gln Leu
1               5

<210> SEQ ID NO 16
<211> LENGTH: 9
<212> TYPE: PRT
<213> ORGANISM: Homo sapiens

<400> SEQUENCE: 16

Val Leu Val Asp Gln Ser Trp Val Leu
1               5

<210> SEQ ID NO 17
<211> LENGTH: 9
<212> TYPE: PRT
<213> ORGANISM: Homo sapiens

<400> SEQUENCE: 17

Ala Leu Ala Ala Ala Arg Val Glu Leu
1               5

<210> SEQ ID NO 18
<211> LENGTH: 10
<212> TYPE: PRT
<213> ORGANISM: Homo sapiens

<400> SEQUENCE: 18

Phe Leu Ser Ser Leu Lys Gly Gly Leu Leu
1               5                   10

<210> SEQ ID NO 19
<211> LENGTH: 10
<212> TYPE: PRT
<213> ORGANISM: Homo sapiens

<400> SEQUENCE: 19

Arg Leu Tyr Thr Lys Leu Leu Asn Glu Ala
1               5                   10

<210> SEQ ID NO 20
<211> LENGTH: 9
<212> TYPE: PRT
<213> ORGANISM: Homo sapiens

<400> SEQUENCE: 20

Tyr Leu Lys Asp Gly Asp Val Met Leu
1               5

<210> SEQ ID NO 21
<211> LENGTH: 9
```

```
<212> TYPE: PRT
<213> ORGANISM: Homo sapiens

<400> SEQUENCE: 21

Val Leu Ile Asp His Arg Trp Val Leu
1               5

<210> SEQ ID NO 22
<211> LENGTH: 9
<212> TYPE: PRT
<213> ORGANISM: Homo sapiens

<400> SEQUENCE: 22

Gly Leu Ile Asp Glu Val Met Val Leu
1               5

<210> SEQ ID NO 23
<211> LENGTH: 9
<212> TYPE: PRT
<213> ORGANISM: Homo sapiens

<400> SEQUENCE: 23

Phe Leu Asp Ala Asn Gly His Phe Val
1               5

<210> SEQ ID NO 24
<211> LENGTH: 9
<212> TYPE: PRT
<213> ORGANISM: Homo sapiens

<400> SEQUENCE: 24

Val Leu Asp Gly Val Leu Met Glu Leu
1               5

<210> SEQ ID NO 25
<211> LENGTH: 9
<212> TYPE: PRT
<213> ORGANISM: Homo sapiens

<400> SEQUENCE: 25

Ser Leu Ala Asp Arg Leu Ile Gly Val
1               5

<210> SEQ ID NO 26
<211> LENGTH: 13
<212> TYPE: PRT
<213> ORGANISM: Homo sapiens

<400> SEQUENCE: 26

Gly Leu Ala Ser Lys Glu Asn Phe Ser Asn Val Ser Leu
1               5                   10

<210> SEQ ID NO 27
<211> LENGTH: 10
<212> TYPE: PRT
<213> ORGANISM: Homo sapiens

<400> SEQUENCE: 27

Leu Leu Ala Asp Glu Asp Ser Ser Tyr Leu
1               5                   10

<210> SEQ ID NO 28
<211> LENGTH: 9
<212> TYPE: PRT
<213> ORGANISM: Homo sapiens
```

```
<400> SEQUENCE: 28

Ala Leu Thr Glu Ile Gln Glu Phe Ile
1               5

<210> SEQ ID NO 29
<211> LENGTH: 9
<212> TYPE: PRT
<213> ORGANISM: Homo sapiens

<400> SEQUENCE: 29

Gln Met Leu Asp Val Ala Ile Arg Val
1               5

<210> SEQ ID NO 30
<211> LENGTH: 9
<212> TYPE: PRT
<213> ORGANISM: Homo sapiens

<400> SEQUENCE: 30

Gly Leu Ser Ser Ala Tyr Gly Gly Leu
1               5

<210> SEQ ID NO 31
<211> LENGTH: 9
<212> TYPE: PRT
<213> ORGANISM: Homo sapiens

<400> SEQUENCE: 31

Leu Leu Tyr Gly Lys Tyr Val Ser Val
1               5

<210> SEQ ID NO 32
<211> LENGTH: 9
<212> TYPE: PRT
<213> ORGANISM: Homo sapiens

<400> SEQUENCE: 32

Lys Leu Asn Thr Glu Thr Phe Gly Val
1               5

<210> SEQ ID NO 33
<211> LENGTH: 9
<212> TYPE: PRT
<213> ORGANISM: Homo sapiens

<400> SEQUENCE: 33

Ala Leu Trp Glu Lys Asn Thr His Leu
1               5

<210> SEQ ID NO 34
<211> LENGTH: 9
<212> TYPE: PRT
<213> ORGANISM: Homo sapiens

<400> SEQUENCE: 34

Ile Leu Leu Glu Lys Ser Val Ser Val
1               5

<210> SEQ ID NO 35
<211> LENGTH: 9
<212> TYPE: PRT
<213> ORGANISM: Homo sapiens

<400> SEQUENCE: 35
```

Lys Leu Leu Asp Leu Thr Val Arg Ile
1               5

<210> SEQ ID NO 36
<211> LENGTH: 13
<212> TYPE: PRT
<213> ORGANISM: Homo sapiens

<400> SEQUENCE: 36

Gly Leu Leu Glu Ser Pro Ser Ile Phe Asn Phe Thr Ala
1               5                   10

<210> SEQ ID NO 37
<211> LENGTH: 11
<212> TYPE: PRT
<213> ORGANISM: Homo sapiens

<400> SEQUENCE: 37

Gly Leu Phe Ala Gly Leu Gly Gly Ala Gly Ala
1               5                   10

<210> SEQ ID NO 38
<211> LENGTH: 9
<212> TYPE: PRT
<213> ORGANISM: Homo sapiens

<400> SEQUENCE: 38

Ser Leu Ala Pro Thr Pro Val Ser Ala
1               5

<210> SEQ ID NO 39
<211> LENGTH: 10
<212> TYPE: PRT
<213> ORGANISM: Homo sapiens

<400> SEQUENCE: 39

Gly Leu Asn Gly Gly Ser Pro Ala Ala Ala
1               5                   10

<210> SEQ ID NO 40
<211> LENGTH: 9
<212> TYPE: PRT
<213> ORGANISM: Homo sapiens

<400> SEQUENCE: 40

Ala Leu Ser Asn Val Ile His Lys Val
1               5

<210> SEQ ID NO 41
<211> LENGTH: 9
<212> TYPE: PRT
<213> ORGANISM: Homo sapiens

<400> SEQUENCE: 41

Ile Leu Asp Asp Ser Phe Lys Leu Leu
1               5

<210> SEQ ID NO 42
<211> LENGTH: 9
<212> TYPE: PRT
<213> ORGANISM: Homo sapiens

<400> SEQUENCE: 42

Ser Ile Leu Asp Asp Ser Phe Lys Leu

```
<210> SEQ ID NO 43
<211> LENGTH: 9
<212> TYPE: PRT
<213> ORGANISM: Homo sapiens

<400> SEQUENCE: 43

Thr Leu Asp Ala Ala Gln Pro Arg Val
1               5

<210> SEQ ID NO 44
<211> LENGTH: 9
<212> TYPE: PRT
<213> ORGANISM: Homo sapiens

<400> SEQUENCE: 44

Ser Leu Glu Ser Lys Leu Thr Ser Val
1               5

<210> SEQ ID NO 45
<211> LENGTH: 9
<212> TYPE: PRT
<213> ORGANISM: Homo sapiens

<400> SEQUENCE: 45

Ala Leu Ala Glu Leu Leu His Gly Ala
1               5

<210> SEQ ID NO 46
<211> LENGTH: 9
<212> TYPE: PRT
<213> ORGANISM: Homo sapiens

<400> SEQUENCE: 46

Gly Leu Asp Asp Arg Tyr Ser Leu Val
1               5

<210> SEQ ID NO 47
<211> LENGTH: 9
<212> TYPE: PRT
<213> ORGANISM: Homo sapiens

<400> SEQUENCE: 47

Lys Leu Tyr Glu Arg Cys Glu Val Val
1               5

<210> SEQ ID NO 48
<211> LENGTH: 9
<212> TYPE: PRT
<213> ORGANISM: Homo sapiens

<400> SEQUENCE: 48

Phe Leu Asp Ala Ser Asp Pro Ala Leu
1               5

<210> SEQ ID NO 49
<211> LENGTH: 9
<212> TYPE: PRT
<213> ORGANISM: Homo sapiens

<400> SEQUENCE: 49

Ser Gly Met Gly Gly Ile Thr Ala Val
1               5
```

<210> SEQ ID NO 50
<211> LENGTH: 9
<212> TYPE: PRT
<213> ORGANISM: Homo sapiens

<400> SEQUENCE: 50

Thr Leu Met Ala Glu Met His Val Val
1               5

<210> SEQ ID NO 51
<211> LENGTH: 9
<212> TYPE: PRT
<213> ORGANISM: Homo sapiens

<400> SEQUENCE: 51

Gln Val Trp Glu Ile Gln His Thr Val
1               5

<210> SEQ ID NO 52
<211> LENGTH: 11
<212> TYPE: PRT
<213> ORGANISM: Homo sapiens

<400> SEQUENCE: 52

Ala Leu Asp Ser Ser Asn Ser Met Gln Thr Ile
1               5                   10

<210> SEQ ID NO 53
<211> LENGTH: 9
<212> TYPE: PRT
<213> ORGANISM: Homo sapiens

<400> SEQUENCE: 53

Phe Leu Leu Gly Ser Glu Ile Lys Leu
1               5

<210> SEQ ID NO 54
<211> LENGTH: 11
<212> TYPE: PRT
<213> ORGANISM: Homo sapiens

<400> SEQUENCE: 54

Ala Leu Leu Asn Gly Glu Tyr Leu Leu Ala Ala
1               5                   10

<210> SEQ ID NO 55
<211> LENGTH: 9
<212> TYPE: PRT
<213> ORGANISM: Homo sapiens

<400> SEQUENCE: 55

Gln Ile Ile Thr Ser Val Val Ser Val
1               5

<210> SEQ ID NO 56
<211> LENGTH: 12
<212> TYPE: PRT
<213> ORGANISM: Homo sapiens

<400> SEQUENCE: 56

Val Leu Phe Thr Asp Glu Gly Val Pro Lys Phe Leu
1               5                   10

<210> SEQ ID NO 57

```
<211> LENGTH: 9
<212> TYPE: PRT
<213> ORGANISM: Homo sapiens

<400> SEQUENCE: 57

Asn Leu Leu Glu Lys Glu Asn Tyr Leu
1               5

<210> SEQ ID NO 58
<211> LENGTH: 10
<212> TYPE: PRT
<213> ORGANISM: Homo sapiens

<400> SEQUENCE: 58

Ala Met Ala Asp Lys Met Asp Met Ser Leu
1               5                   10

<210> SEQ ID NO 59
<211> LENGTH: 9
<212> TYPE: PRT
<213> ORGANISM: Homo sapiens

<400> SEQUENCE: 59

Leu Leu Thr Asp Asn Val Val Lys Leu
1               5

<210> SEQ ID NO 60
<211> LENGTH: 10
<212> TYPE: PRT
<213> ORGANISM: Homo sapiens

<400> SEQUENCE: 60

Val Leu Asp Glu Asp Glu Pro Arg Phe Leu
1               5                   10

<210> SEQ ID NO 61
<211> LENGTH: 9
<212> TYPE: PRT
<213> ORGANISM: Homo sapiens

<400> SEQUENCE: 61

Lys Leu Leu Lys Leu Phe Gln Gly Val
1               5

<210> SEQ ID NO 62
<211> LENGTH: 9
<212> TYPE: PRT
<213> ORGANISM: Homo sapiens

<400> SEQUENCE: 62

Tyr Leu Ala Pro Glu Asn Gly Tyr Leu
1               5

<210> SEQ ID NO 63
<211> LENGTH: 9
<212> TYPE: PRT
<213> ORGANISM: Homo sapiens

<400> SEQUENCE: 63

Lys Leu Phe Ser Ile Leu Ser Thr Val
1               5

<210> SEQ ID NO 64
<211> LENGTH: 9
<212> TYPE: PRT
```

<213> ORGANISM: Homo sapiens

<400> SEQUENCE: 64

Lys Thr Leu Gly Lys Leu Trp Arg Leu
1               5

<210> SEQ ID NO 65
<211> LENGTH: 9
<212> TYPE: PRT
<213> ORGANISM: Homo sapiens

<400> SEQUENCE: 65

Phe Gly Ala Pro Gly Ile Ile Ser Ala
1               5

<210> SEQ ID NO 66
<211> LENGTH: 9
<212> TYPE: PRT
<213> ORGANISM: Homo sapiens

<400> SEQUENCE: 66

Gly Leu Asp Asp Gly Pro Asp Phe Leu
1               5

<210> SEQ ID NO 67
<211> LENGTH: 12
<212> TYPE: PRT
<213> ORGANISM: Homo sapiens

<400> SEQUENCE: 67

Ser Leu Asn Asp Leu Glu Lys Asp Val Met Leu Leu
1               5                   10

<210> SEQ ID NO 68
<211> LENGTH: 9
<212> TYPE: PRT
<213> ORGANISM: Homo sapiens

<400> SEQUENCE: 68

Ser Ile Leu Gln Phe Val His Met Val
1               5

<210> SEQ ID NO 69
<211> LENGTH: 13
<212> TYPE: PRT
<213> ORGANISM: Homo sapiens

<400> SEQUENCE: 69

Gly Met Leu Asn Glu Ala Glu Gly Lys Ala Ile Lys Leu
1               5                   10

<210> SEQ ID NO 70
<211> LENGTH: 9
<212> TYPE: PRT
<213> ORGANISM: Homo sapiens

<400> SEQUENCE: 70

Met Ile Ser Glu Leu Glu Val Arg Leu
1               5

<210> SEQ ID NO 71
<211> LENGTH: 10
<212> TYPE: PRT
<213> ORGANISM: Homo sapiens

```
<400> SEQUENCE: 71

Arg Leu Trp Thr Glu Ile Pro Thr Ala Ile
1               5                   10

<210> SEQ ID NO 72
<211> LENGTH: 10
<212> TYPE: PRT
<213> ORGANISM: Homo sapiens

<400> SEQUENCE: 72

Tyr Leu Leu Asp Tyr Pro Asn Asn Leu Leu
1               5                   10

<210> SEQ ID NO 73
<211> LENGTH: 9
<212> TYPE: PRT
<213> ORGANISM: Homo sapiens

<400> SEQUENCE: 73

Tyr Leu Phe Asp Ile Ala Val Ser Met
1               5

<210> SEQ ID NO 74
<211> LENGTH: 9
<212> TYPE: PRT
<213> ORGANISM: Homo sapiens

<400> SEQUENCE: 74

Tyr Leu Met Gly Phe Leu His Ala Val
1               5

<210> SEQ ID NO 75
<211> LENGTH: 9
<212> TYPE: PRT
<213> ORGANISM: Homo sapiens

<400> SEQUENCE: 75

Glu Met Ile Glu Asn Ile Gln Ser Val
1               5

<210> SEQ ID NO 76
<211> LENGTH: 10
<212> TYPE: PRT
<213> ORGANISM: Homo sapiens

<400> SEQUENCE: 76

Tyr Leu Ile Gly Glu Lys Gln His Tyr Leu
1               5                   10

<210> SEQ ID NO 77
<211> LENGTH: 9
<212> TYPE: PRT
<213> ORGANISM: Homo sapiens

<400> SEQUENCE: 77

Ser Leu Leu Lys Arg Asp Phe Gly Ala
1               5

<210> SEQ ID NO 78
<211> LENGTH: 9
<212> TYPE: PRT
<213> ORGANISM: Homo sapiens

<400> SEQUENCE: 78
```

```
Ala Leu Asp Pro Glu Leu Leu Leu Leu
1               5

<210> SEQ ID NO 79
<211> LENGTH: 10
<212> TYPE: PRT
<213> ORGANISM: Homo sapiens

<400> SEQUENCE: 79

Ser Leu Ala Ala Asp Gln Leu Leu Lys Leu
1               5                   10

<210> SEQ ID NO 80
<211> LENGTH: 11
<212> TYPE: PRT
<213> ORGANISM: Homo sapiens

<400> SEQUENCE: 80

Gln Val Asp Glu Val Val Asp Ile Met Arg Val
1               5                   10

<210> SEQ ID NO 81
<211> LENGTH: 9
<212> TYPE: PRT
<213> ORGANISM: Homo sapiens

<400> SEQUENCE: 81

Ala Leu Leu Ser Gln Gln Thr His Leu
1               5

<210> SEQ ID NO 82
<211> LENGTH: 10
<212> TYPE: PRT
<213> ORGANISM: Homo sapiens

<400> SEQUENCE: 82

Gln Leu Tyr Glu Glu Pro Asp Thr Lys Leu
1               5                   10

<210> SEQ ID NO 83
<211> LENGTH: 10
<212> TYPE: PRT
<213> ORGANISM: Homo sapiens

<400> SEQUENCE: 83

Leu Thr Ile Glu Asp Gly Ile Phe Glu Val
1               5                   10

<210> SEQ ID NO 84
<211> LENGTH: 11
<212> TYPE: PRT
<213> ORGANISM: Homo sapiens

<400> SEQUENCE: 84

Ser Met Val Glu Asp Ile Thr Gly Leu Arg Leu
1               5                   10

<210> SEQ ID NO 85
<211> LENGTH: 11
<212> TYPE: PRT
<213> ORGANISM: Homo sapiens

<400> SEQUENCE: 85

Ile Leu His Asp Ile Asn Ser Asp Gly Val Leu
1               5                   10
```

```
<210> SEQ ID NO 86
<211> LENGTH: 9
<212> TYPE: PRT
<213> ORGANISM: Homo sapiens

<400> SEQUENCE: 86

Lys Val Phe Pro Gly Lys Ile Ser Val
1               5

<210> SEQ ID NO 87
<211> LENGTH: 10
<212> TYPE: PRT
<213> ORGANISM: Homo sapiens

<400> SEQUENCE: 87

Leu Leu Phe Asp Ala Pro Asp Leu Arg Leu
1               5                   10

<210> SEQ ID NO 88
<211> LENGTH: 9
<212> TYPE: PRT
<213> ORGANISM: Homo sapiens

<400> SEQUENCE: 88

Lys Leu Asp Ile Lys Val Glu Thr Val
1               5

<210> SEQ ID NO 89
<211> LENGTH: 9
<212> TYPE: PRT
<213> ORGANISM: Homo sapiens

<400> SEQUENCE: 89

Ser Leu Ile Glu Tyr Glu Phe Arg Val
1               5

<210> SEQ ID NO 90
<211> LENGTH: 11
<212> TYPE: PRT
<213> ORGANISM: Homo sapiens

<400> SEQUENCE: 90

Gly Leu Leu Lys Pro Gly Leu Asn Val Val Leu
1               5                   10

<210> SEQ ID NO 91
<211> LENGTH: 9
<212> TYPE: PRT
<213> ORGANISM: Homo sapiens

<400> SEQUENCE: 91

Thr Val Asp Val Ala Thr Pro Ser Val
1               5

<210> SEQ ID NO 92
<211> LENGTH: 9
<212> TYPE: PRT
<213> ORGANISM: Homo sapiens

<400> SEQUENCE: 92

Trp Ile Asp Asp Thr Ser Ala Phe Val
1               5
```

-continued

<210> SEQ ID NO 93
<211> LENGTH: 9
<212> TYPE: PRT
<213> ORGANISM: Homo sapiens

<400> SEQUENCE: 93

Ser Leu Gln Glu Leu Arg Leu Leu Leu
1               5

<210> SEQ ID NO 94
<211> LENGTH: 9
<212> TYPE: PRT
<213> ORGANISM: Homo sapiens

<400> SEQUENCE: 94

Lys Ser Met Asp Ile Val Leu Thr Val
1               5

<210> SEQ ID NO 95
<211> LENGTH: 9
<212> TYPE: PRT
<213> ORGANISM: Homo sapiens

<400> SEQUENCE: 95

Ala Ile Leu Asp Ala His Ile Glu Val
1               5

<210> SEQ ID NO 96
<211> LENGTH: 9
<212> TYPE: PRT
<213> ORGANISM: Homo sapiens

<400> SEQUENCE: 96

Lys Leu Tyr Ser Arg Leu Val Tyr Val
1               5

<210> SEQ ID NO 97
<211> LENGTH: 9
<212> TYPE: PRT
<213> ORGANISM: Homo sapiens

<400> SEQUENCE: 97

Ala Leu Trp Trp Gly Val Val Thr Val
1               5

<210> SEQ ID NO 98
<211> LENGTH: 9
<212> TYPE: PRT
<213> ORGANISM: Homo sapiens

<400> SEQUENCE: 98

Ala Met Asn Gly Lys Ser Phe Ser Val
1               5

<210> SEQ ID NO 99
<211> LENGTH: 10
<212> TYPE: PRT
<213> ORGANISM: Homo sapiens

<400> SEQUENCE: 99

Lys Leu Leu Glu Val Asp Leu Asp Thr Val
1               5                   10

<210> SEQ ID NO 100
<211> LENGTH: 9

```
<212> TYPE: PRT
<213> ORGANISM: Homo sapiens

<400> SEQUENCE: 100

Ser Leu Asp Asp Phe Leu Ala Thr Ala
1               5

<210> SEQ ID NO 101
<211> LENGTH: 10
<212> TYPE: PRT
<213> ORGANISM: Homo sapiens

<400> SEQUENCE: 101

Gly Leu Ser Glu Gly His Thr Phe Gln Val
1               5                   10

<210> SEQ ID NO 102
<211> LENGTH: 9
<212> TYPE: PRT
<213> ORGANISM: Homo sapiens

<400> SEQUENCE: 102

Lys Ile Leu Val Ser Leu Ile Glu Val
1               5

<210> SEQ ID NO 103
<211> LENGTH: 9
<212> TYPE: PRT
<213> ORGANISM: Homo sapiens

<400> SEQUENCE: 103

Phe Leu Phe Gly Tyr Pro Lys Arg Leu
1               5

<210> SEQ ID NO 104
<211> LENGTH: 12
<212> TYPE: PRT
<213> ORGANISM: Homo sapiens

<400> SEQUENCE: 104

Ile Leu Leu Thr Ile Lys Asp Asp Thr Ile Tyr Leu
1               5                   10

<210> SEQ ID NO 105
<211> LENGTH: 9
<212> TYPE: PRT
<213> ORGANISM: Homo sapiens

<400> SEQUENCE: 105

Tyr Ala Leu Asp Leu Ser Thr Phe Leu
1               5

<210> SEQ ID NO 106
<211> LENGTH: 9
<212> TYPE: PRT
<213> ORGANISM: Homo sapiens

<400> SEQUENCE: 106

Ser Leu Ile Ser Glu Lys Ile Leu Leu
1               5

<210> SEQ ID NO 107
<211> LENGTH: 10
<212> TYPE: PRT
<213> ORGANISM: Homo sapiens
```

<400> SEQUENCE: 107

Ala Leu Leu Gly Gly Gly Pro Tyr Met Leu
1               5                   10

<210> SEQ ID NO 108
<211> LENGTH: 12
<212> TYPE: PRT
<213> ORGANISM: Homo sapiens

<400> SEQUENCE: 108

Ser Leu Ala Glu Leu Val Pro Gly Val Gly Gly Ile
1               5                   10

<210> SEQ ID NO 109
<211> LENGTH: 9
<212> TYPE: PRT
<213> ORGANISM: Homo sapiens

<400> SEQUENCE: 109

Ala Leu Asp Gly Asp Gln Met Glu Leu
1               5

<210> SEQ ID NO 110
<211> LENGTH: 11
<212> TYPE: PRT
<213> ORGANISM: Homo sapiens

<400> SEQUENCE: 110

Leu Leu Gly Glu Leu Pro Arg Leu Leu Leu
1               5                   10

<210> SEQ ID NO 111
<211> LENGTH: 9
<212> TYPE: PRT
<213> ORGANISM: Homo sapiens

<400> SEQUENCE: 111

His Met Asp Asp Gly Gly Tyr Ser Met
1               5

<210> SEQ ID NO 112
<211> LENGTH: 9
<212> TYPE: PRT
<213> ORGANISM: Homo sapiens

<400> SEQUENCE: 112

Lys Leu Gly Gln Val Leu Ile Tyr Leu
1               5

<210> SEQ ID NO 113
<211> LENGTH: 9
<212> TYPE: PRT
<213> ORGANISM: Homo sapiens

<400> SEQUENCE: 113

Ile Leu Tyr Asp Leu Gln Gln Asn Leu
1               5

<210> SEQ ID NO 114
<211> LENGTH: 9
<212> TYPE: PRT
<213> ORGANISM: Homo sapiens

<400> SEQUENCE: 114

Thr Ala Val Gly His Ala Leu Val Leu
1               5

<210> SEQ ID NO 115
<211> LENGTH: 9
<212> TYPE: PRT
<213> ORGANISM: Homo sapiens

<400> SEQUENCE: 115

Ser Leu Phe Asp Val Ser His Met Leu
1               5

<210> SEQ ID NO 116
<211> LENGTH: 9
<212> TYPE: PRT
<213> ORGANISM: Homo sapiens

<400> SEQUENCE: 116

Leu Val Tyr Gln Phe Val His Pro Ile
1               5

<210> SEQ ID NO 117
<211> LENGTH: 12
<212> TYPE: PRT
<213> ORGANISM: Homo sapiens

<400> SEQUENCE: 117

Thr Leu Gln Pro Val Asp Asn Ser Thr Ile Ser Leu
1               5                   10

<210> SEQ ID NO 118
<211> LENGTH: 9
<212> TYPE: PRT
<213> ORGANISM: Homo sapiens

<400> SEQUENCE: 118

Leu Leu Ala Asp Leu Lys Thr Met Val
1               5

<210> SEQ ID NO 119
<211> LENGTH: 9
<212> TYPE: PRT
<213> ORGANISM: Homo sapiens

<400> SEQUENCE: 119

Ile Leu Tyr Gln Thr Val Thr Gly Leu
1               5

<210> SEQ ID NO 120
<211> LENGTH: 9
<212> TYPE: PRT
<213> ORGANISM: Homo sapiens

<400> SEQUENCE: 120

Val Leu Tyr Glu Gly Val Asp Glu Val
1               5

<210> SEQ ID NO 121
<211> LENGTH: 10
<212> TYPE: PRT
<213> ORGANISM: Homo sapiens

<400> SEQUENCE: 121

Ser Leu Ala Pro Asn Ile Ile Ser Gln Leu

```
1               5                  10

<210> SEQ ID NO 122
<211> LENGTH: 9
<212> TYPE: PRT
<213> ORGANISM: Homo sapiens

<400> SEQUENCE: 122

Ser Leu Met Gly Met Val Leu Lys Leu
1               5

<210> SEQ ID NO 123
<211> LENGTH: 9
<212> TYPE: PRT
<213> ORGANISM: Homo sapiens

<400> SEQUENCE: 123

Lys Thr Leu Glu Arg Ser Tyr Leu Leu
1               5

<210> SEQ ID NO 124
<211> LENGTH: 11
<212> TYPE: PRT
<213> ORGANISM: Homo sapiens

<400> SEQUENCE: 124

Arg Val Leu Pro Pro Ser Ala Leu Gln Ser Val
1               5                  10

<210> SEQ ID NO 125
<211> LENGTH: 11
<212> TYPE: PRT
<213> ORGANISM: Homo sapiens

<400> SEQUENCE: 125

Lys Leu Gly Asp Phe Gly Leu Leu Val Glu Leu
1               5                  10

<210> SEQ ID NO 126
<211> LENGTH: 9
<212> TYPE: PRT
<213> ORGANISM: Homo sapiens

<400> SEQUENCE: 126

Thr Leu Ala Lys Tyr Leu Met Glu Leu
1               5

<210> SEQ ID NO 127
<211> LENGTH: 12
<212> TYPE: PRT
<213> ORGANISM: Homo sapiens

<400> SEQUENCE: 127

Arg Leu Ala Glu Leu Thr Val Asp Glu Phe Leu Ala
1               5                  10

<210> SEQ ID NO 128
<211> LENGTH: 9
<212> TYPE: PRT
<213> ORGANISM: Homo sapiens

<400> SEQUENCE: 128

Met Leu Asp Asp Arg Ala Tyr Leu Val
1               5
```

```
<210> SEQ ID NO 129
<211> LENGTH: 9
<212> TYPE: PRT
<213> ORGANISM: Homo sapiens

<400> SEQUENCE: 129

Val Leu Ile Asp Val Leu Lys Glu Leu
1               5

<210> SEQ ID NO 130
<211> LENGTH: 12
<212> TYPE: PRT
<213> ORGANISM: Homo sapiens

<400> SEQUENCE: 130

Gly Leu Gly Gly Ser Gln Leu Ile Asp Thr His Leu
1               5                   10

<210> SEQ ID NO 131
<211> LENGTH: 9
<212> TYPE: PRT
<213> ORGANISM: Homo sapiens

<400> SEQUENCE: 131

Lys Leu Leu Asp Val Val His Pro Ala
1               5

<210> SEQ ID NO 132
<211> LENGTH: 10
<212> TYPE: PRT
<213> ORGANISM: Homo sapiens

<400> SEQUENCE: 132

Ala Leu Leu Asn Ala Ile Leu His Ser Ala
1               5                   10

<210> SEQ ID NO 133
<211> LENGTH: 9
<212> TYPE: PRT
<213> ORGANISM: Homo sapiens

<400> SEQUENCE: 133

Arg Thr Phe Glu Lys Ile Glu Glu Val
1               5

<210> SEQ ID NO 134
<211> LENGTH: 11
<212> TYPE: PRT
<213> ORGANISM: Homo sapiens

<400> SEQUENCE: 134

Gly Val Ala Gly Gly Ser Ile Leu Lys Gly Val
1               5                   10

<210> SEQ ID NO 135
<211> LENGTH: 9
<212> TYPE: PRT
<213> ORGANISM: Homo sapiens

<400> SEQUENCE: 135

Lys Leu Gln Glu Glu Ile Pro Val Leu
1               5

<210> SEQ ID NO 136
```

```
<211> LENGTH: 10
<212> TYPE: PRT
<213> ORGANISM: Homo sapiens

<400> SEQUENCE: 136

Lys Leu Phe Asp Ile Phe Ser Gln Gln Val
1               5                   10

<210> SEQ ID NO 137
<211> LENGTH: 9
<212> TYPE: PRT
<213> ORGANISM: Homo sapiens

<400> SEQUENCE: 137

Gln Leu Thr Glu Ile Lys Pro Leu Leu
1               5

<210> SEQ ID NO 138
<211> LENGTH: 9
<212> TYPE: PRT
<213> ORGANISM: Homo sapiens

<400> SEQUENCE: 138

Lys Gln Phe Glu Gly Thr Val Glu Ile
1               5

<210> SEQ ID NO 139
<211> LENGTH: 10
<212> TYPE: PRT
<213> ORGANISM: Homo sapiens

<400> SEQUENCE: 139

Val Leu Leu Asn Glu Ile Leu Glu Gln Val
1               5                   10

<210> SEQ ID NO 140
<211> LENGTH: 9
<212> TYPE: PRT
<213> ORGANISM: Homo sapiens

<400> SEQUENCE: 140

Leu Leu Asn Glu Ile Leu Glu Gln Val
1               5

<210> SEQ ID NO 141
<211> LENGTH: 9
<212> TYPE: PRT
<213> ORGANISM: Homo sapiens

<400> SEQUENCE: 141

Ala Val Ile Glu His Leu Glu Arg Leu
1               5

<210> SEQ ID NO 142
<211> LENGTH: 9
<212> TYPE: PRT
<213> ORGANISM: Homo sapiens

<400> SEQUENCE: 142

Ser Leu Val Gln Arg Val Glu Thr Ile
1               5

<210> SEQ ID NO 143
<211> LENGTH: 9
<212> TYPE: PRT
```

<213> ORGANISM: Homo sapiens

<400> SEQUENCE: 143

Lys Leu Ser Asp Val Trp Lys Glu Leu
1               5

<210> SEQ ID NO 144
<211> LENGTH: 9
<212> TYPE: PRT
<213> ORGANISM: Homo sapiens

<400> SEQUENCE: 144

Leu Leu Asn Asp Arg Ile Trp Leu Ala
1               5

<210> SEQ ID NO 145
<211> LENGTH: 9
<212> TYPE: PRT
<213> ORGANISM: Homo sapiens

<400> SEQUENCE: 145

Leu Leu Leu Glu Val Val Lys Gln Val
1               5

<210> SEQ ID NO 146
<211> LENGTH: 9
<212> TYPE: PRT
<213> ORGANISM: Homo sapiens

<400> SEQUENCE: 146

Ala Leu Ser Asp Glu Thr Trp Gly Leu
1               5

<210> SEQ ID NO 147
<211> LENGTH: 9
<212> TYPE: PRT
<213> ORGANISM: Homo sapiens

<400> SEQUENCE: 147

Thr Leu Thr Glu Leu Arg Ala Phe Leu
1               5

<210> SEQ ID NO 148
<211> LENGTH: 10
<212> TYPE: PRT
<213> ORGANISM: Homo sapiens

<400> SEQUENCE: 148

Arg Leu Leu Glu Asn Met Thr Glu Val Val
1               5                   10

<210> SEQ ID NO 149
<211> LENGTH: 11
<212> TYPE: PRT
<213> ORGANISM: Homo sapiens

<400> SEQUENCE: 149

Tyr Gln Phe Asp Lys Val Gly Ile Leu Thr Leu
1               5                   10

<210> SEQ ID NO 150
<211> LENGTH: 10
<212> TYPE: PRT
<213> ORGANISM: Homo sapiens

```
<400> SEQUENCE: 150

Arg Leu Ala Asp Leu Glu Ala Leu Lys Val
1               5                   10

<210> SEQ ID NO 151
<211> LENGTH: 14
<212> TYPE: PRT
<213> ORGANISM: Homo sapiens

<400> SEQUENCE: 151

Ser Ala Gln Gly Ser Asp Val Ser Leu Thr Ala Cys Lys Val
1               5                   10

<210> SEQ ID NO 152
<211> LENGTH: 9
<212> TYPE: PRT
<213> ORGANISM: Homo sapiens

<400> SEQUENCE: 152

Lys Leu Leu Ala Val Ile His Glu Leu
1               5

<210> SEQ ID NO 153
<211> LENGTH: 12
<212> TYPE: PRT
<213> ORGANISM: Homo sapiens

<400> SEQUENCE: 153

Ile Leu Phe Ser Glu Asp Ser Thr Lys Leu Phe Val
1               5                   10

<210> SEQ ID NO 154
<211> LENGTH: 11
<212> TYPE: PRT
<213> ORGANISM: Homo sapiens

<400> SEQUENCE: 154

Lys Leu Pro Ser Glu Thr Ile Phe Val Gly Cys
1               5                   10

<210> SEQ ID NO 155
<211> LENGTH: 10
<212> TYPE: PRT
<213> ORGANISM: Homo sapiens

<400> SEQUENCE: 155

Arg Leu Leu Gly Glu Glu Val Val Arg Val
1               5                   10

<210> SEQ ID NO 156
<211> LENGTH: 9
<212> TYPE: PRT
<213> ORGANISM: Homo sapiens

<400> SEQUENCE: 156

Ser Leu Met Met Thr Ile Ile Asn Leu
1               5

<210> SEQ ID NO 157
<211> LENGTH: 9
<212> TYPE: PRT
<213> ORGANISM: Homo sapiens

<400> SEQUENCE: 157
```

```
Ser Leu Ile Glu Arg Asp Leu Lys Leu
1               5

<210> SEQ ID NO 158
<211> LENGTH: 10
<212> TYPE: PRT
<213> ORGANISM: Homo sapiens

<400> SEQUENCE: 158

Gly Leu Leu Asp Pro Ser Val Phe His Val
1               5                   10

<210> SEQ ID NO 159
<211> LENGTH: 11
<212> TYPE: PRT
<213> ORGANISM: Homo sapiens

<400> SEQUENCE: 159

Val Leu Val Asp Asp Gly Ile Lys Val Val
1               5                   10

<210> SEQ ID NO 160
<211> LENGTH: 10
<212> TYPE: PRT
<213> ORGANISM: Homo sapiens

<400> SEQUENCE: 160

Lys Leu Leu Glu Phe Asp Gln Leu Gln Leu
1               5                   10

<210> SEQ ID NO 161
<211> LENGTH: 9
<212> TYPE: PRT
<213> ORGANISM: Homo sapiens

<400> SEQUENCE: 161

Phe Leu Lys Asn Glu Leu Asp Asn Val
1               5

<210> SEQ ID NO 162
<211> LENGTH: 9
<212> TYPE: PRT
<213> ORGANISM: Homo sapiens

<400> SEQUENCE: 162

Lys Leu Met Asp Tyr Ile Asp Glu Leu
1               5

<210> SEQ ID NO 163
<211> LENGTH: 9
<212> TYPE: PRT
<213> ORGANISM: Homo sapiens

<400> SEQUENCE: 163

Arg Leu Leu His Glu Val Gln Glu Leu
1               5

<210> SEQ ID NO 164
<211> LENGTH: 10
<212> TYPE: PRT
<213> ORGANISM: Homo sapiens

<400> SEQUENCE: 164

Lys Met Leu Asp Glu Ile Leu Leu Gln Leu
1               5                   10
```

<210> SEQ ID NO 165
<211> LENGTH: 11
<212> TYPE: PRT
<213> ORGANISM: Homo sapiens

<400> SEQUENCE: 165

Arg Leu Leu Asp Phe Pro Glu Ala Met Val Leu
1               5                   10

<210> SEQ ID NO 166
<211> LENGTH: 11
<212> TYPE: PRT
<213> ORGANISM: Homo sapiens

<400> SEQUENCE: 166

Gly Leu Leu Glu Ala Arg Gly Ile Leu Gly Leu
1               5                   10

<210> SEQ ID NO 167
<211> LENGTH: 11
<212> TYPE: PRT
<213> ORGANISM: Homo sapiens

<400> SEQUENCE: 167

Ser Val Ile Asp His Ile His Leu Ile Ser Val
1               5                   10

<210> SEQ ID NO 168
<211> LENGTH: 10
<212> TYPE: PRT
<213> ORGANISM: Homo sapiens

<400> SEQUENCE: 168

Gly Leu Ile Arg Phe Pro Leu Met Thr Ile
1               5                   10

<210> SEQ ID NO 169
<211> LENGTH: 9
<212> TYPE: PRT
<213> ORGANISM: Homo sapiens

<400> SEQUENCE: 169

Tyr Leu Ala His Phe Ile Glu Gly Leu
1               5

<210> SEQ ID NO 170
<211> LENGTH: 9
<212> TYPE: PRT
<213> ORGANISM: Homo sapiens

<400> SEQUENCE: 170

Ala Leu Ala Gly Gly Ile Thr Met Val
1               5

<210> SEQ ID NO 171
<211> LENGTH: 11
<212> TYPE: PRT
<213> ORGANISM: Homo sapiens

<400> SEQUENCE: 171

Arg Leu Gln Glu Thr Glu Gly Met Val Ala Val
1               5                   10

```
<210> SEQ ID NO 172
<211> LENGTH: 10
<212> TYPE: PRT
<213> ORGANISM: Homo sapiens

<400> SEQUENCE: 172

Leu Leu Leu Asp Thr Val Thr Met Gln Val
1               5                   10

<210> SEQ ID NO 173
<211> LENGTH: 9
<212> TYPE: PRT
<213> ORGANISM: Homo sapiens

<400> SEQUENCE: 173

Lys Leu Gly Asp Leu Met Val Leu Leu
1               5

<210> SEQ ID NO 174
<211> LENGTH: 11
<212> TYPE: PRT
<213> ORGANISM: Homo sapiens

<400> SEQUENCE: 174

Ile Leu Leu Asp Asp Asn Met Gln Ile Arg Leu
1               5                   10

<210> SEQ ID NO 175
<211> LENGTH: 13
<212> TYPE: PRT
<213> ORGANISM: Homo sapiens

<400> SEQUENCE: 175

Thr Leu Leu Gly Gly Lys Glu Ala Gln Ala Leu Gly Val
1               5                   10

<210> SEQ ID NO 176
<211> LENGTH: 9
<212> TYPE: PRT
<213> ORGANISM: Homo sapiens

<400> SEQUENCE: 176

Arg Thr Leu Asp Lys Val Leu Glu Val
1               5

<210> SEQ ID NO 177
<211> LENGTH: 10
<212> TYPE: PRT
<213> ORGANISM: Homo sapiens

<400> SEQUENCE: 177

Ala Leu Leu Gln Gly Ala Ile Glu Ser Val
1               5                   10

<210> SEQ ID NO 178
<211> LENGTH: 9
<212> TYPE: PRT
<213> ORGANISM: Homo sapiens

<400> SEQUENCE: 178

Tyr Leu Phe Arg Glu Pro Ala Thr Ile
1               5

<210> SEQ ID NO 179
<211> LENGTH: 9
```

```
<212> TYPE: PRT
<213> ORGANISM: Homo sapiens

<400> SEQUENCE: 179

Arg Leu Leu Ser Pro Leu Ser Ser Ala
1               5

<210> SEQ ID NO 180
<211> LENGTH: 9
<212> TYPE: PRT
<213> ORGANISM: Homo sapiens

<400> SEQUENCE: 180

Asn Leu Leu Glu Ile Ala Pro His Leu
1               5

<210> SEQ ID NO 181
<211> LENGTH: 12
<212> TYPE: PRT
<213> ORGANISM: Homo sapiens

<400> SEQUENCE: 181

Asn Leu Phe Asp Leu Gly Gly Gln Tyr Leu Arg Val
1               5                   10

<210> SEQ ID NO 182
<211> LENGTH: 9
<212> TYPE: PRT
<213> ORGANISM: Homo sapiens

<400> SEQUENCE: 182

Ser Leu Asn Lys Trp Ile Phe Thr Val
1               5

<210> SEQ ID NO 183
<211> LENGTH: 9
<212> TYPE: PRT
<213> ORGANISM: Homo sapiens

<400> SEQUENCE: 183

Thr Leu Gln Glu Val Val Thr Gly Val
1               5

<210> SEQ ID NO 184
<211> LENGTH: 12
<212> TYPE: PRT
<213> ORGANISM: Homo sapiens

<400> SEQUENCE: 184

Ser Leu Leu Asp Glu Asn Asn Val Ser Ser Tyr Leu
1               5                   10

<210> SEQ ID NO 185
<211> LENGTH: 9
<212> TYPE: PRT
<213> ORGANISM: Homo sapiens

<400> SEQUENCE: 185

Val Leu Tyr Thr Gly Val Val Arg Val
1               5

<210> SEQ ID NO 186
<211> LENGTH: 9
<212> TYPE: PRT
<213> ORGANISM: Homo sapiens
```

<400> SEQUENCE: 186

Lys Met Ser Glu Lys Ile Leu Leu Leu
1               5

<210> SEQ ID NO 187
<211> LENGTH: 9
<212> TYPE: PRT
<213> ORGANISM: Homo sapiens

<400> SEQUENCE: 187

Gly Leu His Asn Val Val Tyr Gly Ile
1               5

<210> SEQ ID NO 188
<211> LENGTH: 10
<212> TYPE: PRT
<213> ORGANISM: Homo sapiens

<400> SEQUENCE: 188

Phe Leu Val Asp Gly Pro Arg Val Gln Leu
1               5                   10

<210> SEQ ID NO 189
<211> LENGTH: 11
<212> TYPE: PRT
<213> ORGANISM: Homo sapiens

<400> SEQUENCE: 189

Ala Ile Ser Glu Val Ile Gly Lys Ile Thr Ala
1               5                   10

<210> SEQ ID NO 190
<211> LENGTH: 9
<212> TYPE: PRT
<213> ORGANISM: Homo sapiens

<400> SEQUENCE: 190

Ala Met Ala Glu Met Val Leu Gln Val
1               5

<210> SEQ ID NO 191
<211> LENGTH: 9
<212> TYPE: PRT
<213> ORGANISM: Homo sapiens

<400> SEQUENCE: 191

Gln Leu Phe Ser Glu Ile His Asn Leu
1               5

<210> SEQ ID NO 192
<211> LENGTH: 9
<212> TYPE: PRT
<213> ORGANISM: Homo sapiens

<400> SEQUENCE: 192

Lys Ile Gln Glu Met Gln His Phe Leu
1               5

<210> SEQ ID NO 193
<211> LENGTH: 9
<212> TYPE: PRT
<213> ORGANISM: Homo sapiens

<400> SEQUENCE: 193

```
Lys Leu Ser Pro Thr Val Val Gly Leu
1               5

<210> SEQ ID NO 194
<211> LENGTH: 9
<212> TYPE: PRT
<213> ORGANISM: Homo sapiens

<400> SEQUENCE: 194

Ser Leu Tyr Lys Gly Leu Leu Ser Val
1               5

<210> SEQ ID NO 195
<211> LENGTH: 9
<212> TYPE: PRT
<213> ORGANISM: Homo sapiens

<400> SEQUENCE: 195

Leu Leu Leu Gly Glu Arg Val Ala Leu
1               5

<210> SEQ ID NO 196
<211> LENGTH: 9
<212> TYPE: PRT
<213> ORGANISM: Homo sapiens

<400> SEQUENCE: 196

Lys Ile Gln Glu Ile Leu Thr Gln Val
1               5

<210> SEQ ID NO 197
<211> LENGTH: 10
<212> TYPE: PRT
<213> ORGANISM: Homo sapiens

<400> SEQUENCE: 197

Ser Leu Phe Gly Gln Asp Val Lys Ala Val
1               5                   10

<210> SEQ ID NO 198
<211> LENGTH: 10
<212> TYPE: PRT
<213> ORGANISM: Homo sapiens

<400> SEQUENCE: 198

Val Leu Tyr Gly Pro Asp Val Pro Thr Ile
1               5                   10

<210> SEQ ID NO 199
<211> LENGTH: 9
<212> TYPE: PRT
<213> ORGANISM: Homo sapiens

<400> SEQUENCE: 199

Phe Leu Leu Glu Arg Glu Gln Leu Leu
1               5

<210> SEQ ID NO 200
<211> LENGTH: 9
<212> TYPE: PRT
<213> ORGANISM: Homo sapiens

<400> SEQUENCE: 200

Ser Ala Val Asp Phe Ile Arg Thr Leu
```

```
<210> SEQ ID NO 201
<211> LENGTH: 10
<212> TYPE: PRT
<213> ORGANISM: Homo sapiens

<400> SEQUENCE: 201

Gly Ser Phe Asn Gly Ala Leu Ala Ala Val
1               5                   10

<210> SEQ ID NO 202
<211> LENGTH: 9
<212> TYPE: PRT
<213> ORGANISM: Homo sapiens

<400> SEQUENCE: 202

Gly Leu Ala Ala Leu Ala Val His Leu
1               5

<210> SEQ ID NO 203
<211> LENGTH: 11
<212> TYPE: PRT
<213> ORGANISM: Homo sapiens

<400> SEQUENCE: 203

Lys Leu Ile Asp Leu Ser Gln Val Met Tyr Leu
1               5                   10

<210> SEQ ID NO 204
<211> LENGTH: 12
<212> TYPE: PRT
<213> ORGANISM: Homo sapiens

<400> SEQUENCE: 204

Lys Leu Leu Asp Leu Glu Thr Glu Arg Ile Leu Leu
1               5                   10

<210> SEQ ID NO 205
<211> LENGTH: 9
<212> TYPE: PRT
<213> ORGANISM: Homo sapiens

<400> SEQUENCE: 205

Arg Leu His Asp Glu Asn Ile Leu Leu
1               5

<210> SEQ ID NO 206
<211> LENGTH: 11
<212> TYPE: PRT
<213> ORGANISM: Homo sapiens

<400> SEQUENCE: 206

Arg Ile Ala Gly Ile Arg Gly Ile Gln Gly Val
1               5                   10

<210> SEQ ID NO 207
<211> LENGTH: 9
<212> TYPE: PRT
<213> ORGANISM: Homo sapiens

<400> SEQUENCE: 207

Lys Leu Cys Glu Gly Phe Asn Glu Val
1               5
```

<210> SEQ ID NO 208
<211> LENGTH: 9
<212> TYPE: PRT
<213> ORGANISM: Homo sapiens

<400> SEQUENCE: 208

Arg Leu Ile Asp Arg Ile Lys Thr Val
1               5

<210> SEQ ID NO 209
<211> LENGTH: 9
<212> TYPE: PRT
<213> ORGANISM: Homo sapiens

<400> SEQUENCE: 209

Lys Leu Gln Asp Gly Leu Leu His Ile
1               5

<210> SEQ ID NO 210
<211> LENGTH: 9
<212> TYPE: PRT
<213> ORGANISM: Homo sapiens

<400> SEQUENCE: 210

Lys Leu Ala Val Ala Leu Leu Ala Ala
1               5

<210> SEQ ID NO 211
<211> LENGTH: 9
<212> TYPE: PRT
<213> ORGANISM: Homo sapiens

<400> SEQUENCE: 211

Ser Leu Phe Gly Lys Lys Tyr Ile Leu
1               5

<210> SEQ ID NO 212
<211> LENGTH: 9
<212> TYPE: PRT
<213> ORGANISM: Homo sapiens

<400> SEQUENCE: 212

Phe Leu Leu Asp Gly Ser Ala Asn Val
1               5

<210> SEQ ID NO 213
<211> LENGTH: 9
<212> TYPE: PRT
<213> ORGANISM: Homo sapiens

<400> SEQUENCE: 213

Leu Leu Trp Ala Pro Thr Ala Gln Ala
1               5

<210> SEQ ID NO 214
<211> LENGTH: 10
<212> TYPE: PRT
<213> ORGANISM: Homo sapiens

<400> SEQUENCE: 214

Ser Val Leu Glu Lys Glu Ile Tyr Ser Ile
1               5                   10

<210> SEQ ID NO 215

```
<211> LENGTH: 9
<212> TYPE: PRT
<213> ORGANISM: Homo sapiens

<400> SEQUENCE: 215

Lys Leu Gln Glu Lys Ile Gln Glu Leu
1               5

<210> SEQ ID NO 216
<211> LENGTH: 12
<212> TYPE: PRT
<213> ORGANISM: Homo sapiens

<400> SEQUENCE: 216

Tyr Leu Trp Asp Leu Asp His Gly Phe Ala Gly Val
1               5                   10

<210> SEQ ID NO 217
<211> LENGTH: 11
<212> TYPE: PRT
<213> ORGANISM: Homo sapiens

<400> SEQUENCE: 217

Lys Leu Leu Asp Thr Met Val Asp Thr Phe Leu
1               5                   10

<210> SEQ ID NO 218
<211> LENGTH: 9
<212> TYPE: PRT
<213> ORGANISM: Homo sapiens

<400> SEQUENCE: 218

Lys Leu Ser Trp Asp Leu Ile Tyr Leu
1               5

<210> SEQ ID NO 219
<211> LENGTH: 9
<212> TYPE: PRT
<213> ORGANISM: Homo sapiens

<400> SEQUENCE: 219

Phe Leu Asp Glu Lys Gly Arg Cys Val
1               5

<210> SEQ ID NO 220
<211> LENGTH: 9
<212> TYPE: PRT
<213> ORGANISM: Homo sapiens

<400> SEQUENCE: 220

Lys Met Asp Pro Val Ala Tyr Arg Val
1               5

<210> SEQ ID NO 221
<211> LENGTH: 10
<212> TYPE: PRT
<213> ORGANISM: Homo sapiens

<400> SEQUENCE: 221

Ile Leu Asn Val Asp Gly Leu Ile Gly Val
1               5                   10

<210> SEQ ID NO 222
<211> LENGTH: 10
<212> TYPE: PRT
```

<213> ORGANISM: Homo sapiens

<400> SEQUENCE: 222

Gly Val Ile Ala Glu Ile Leu Arg Gly Val
1               5                   10

<210> SEQ ID NO 223
<211> LENGTH: 10
<212> TYPE: PRT
<213> ORGANISM: Homo sapiens

<400> SEQUENCE: 223

Val Leu Met Gln Asp Ser Arg Leu Tyr Leu
1               5                   10

<210> SEQ ID NO 224
<211> LENGTH: 11
<212> TYPE: PRT
<213> ORGANISM: Homo sapiens

<400> SEQUENCE: 224

Gln Leu Gln Glu Gly Lys Asn Val Ile Gly Leu
1               5                   10

<210> SEQ ID NO 225
<211> LENGTH: 10
<212> TYPE: PRT
<213> ORGANISM: Homo sapiens

<400> SEQUENCE: 225

Tyr Leu Tyr Gly Gln Thr Thr Thr Tyr Leu
1               5                   10

<210> SEQ ID NO 226
<211> LENGTH: 9
<212> TYPE: PRT
<213> ORGANISM: Homo sapiens

<400> SEQUENCE: 226

Phe Leu Val Asp Gly Ser Trp Ser Val
1               5

<210> SEQ ID NO 227
<211> LENGTH: 11
<212> TYPE: PRT
<213> ORGANISM: Homo sapiens

<400> SEQUENCE: 227

Leu Thr Ala Pro Pro Glu Ala Leu Leu Met Val
1               5                   10

<210> SEQ ID NO 228
<211> LENGTH: 9
<212> TYPE: PRT
<213> ORGANISM: Homo sapiens

<400> SEQUENCE: 228

Ser Met Ser Gly Tyr Asp Gln Val Leu
1               5

<210> SEQ ID NO 229
<211> LENGTH: 9
<212> TYPE: PRT
<213> ORGANISM: Homo sapiens

```
<400> SEQUENCE: 229

Tyr Leu Leu Glu Lys Phe Val Ala Val
1               5

<210> SEQ ID NO 230
<211> LENGTH: 9
<212> TYPE: PRT
<213> ORGANISM: Homo sapiens

<400> SEQUENCE: 230

Ala Met Ser Ser Lys Phe Phe Leu Val
1               5

<210> SEQ ID NO 231
<211> LENGTH: 10
<212> TYPE: PRT
<213> ORGANISM: Homo sapiens

<400> SEQUENCE: 231

Arg Leu Phe Ala Asp Ile Leu Asn Asp Val
1               5                   10

<210> SEQ ID NO 232
<211> LENGTH: 9
<212> TYPE: PRT
<213> ORGANISM: Homo sapiens

<400> SEQUENCE: 232

Arg Leu Leu Asp Ser Val Ser Arg Leu
1               5

<210> SEQ ID NO 233
<211> LENGTH: 9
<212> TYPE: PRT
<213> ORGANISM: Homo sapiens

<400> SEQUENCE: 233

Arg Leu Asp Asp Leu Lys Met Thr Val
1               5

<210> SEQ ID NO 234
<211> LENGTH: 10
<212> TYPE: PRT
<213> ORGANISM: Homo sapiens

<400> SEQUENCE: 234

Lys Met Phe Glu Ser Phe Ile Glu Ser Val
1               5                   10

<210> SEQ ID NO 235
<211> LENGTH: 9
<212> TYPE: PRT
<213> ORGANISM: Homo sapiens

<400> SEQUENCE: 235

Leu Leu His Glu Glu Asn Phe Ser Val
1               5

<210> SEQ ID NO 236
<211> LENGTH: 9
<212> TYPE: PRT
<213> ORGANISM: Homo sapiens

<400> SEQUENCE: 236
```

```
Lys Met Ser Glu Leu Gln Thr Tyr Val
1               5
```

<210> SEQ ID NO 237
<211> LENGTH: 10
<212> TYPE: PRT
<213> ORGANISM: Homo sapiens

<400> SEQUENCE: 237

```
Lys Leu Val Glu Phe Asp Phe Leu Gly Ala
1               5                   10
```

<210> SEQ ID NO 238
<211> LENGTH: 9
<212> TYPE: PRT
<213> ORGANISM: Homo sapiens

<400> SEQUENCE: 238

```
Asn Met Leu Glu Ala Val His Thr Ile
1               5
```

<210> SEQ ID NO 239
<211> LENGTH: 9
<212> TYPE: PRT
<213> ORGANISM: Homo sapiens

<400> SEQUENCE: 239

```
Gln Leu Ile Glu Lys Asn Trp Leu Leu
1               5
```

<210> SEQ ID NO 240
<211> LENGTH: 9
<212> TYPE: PRT
<213> ORGANISM: Homo sapiens

<400> SEQUENCE: 240

```
Val Leu Ala Pro Arg Val Leu Arg Ala
1               5
```

<210> SEQ ID NO 241
<211> LENGTH: 9
<212> TYPE: PRT
<213> ORGANISM: Homo sapiens

<400> SEQUENCE: 241

```
Ile Leu Ile Asp Trp Leu Val Gln Val
1               5
```

<210> SEQ ID NO 242
<211> LENGTH: 11
<212> TYPE: PRT
<213> ORGANISM: Homo sapiens

<400> SEQUENCE: 242

```
Arg Leu Glu Glu Asp Asp Gly Asp Val Ala Met
1               5                   10
```

<210> SEQ ID NO 243
<211> LENGTH: 10
<212> TYPE: PRT
<213> ORGANISM: Homo sapiens

<400> SEQUENCE: 243

```
Thr Leu Met Asp Met Arg Leu Ser Gln Val
1               5                   10
```

<210> SEQ ID NO 244
<211> LENGTH: 9
<212> TYPE: PRT
<213> ORGANISM: Homo sapiens

<400> SEQUENCE: 244

Ser Leu His Phe Leu Ile Leu Tyr Val
1               5

<210> SEQ ID NO 245
<211> LENGTH: 9
<212> TYPE: PRT
<213> ORGANISM: Homo sapiens

<400> SEQUENCE: 245

Gln Leu Ile Asp Tyr Glu Arg Gln Leu
1               5

<210> SEQ ID NO 246
<211> LENGTH: 9
<212> TYPE: PRT
<213> ORGANISM: Homo sapiens

<400> SEQUENCE: 246

Gly Leu Thr Asp Asn Ile His Leu Val
1               5

<210> SEQ ID NO 247
<211> LENGTH: 9
<212> TYPE: PRT
<213> ORGANISM: Homo sapiens

<400> SEQUENCE: 247

Ser Leu Asp Thr Leu Met Thr Tyr Val
1               5

<210> SEQ ID NO 248
<211> LENGTH: 9
<212> TYPE: PRT
<213> ORGANISM: Homo sapiens

<400> SEQUENCE: 248

Ala Leu Tyr Gly Asp Ile Asp Ala Val
1               5

<210> SEQ ID NO 249
<211> LENGTH: 9
<212> TYPE: PRT
<213> ORGANISM: Homo sapiens

<400> SEQUENCE: 249

Ala Leu Tyr Gly Arg Leu Glu Val Val
1               5

<210> SEQ ID NO 250
<211> LENGTH: 10
<212> TYPE: PRT
<213> ORGANISM: Homo sapiens

<400> SEQUENCE: 250

Ala Leu Cys Glu Glu Asn Met Arg Gly Val
1               5                   10

```
<210> SEQ ID NO 251
<211> LENGTH: 11
<212> TYPE: PRT
<213> ORGANISM: Homo sapiens

<400> SEQUENCE: 251

Ser Leu Leu Gln Ala Thr Asp Phe Met Ser Leu
1               5                   10

<210> SEQ ID NO 252
<211> LENGTH: 9
<212> TYPE: PRT
<213> ORGANISM: Homo sapiens

<400> SEQUENCE: 252

Tyr Val Tyr Gln Asn Asn Ile Tyr Leu
1               5

<210> SEQ ID NO 253
<211> LENGTH: 11
<212> TYPE: PRT
<213> ORGANISM: Homo sapiens

<400> SEQUENCE: 253

Lys Leu Leu Asp Glu Val Thr Tyr Leu Glu Ala
1               5                   10

<210> SEQ ID NO 254
<211> LENGTH: 10
<212> TYPE: PRT
<213> ORGANISM: Homo sapiens

<400> SEQUENCE: 254

Val Leu Phe Gln Glu Ala Leu Trp His Val
1               5                   10

<210> SEQ ID NO 255
<211> LENGTH: 9
<212> TYPE: PRT
<213> ORGANISM: Homo sapiens

<400> SEQUENCE: 255

Ala Leu Ala Leu Trp Ile Pro Ser Leu
1               5

<210> SEQ ID NO 256
<211> LENGTH: 9
<212> TYPE: PRT
<213> ORGANISM: Homo sapiens

<400> SEQUENCE: 256

Gly Leu Leu Glu Glu Leu Val Thr Val
1               5

<210> SEQ ID NO 257
<211> LENGTH: 9
<212> TYPE: PRT
<213> ORGANISM: Homo sapiens

<400> SEQUENCE: 257

Ser Leu Ala Asp Phe Met Gln Glu Val
1               5

<210> SEQ ID NO 258
<211> LENGTH: 9
```

```
<212> TYPE: PRT
<213> ORGANISM: Homo sapiens

<400> SEQUENCE: 258

Leu Leu Tyr Glu Gly Lys Leu Thr Leu
1               5

<210> SEQ ID NO 259
<211> LENGTH: 11
<212> TYPE: PRT
<213> ORGANISM: Homo sapiens

<400> SEQUENCE: 259

Ala Leu Ala Asp Lys Glu Leu Leu Pro Ser Val
1               5                   10

<210> SEQ ID NO 260
<211> LENGTH: 10
<212> TYPE: PRT
<213> ORGANISM: Homo sapiens

<400> SEQUENCE: 260

Ala Leu Leu Ala Glu Gly Ile Thr Trp Val
1               5                   10

<210> SEQ ID NO 261
<211> LENGTH: 10
<212> TYPE: PRT
<213> ORGANISM: Homo sapiens

<400> SEQUENCE: 261

Tyr Leu Tyr Asp Ser Glu Thr Lys Asn Ala
1               5                   10

<210> SEQ ID NO 262
<211> LENGTH: 10
<212> TYPE: PRT
<213> ORGANISM: Homo sapiens

<400> SEQUENCE: 262

Val Leu Ala Lys Pro Gly Val Ile Ser Val
1               5                   10

<210> SEQ ID NO 263
<211> LENGTH: 9
<212> TYPE: PRT
<213> ORGANISM: Homo sapiens

<400> SEQUENCE: 263

Leu Leu Ala Gly Gln Thr Tyr His Val
1               5

<210> SEQ ID NO 264
<211> LENGTH: 10
<212> TYPE: PRT
<213> ORGANISM: Homo sapiens

<400> SEQUENCE: 264

Arg Leu Leu Asp Val Leu Ala Pro Leu Val
1               5                   10

<210> SEQ ID NO 265
<211> LENGTH: 8
<212> TYPE: PRT
<213> ORGANISM: Homo sapiens
```

```
<400> SEQUENCE: 265

Leu Leu Asp Lys Lys Ile Gly Val
1               5

<210> SEQ ID NO 266
<211> LENGTH: 10
<212> TYPE: PRT
<213> ORGANISM: Homo sapiens

<400> SEQUENCE: 266

Glu Leu Ala Gly Ile Gly Ile Leu Thr Val
1               5                   10

<210> SEQ ID NO 267
<211> LENGTH: 9
<212> TYPE: PRT
<213> ORGANISM: Homo sapiens

<400> SEQUENCE: 267

Tyr Leu Leu Pro Ala Ile Val His Ile
1               5
```